US011467165B2

(12) United States Patent
Haecker et al.

(10) Patent No.: US 11,467,165 B2
(45) Date of Patent: *Oct. 11, 2022

(54) RAPID ASSAY FOR DETECTION OF SARS-COV-2 ANTIBODIES

(71) Applicant: UNIVERSITY OF UTAH RESEARCH FOUNDATION, Salt Lake City, UT (US)

(72) Inventors: Hans Haecker, Salt Lake City, UT (US); Vanessa Redecke, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/478,527

(22) Filed: Sep. 17, 2021

(65) Prior Publication Data

US 2022/0214352 A1 Jul. 7, 2022

Related U.S. Application Data

(62) Division of application No. 17/140,321, filed on Jan. 4, 2021, now Pat. No. 11,175,293.

(51) Int. Cl.

*C07K 14/165* (2006.01)
*G01N 33/68* (2006.01)
*C07K 16/10* (2006.01)
*C07K 16/30* (2006.01)
*G01N 33/49* (2006.01)
*C07K 14/47* (2006.01)

(52) U.S. Cl.

CPC ........... *G01N 33/68* (2013.01); *C07K 14/165* (2013.01); *C07K 14/47* (2013.01); *C07K 16/10* (2013.01); *C07K 16/3061* (2013.01); *G01N 33/49* (2013.01); *C07K 2319/02* (2013.01); *C07K 2319/30* (2013.01); *C07K 2319/73* (2013.01)

(58) Field of Classification Search

None

See application file for complete search history.

(56) References Cited

U.S. PATENT DOCUMENTS

| | | | |
|---|---|---|---|
| 9,879,090 | B2 | 1/2018 | Bertrand et al. |
| 2007/0042350 | A1 | 2/2007 | Li et al. |
| 2007/0053878 | A1 | 3/2007 | Haagmans et al. |
| 2007/0248616 | A1 | 10/2007 | Brownlie et al. |
| 2009/0029924 | A1 | 1/2009 | Strongin et al. |
| 2012/0258126 | A1 | 10/2012 | Scholler et al. |
| 2014/0120113 | A1 | 5/2014 | Kwaks et al. |
| 2015/0110826 | A1 | 4/2015 | Bayne et al. |
| 2017/0269101 | A1 | 9/2017 | Yerramilli et al. |
| 2017/0356921 | A1 | 12/2017 | Van Roosmalen et al. |
| 2018/0292408 | A1 | 10/2018 | Qi |
| 2020/0040042 | A1 | 2/2020 | Chappell et al. |

FOREIGN PATENT DOCUMENTS

| | | | |
|---|---|---|---|
| AU | 4876399 | A | 11/1999 |
| CN | 108463229 | A | 8/2018 |
| CN | 108778308 | A | 11/2018 |
| CN | 109503711 | A | 3/2019 |
| KR | 20180118175 | A | 10/2018 |
| WO | 2007053165 | A2 | 5/2007 |
| WO | 2017068352 | A1 | 4/2017 |
| WO | 2017070364 | A1 | 8/2018 |
| WO | 2019217967 | A1 | 11/2019 |
| WO | 2020099922 | A1 | 5/2020 |
| WO | 2020163721 | A1 | 8/2020 |
| WO | 2021222772 | A2 | 11/2021 |

OTHER PUBLICATIONS

Dutta et al., "Search for potential target site of nucleocapsid gene for the design of an epitope-based SARS DNA vaccine," Immunol. Let., vol. 118, 2008, pp. 65-71.

Dutta et al., "The Nucleocapsid Protein of SARS-CoV-2: a Target for Vaccine Development," J. Virol., vol. 94, No. 13, 2020, pp. e00647-20.

Grant et al., "Analysis of the SARS-CoV-2 spike protein glycan shield reveals implications for immune recognition," Sci. Rep., vol. 10, 2020, 12 pages.

Grzelak et al., "A comparison of four serological assays for detecting anti-SARS- CoV-2 antibodies in human serum samples from different populations," Sci. Transl. Med., vol. 12, 2020, eabc3103, 15 pages.

Gudbjartsson et al., "Humoral Immune Response to SARS-CoV-2 in Iceland," N. Engl. J. Med., vol. 383, No. 18, 2020, pp. 1724-1734.

Gupta et al., "Expression, purification, and characterization of an anti-RBCFab-p24 fusion protein for hemagglutination-based rapid detection of antibodies to HIV in whole blood," Protein Expr. Purif., vol. 26, 2002, pp. 162-170.

Gupta et al., "Whole-blood agglutination assay for on-site detection of human immunodeficiency virus infection," J. Clin. Microbiol., vol. 41, No. 7, 2003, pp. 2814-2821.

Habib et al., "V(H)H (nanobody) directed against human glycophorin A: a tool for autologous red cell agglutination assays," Anal. Biochem., vol. 438, 2013, pp. 82-89.

Hachim et al., "ORF8 and ORF3b antibodies are accurate serological markers of early and late SARS-CoV-2 infection," Nat. Immunol., vol. 21,, 2020, pp. 1293-1301.

Huo et al., "Neutralizing nanobodies bind SARS-CoV-2 spike RBD and block interaction with ACE2", Nature Structural & Molecular Biology, vol. 27, 2020, pp. 846-854.

Kemp et al., "Autologous red cell agglutination assay for HIV-1 antibodies: simplified test with whole blood," Science, vol. 241, 1988, pp. 1352-1354.

(Continued)

*Primary Examiner* — Michael D Burkhart

(74) *Attorney, Agent, or Firm* — Michael Best & Friedrich LLP

(57) ABSTRACT

Described herein are diagnostic and control fusion protein reagents and methods for use thereof in simple rapid and inexpensive hemagglutinin assays for the detection of subject antibodies directed to the SARS-CoV-2 virus.

20 Claims, 8 Drawing Sheets

Specification includes a Sequence Listing.

(56) References Cited

OTHER PUBLICATIONS

Kontou et al., "Antibody Tests in Detecting SARS-CoV- 2 Infection: A Meta-Analysis," Diagnostics, vol. 10, No. 319, 2020, 15 pages.
Lee et al., "Detection of antibodies against SARS-Coronavirus using recombinant truncated nucleocapsid proteins by ELISA," J. Microbiol. Biotechnol., vol. 18, No. 10, 2008, pp. 1717-1721.
Lee et al., "Production of specific antibodies against SARS-coronavirus nucleocapsid protein without cross reactivity with human coronaviruses 229E and OC43," J. Vet. Sci., vol. 11, No. 2, 2010, pp. 165-167.
Okba et al., "Serologic Detection of Middle East Respiratory Syndrome Coronavirus Functional Antibodies", Emerging Infectious Dis, vol. 26, No. 5, 2020, pp. 1024-1027.
Ravichandran et al., "Antibody signature induced by SARS-CoV-2 spike protein immunogens in rabbits," Sci. Transl. Med., vol. 12, 2002, eabc3539, 7 pages.
Redecke et al., "Hematopoietic progenitor cell lines with myeloid and lymphoid potential," Nat. Methods, vol. 10, No. 8, 2013, pp. 795-803.
Sah et al., "Complete Genome Sequence of a 2019 Novel Coronavirus (SARS-CoV-2) Strain Isolated in Nepal", American Society for Microbiology, vol. 9, Issue 11, 2020, 3 pages.
Salvatori et al., "SARS-CoV-2 Spike Protein: an optimal immunological target for vaccines," J. Transl. Med., vol. 18, No. 222, 2020, 3 pages.
Tai et al., "Characterization of the receptor-binding domain (RBD) of 2019 novel coronavirus: implication for development of RBD protein as a viral attachment inhibitor and vaccine," Cell. Mol. Immunol., vol. 17, No. 6, 2020, pp. 613-620.
Tillib et al., "Formatted single-domain antibodies can protect mice against infection with influenza virus (H5N2)", Antiviral Research, vol. 97, 2013, pp. 245-254.
Townsend et al., "A haemagglutination test for rapid detection of antibodies to SARS-CoV-2", Nature Communications, Mar. 2021, pp. 1-6.
Kruse et al., "A rapid, point of care red blood cell agglutination assay for detecting antibodies against SARS-Cov-2," bioRxiv preprint, May 14, 2020, 13 pages.
Kruse et al., "A rapid, point-of-care red blood cell agglutination assay detecting antibodies against SARS-CoV-2," Biochem Biophys Res Commun., 2021, vol. 553, pp. 165-171.
Esmail et al., "Rapid and accurate point-of-care testing for SARS-CoV2 antibodies," medRxiv preprint, Dec. 2, 2020, 29 pages.
Esmail et al, "Rapid and accurate agglutination-based testing for SARS-CoV-2 antibodies," Cell Reports Methods 1, Jun. 21, 2021, 18 pages.

SEQUENCE LISTING

```
<160> NUMBER OF SEQ ID NOS: 67

<210> SEQ ID NO 1
<211> LENGTH: 1260
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1260)

<400> SEQUENCE: 1

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg ggc gcg cct caa gtt cag ctt caa gaa tct       96
Thr Thr Ala Leu Ser Met Gly Ala Pro Gln Val Gln Leu Gln Glu Ser
            20                  25                  30

ggc ggc gga agc gtt cag gct ggc gga tct ctg aga ctg agc tgt gtg      144
Gly Gly Gly Ser Val Gln Ala Gly Gly Ser Leu Arg Leu Ser Cys Val
        35                  40                  45

gcc agc ggc tac acc gat agc aca tac tgc gtc ggc tgg ttc aga cag      192
Ala Ser Gly Tyr Thr Asp Ser Thr Tyr Cys Val Gly Trp Phe Arg Gln
    50                  55                  60

gcc cct ggc aaa gag aga gag ggc gtc gcc aga atc aac acc atc agc      240
Ala Pro Gly Lys Glu Arg Glu Gly Val Ala Arg Ile Asn Thr Ile Ser
65                  70                  75                  80

ggc aga cct tgg tac gcc gac tct gtg aag ggc aga ttc aca atc agc      288
Gly Arg Pro Trp Tyr Ala Asp Ser Val Lys Gly Arg Phe Thr Ile Ser
                85                  90                  95

cag gac aac agc aag aac acc gtg tac ctg cag atg aac agc ctg aag      336
Gln Asp Asn Ser Lys Asn Thr Val Tyr Leu Gln Met Asn Ser Leu Lys
            100                 105                 110

cct gag gac acc gcc atc tac tac tgc acc ctg acc acc gcc aac agc      384
Pro Glu Asp Thr Ala Ile Tyr Tyr Cys Thr Leu Thr Thr Ala Asn Ser
        115                 120                 125

aga ggc ttt tgt tcc ggc ggc tac aac tac aaa ggc cag ggc acc caa      432
Arg Gly Phe Cys Ser Gly Gly Tyr Asn Tyr Lys Gly Gln Gly Thr Gln
    130                 135                 140

gtg acc gtg tct ggt ggt acc agc gga ggc gga gga tca ggt ggc gga      480
Val Thr Val Ser Gly Gly Thr Ser Gly Gly Gly Gly Ser Gly Gly Gly
145                 150                 155                 160

ggt agt ggt ggt ggc ggt agc gcg gcc gct aga ttc ccc aac atc acc      528
Gly Ser Gly Gly Gly Gly Ser Ala Ala Ala Arg Phe Pro Asn Ile Thr
                165                 170                 175

aat ctg tgc ccc ttc ggc gag gtg ttc aac gcc aca aga ttc gcc tct      576
Asn Leu Cys Pro Phe Gly Glu Val Phe Asn Ala Thr Arg Phe Ala Ser
            180                 185                 190

gtg tac gcc tgg aac cgg aag cgg atc agc aat tgc gtg gcc gac tac      624
Val Tyr Ala Trp Asn Arg Lys Arg Ile Ser Asn Cys Val Ala Asp Tyr
        195                 200                 205

agc gtg ctg tac aac agc gcc agc ttc tcc acc ttc aag tgc tac ggc      672
Ser Val Leu Tyr Asn Ser Ala Ser Phe Ser Thr Phe Lys Cys Tyr Gly
    210                 215                 220

gtg tcc cct acc aag ctg aac gac ctg tgc ttt acc aac gtg tac gcc      720
Val Ser Pro Thr Lys Leu Asn Asp Leu Cys Phe Thr Asn Val Tyr Ala
225                 230                 235                 240

gat agc ttc gtg atc cgg gga gat gaa gtg cgg cag atc gct cct gga      768
Asp Ser Phe Val Ile Arg Gly Asp Glu Val Arg Gln Ile Ala Pro Gly
                245                 250                 255
```

-continued

```
cag aca ggc aag atc gcc gac tat aac tac aag ctg ccc gac gac ttc      816
Gln Thr Gly Lys Ile Ala Asp Tyr Asn Tyr Lys Leu Pro Asp Asp Phe
            260                 265                 270

acc ggc tgt gtg att gcc tgg aac agc aac aac ctg gac agc aaa gtc      864
Thr Gly Cys Val Ile Ala Trp Asn Ser Asn Asn Leu Asp Ser Lys Val
        275                 280                 285

ggc ggc aac tac aat tac ctg tac cgg ctg ttc cgg aag tcc aat ctg      912
Gly Gly Asn Tyr Asn Tyr Leu Tyr Arg Leu Phe Arg Lys Ser Asn Leu
    290                 295                 300

aag ccc ttc gag cgg gac atc agc acc gag atc tat cag gcc ggc agc      960
Lys Pro Phe Glu Arg Asp Ile Ser Thr Glu Ile Tyr Gln Ala Gly Ser
305                 310                 315                 320

acc cct tgc aat ggc gtg gaa ggc ttc aac tgc tac ttc cca ctg cag     1008
Thr Pro Cys Asn Gly Val Glu Gly Phe Asn Cys Tyr Phe Pro Leu Gln
                325                 330                 335

tcc tac ggc ttc cag cct aca aac ggc gtg ggc tac cag cct tac aga     1056
Ser Tyr Gly Phe Gln Pro Thr Asn Gly Val Gly Tyr Gln Pro Tyr Arg
            340                 345                 350

gtg gtg gtc ctg agc ttc gag ctg ctg cat gcc cct gct aca gtg tgc     1104
Val Val Val Leu Ser Phe Glu Leu Leu His Ala Pro Ala Thr Val Cys
        355                 360                 365

ggc cct aag aag tct acc aac ctg gaa ttc ggc gga ggc agc ggc ggt     1152
Gly Pro Lys Lys Ser Thr Asn Leu Glu Phe Gly Gly Gly Ser Gly Gly
    370                 375                 380

gga agc ggc gga ggc tct gct tgg agc cac ccg cag ttc gaa aaa ggt     1200
Gly Ser Gly Gly Gly Ser Ala Trp Ser His Pro Gln Phe Glu Lys Gly
385                 390                 395                 400

gga ggt tct ggc ggt gga tcg gga ggt tca gcg tgg agc cac ccg cag     1248
Gly Gly Ser Gly Gly Gly Ser Gly Gly Ser Ala Trp Ser His Pro Gln
                405                 410                 415

ttc gag aaa tga                                                     1260
Phe Glu Lys


<210> SEQ ID NO 2
<211> LENGTH: 419
<212> TYPE: PRT
<213> ORGANISM: Artificial Sequence
<220> FEATURE:
<223> OTHER INFORMATION: Synthetic Construct

<400> SEQUENCE: 2

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80

Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125

Arg Gly Phe Cys Ser Gly Gly Tyr Asn Tyr Lys Gly Gln Gly Thr Gln
    130                 135                 140
```

```
Val Thr Val Ser Gly Gly Thr Ser Gly Gly Gly Gly Ser Gly Gly Gly
145                 150                 155                 160

Gly Ser Gly Gly Gly Gly Ser Ala Ala Ala Arg Phe Pro Asn Ile Thr
                165                 170                 175

Asn Leu Cys Pro Phe Gly Glu Val Phe Asn Ala Thr Arg Phe Ala Ser
            180                 185                 190

Val Tyr Ala Trp Asn Arg Lys Arg Ile Ser Asn Cys Val Ala Asp Tyr
        195                 200                 205

Ser Val Leu Tyr Asn Ser Ala Ser Phe Ser Thr Phe Lys Cys Tyr Gly
    210                 215                 220

Val Ser Pro Thr Lys Leu Asn Asp Leu Cys Phe Thr Asn Val Tyr Ala
225                 230                 235                 240

Asp Ser Phe Val Ile Arg Gly Asp Glu Val Arg Gln Ile Ala Pro Gly
                245                 250                 255

Gln Thr Gly Lys Ile Ala Asp Tyr Asn Tyr Lys Leu Pro Asp Asp Phe
            260                 265                 270

Thr Gly Cys Val Ile Ala Trp Asn Ser Asn Asn Leu Asp Ser Lys Val
        275                 280                 285

Gly Gly Asn Tyr Asn Tyr Leu Tyr Arg Leu Phe Arg Lys Ser Asn Leu
    290                 295                 300

Lys Pro Phe Glu Arg Asp Ile Ser Thr Glu Ile Tyr Gln Ala Gly Ser
305                 310                 315                 320

Thr Pro Cys Asn Gly Val Glu Gly Phe Asn Cys Tyr Phe Pro Leu Gln
                325                 330                 335

Ser Tyr Gly Phe Gln Pro Thr Asn Gly Val Gly Tyr Gln Pro Tyr Arg
            340                 345                 350

Val Val Val Leu Ser Phe Glu Leu Leu His Ala Pro Ala Thr Val Cys
        355                 360                 365

Gly Pro Lys Lys Ser Thr Asn Leu Glu Phe Gly Gly Gly Ser Gly Gly
    370                 375                 380

Gly Ser Gly Gly Gly Ser Ala Trp Ser His Pro Gln Phe Glu Lys Gly
385                 390                 395                 400

Gly Gly Ser Gly Gly Gly Ser Gly Gly Ser Ala Trp Ser His Pro Gln
                405                 410                 415

Phe Glu Lys


<210> SEQ ID NO 3
<211> LENGTH: 1899
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1899)

<400> SEQUENCE: 3

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg ggc gcg cct caa gtt cag ctt caa gaa tct       96
Thr Thr Ala Leu Ser Met Gly Ala Pro Gln Val Gln Leu Gln Glu Ser
            20                  25                  30

ggc ggc gga agc gtt cag gct ggc gga tct ctg aga ctg agc tgt gtg      144
Gly Gly Gly Ser Val Gln Ala Gly Gly Ser Leu Arg Leu Ser Cys Val
        35                  40                  45
```

-continued

```
gcc agc ggc tac acc gat agc aca tac tgc gtc ggc tgg ttc aga cag      192
Ala Ser Gly Tyr Thr Asp Ser Thr Tyr Cys Val Gly Trp Phe Arg Gln
    50                  55                  60

gcc cct ggc aaa gag aga gag ggc gtc gcc aga atc aac acc atc agc      240
Ala Pro Gly Lys Glu Arg Glu Gly Val Ala Arg Ile Asn Thr Ile Ser
65                  70                  75                  80

ggc aga cct tgg tac gcc gac tct gtg aag ggc aga ttc aca atc agc      288
Gly Arg Pro Trp Tyr Ala Asp Ser Val Lys Gly Arg Phe Thr Ile Ser
                85                  90                  95

cag gac aac agc aag aac acc gtg tac ctg cag atg aac agc ctg aag      336
Gln Asp Asn Ser Lys Asn Thr Val Tyr Leu Gln Met Asn Ser Leu Lys
            100                 105                 110

cct gag gac acc gcc atc tac tac tgc acc ctg acc acc gcc aac agc      384
Pro Glu Asp Thr Ala Ile Tyr Tyr Cys Thr Leu Thr Thr Ala Asn Ser
        115                 120                 125

aga ggc ttt tgt tcc ggc ggc tac aac tac aaa ggc cag ggc acc caa      432
Arg Gly Phe Cys Ser Gly Gly Tyr Asn Tyr Lys Gly Gln Gly Thr Gln
    130                 135                 140

gtg acc gtg tct ggt ggt acc agc gga ggc gga gga tca ggt ggc gga      480
Val Thr Val Ser Gly Gly Thr Ser Gly Gly Gly Gly Ser Gly Gly Gly
145                 150                 155                 160

ggt agt ggt ggt ggc ggt agc gcg gcc gcc atg tct gat aac ggc cct      528
Gly Ser Gly Gly Gly Gly Ser Ala Ala Ala Met Ser Asp Asn Gly Pro
                165                 170                 175

cag aac cag cgg aac gcc cct aga atc aca ttt ggc ggc cct agc gat      576
Gln Asn Gln Arg Asn Ala Pro Arg Ile Thr Phe Gly Gly Pro Ser Asp
            180                 185                 190

agc acc ggc agc aat cag aat ggc gag aga agc ggc gcc aga agc aag      624
Ser Thr Gly Ser Asn Gln Asn Gly Glu Arg Ser Gly Ala Arg Ser Lys
        195                 200                 205

cag aga agg cct caa ggc ctg cct aac aac acc gcc agc tgg ttc aca      672
Gln Arg Arg Pro Gln Gly Leu Pro Asn Asn Thr Ala Ser Trp Phe Thr
    210                 215                 220

gcc ctg aca cag cac ggc aaa gag gac ctg aag ttc ccc aga gga cag      720
Ala Leu Thr Gln His Gly Lys Glu Asp Leu Lys Phe Pro Arg Gly Gln
225                 230                 235                 240

ggc gtg ccc atc aac aca aac agc agc ccc gat gac cag atc ggc tac      768
Gly Val Pro Ile Asn Thr Asn Ser Ser Pro Asp Asp Gln Ile Gly Tyr
                245                 250                 255

tac aga cgg gcc acc aga aga atc aga ggc ggc gac ggc aag atg aag      816
Tyr Arg Arg Ala Thr Arg Arg Ile Arg Gly Gly Asp Gly Lys Met Lys
            260                 265                 270

gat ctg agc ccc aga tgg tac ttc tac tac ctc ggc aca gga ccc gaa      864
Asp Leu Ser Pro Arg Trp Tyr Phe Tyr Tyr Leu Gly Thr Gly Pro Glu
        275                 280                 285

gcc gga ctt cct tat ggc gcc aac aag gac ggc atc atc tgg gtt gca      912
Ala Gly Leu Pro Tyr Gly Ala Asn Lys Asp Gly Ile Ile Trp Val Ala
    290                 295                 300

aca gaa ggc gcc ctg aac acc cct aag gac cac atc ggc acc aga aat      960
Thr Glu Gly Ala Leu Asn Thr Pro Lys Asp His Ile Gly Thr Arg Asn
305                 310                 315                 320

ccc gcc aac aat gcc gcc att gtg ctg cag ttg cct cag ggc aca aca     1008
Pro Ala Asn Asn Ala Ala Ile Val Leu Gln Leu Pro Gln Gly Thr Thr
                325                 330                 335

ctg ccc aag ggc ttt tac gcc gag ggc agc aga ggc gga agc cag gcc     1056
Leu Pro Lys Gly Phe Tyr Ala Glu Gly Ser Arg Gly Gly Ser Gln Ala
            340                 345                 350

tct agc aga agc tcc agc aga agc cgg aac tcc agc cgg aat agc aca     1104
Ser Ser Arg Ser Ser Ser Arg Ser Arg Asn Ser Ser Arg Asn Ser Thr
        355                 360                 365
```

-continued

```
cct gga agc agc agg ggc aca agc cct gct aga atg gct ggc aat ggc      1152
Pro Gly Ser Ser Arg Gly Thr Ser Pro Ala Arg Met Ala Gly Asn Gly
    370                 375                 380

gga gat gct gct ctg gcc ctg ttg ctg ctg gac cgg ctg aat cag ctg      1200
Gly Asp Ala Ala Leu Ala Leu Leu Leu Leu Asp Arg Leu Asn Gln Leu
385                 390                 395                 400

gaa agc aag atg agc ggc aag ggc cag caa cag cag gga cag acc gtg      1248
Glu Ser Lys Met Ser Gly Lys Gly Gln Gln Gln Gln Gly Gln Thr Val
                405                 410                 415

acc aaa aag tct gcc gcc gag gcc agc aag aag ccc aga cag aaa aga      1296
Thr Lys Lys Ser Ala Ala Glu Ala Ser Lys Lys Pro Arg Gln Lys Arg
            420                 425                 430

acc gcc acc aag gcc tac aac gtg acc cag gcc ttt gga aga aga ggc      1344
Thr Ala Thr Lys Ala Tyr Asn Val Thr Gln Ala Phe Gly Arg Arg Gly
        435                 440                 445

cct gag cag acc cag ggc aac ttc gga gat caa gag ctg atc aga cag      1392
Pro Glu Gln Thr Gln Gly Asn Phe Gly Asp Gln Glu Leu Ile Arg Gln
    450                 455                 460

ggc acc gac tac aag cac tgg cct cag atc gcc cag ttt gcc cca tct      1440
Gly Thr Asp Tyr Lys His Trp Pro Gln Ile Ala Gln Phe Ala Pro Ser
465                 470                 475                 480

gcc agc gcc ttt ttc ggc atg agc cgg atc ggc atg gaa gtg aca cct      1488
Ala Ser Ala Phe Phe Gly Met Ser Arg Ile Gly Met Glu Val Thr Pro
                485                 490                 495

agc ggc acc tgg ctg aca tac aca ggc gcc atc aag ctg gac gac aag      1536
Ser Gly Thr Trp Leu Thr Tyr Thr Gly Ala Ile Lys Leu Asp Asp Lys
            500                 505                 510

gac ccc aac ttc aag gac caa gtg atc ctg ctg aac aag cac atc gac      1584
Asp Pro Asn Phe Lys Asp Gln Val Ile Leu Leu Asn Lys His Ile Asp
        515                 520                 525

gcc tac aag aca ttc cct cca acc gag cct aag aag gac aag aag aag      1632
Ala Tyr Lys Thr Phe Pro Pro Thr Glu Pro Lys Lys Asp Lys Lys Lys
    530                 535                 540

aag gcc gac gag aca cag gcc ctg cct cag cgc cag aaa aag cag cag      1680
Lys Ala Asp Glu Thr Gln Ala Leu Pro Gln Arg Gln Lys Lys Gln Gln
545                 550                 555                 560

aca gtg aca ctg ctg cca gcc gcc gac ctg gac gat ttt tct aag cag      1728
Thr Val Thr Leu Leu Pro Ala Ala Asp Leu Asp Asp Phe Ser Lys Gln
                565                 570                 575

ctg cag cag tcc atg agc agc gcc gat tct acc cag gcc gaa ttc ggc      1776
Leu Gln Gln Ser Met Ser Ser Ala Asp Ser Thr Gln Ala Glu Phe Gly
            580                 585                 590

gga ggt tca ggc ggt gga agt ggt ggt gga tct gct tgg agc cat cct      1824
Gly Gly Ser Gly Gly Gly Ser Gly Gly Gly Ser Ala Trp Ser His Pro
        595                 600                 605

cag ttc gag aaa ggc ggt ggt agc ggc gga gga agc ggt ggc tca gct      1872
Gln Phe Glu Lys Gly Gly Gly Ser Gly Gly Gly Ser Gly Gly Ser Ala
    610                 615                 620

tgg tca cac cca cag ttt gag aag tga                                  1899
Trp Ser His Pro Gln Phe Glu Lys
625                 630
```

<210> SEQ ID NO 4
<211> LENGTH: 632
<212> TYPE: PRT
<213> ORGANISM: Artificial Sequence
<220> FEATURE:
<223> OTHER INFORMATION: Synthetic Construct

<400> SEQUENCE: 4

-continued

Met Thr Asn Lys Cys Leu Leu Gln Ile Ala Leu Leu Leu Cys Phe Ser
1 5 10 15

Thr Thr Ala Leu Ser Met Gly Ala Pro Gln Val Gln Leu Gln Glu Ser
20 25 30

Gly Gly Gly Ser Val Gln Ala Gly Gly Ser Leu Arg Leu Ser Cys Val
35 40 45

Ala Ser Gly Tyr Thr Asp Ser Thr Tyr Cys Val Gly Trp Phe Arg Gln
50 55 60

Ala Pro Gly Lys Glu Arg Glu Gly Val Ala Arg Ile Asn Thr Ile Ser
65 70 75 80

Gly Arg Pro Trp Tyr Ala Asp Ser Val Lys Gly Arg Phe Thr Ile Ser
85 90 95

Gln Asp Asn Ser Lys Asn Thr Val Tyr Leu Gln Met Asn Ser Leu Lys
100 105 110

Pro Glu Asp Thr Ala Ile Tyr Tyr Cys Thr Leu Thr Thr Ala Asn Ser
115 120 125

Arg Gly Phe Cys Ser Gly Gly Tyr Asn Tyr Lys Gly Gln Gly Thr Gln
130 135 140

Val Thr Val Ser Gly Gly Thr Ser Gly Gly Gly Gly Ser Gly Gly Gly
145 150 155 160

Gly Ser Gly Gly Gly Gly Ser Ala Ala Ala Met Ser Asp Asn Gly Pro
165 170 175

Gln Asn Gln Arg Asn Ala Pro Arg Ile Thr Phe Gly Gly Pro Ser Asp
180 185 190

Ser Thr Gly Ser Asn Gln Asn Gly Glu Arg Ser Gly Ala Arg Ser Lys
195 200 205

Gln Arg Arg Pro Gln Gly Leu Pro Asn Asn Thr Ala Ser Trp Phe Thr
210 215 220

Ala Leu Thr Gln His Gly Lys Glu Asp Leu Lys Phe Pro Arg Gly Gln
225 230 235 240

Gly Val Pro Ile Asn Thr Asn Ser Ser Pro Asp Asp Gln Ile Gly Tyr
245 250 255

Tyr Arg Arg Ala Thr Arg Arg Ile Arg Gly Gly Asp Gly Lys Met Lys
260 265 270

Asp Leu Ser Pro Arg Trp Tyr Phe Tyr Tyr Leu Gly Thr Gly Pro Glu
275 280 285

Ala Gly Leu Pro Tyr Gly Ala Asn Lys Asp Gly Ile Ile Trp Val Ala
290 295 300

Thr Glu Gly Ala Leu Asn Thr Pro Lys Asp His Ile Gly Thr Arg Asn
305 310 315 320

Pro Ala Asn Asn Ala Ala Ile Val Leu Gln Leu Pro Gln Gly Thr Thr
325 330 335

Leu Pro Lys Gly Phe Tyr Ala Glu Gly Ser Arg Gly Gly Ser Gln Ala
340 345 350

Ser Ser Arg Ser Ser Ser Arg Ser Arg Asn Ser Ser Arg Asn Ser Thr
355 360 365

Pro Gly Ser Ser Arg Gly Thr Ser Pro Ala Arg Met Ala Gly Asn Gly
370 375 380

Gly Asp Ala Ala Leu Ala Leu Leu Leu Leu Asp Arg Leu Asn Gln Leu
385 390 395 400

Glu Ser Lys Met Ser Gly Lys Gly Gln Gln Gln Gln Gly Gln Thr Val
405 410 415

Thr Lys Lys Ser Ala Ala Glu Ala Ser Lys Lys Pro Arg Gln Lys Arg

-continued

```
            420                 425                 430

Thr Ala Thr Lys Ala Tyr Asn Val Thr Gln Ala Phe Gly Arg Arg Gly
        435                 440                 445

Pro Glu Gln Thr Gln Gly Asn Phe Gly Asp Gln Glu Leu Ile Arg Gln
    450                 455                 460

Gly Thr Asp Tyr Lys His Trp Pro Gln Ile Ala Gln Phe Ala Pro Ser
465                 470                 475                 480

Ala Ser Ala Phe Phe Gly Met Ser Arg Ile Gly Met Glu Val Thr Pro
                485                 490                 495

Ser Gly Thr Trp Leu Thr Tyr Thr Gly Ala Ile Lys Leu Asp Asp Lys
            500                 505                 510

Asp Pro Asn Phe Lys Asp Gln Val Ile Leu Leu Asn Lys His Ile Asp
        515                 520                 525

Ala Tyr Lys Thr Phe Pro Pro Thr Glu Pro Lys Lys Asp Lys Lys Lys
    530                 535                 540

Lys Ala Asp Glu Thr Gln Ala Leu Pro Gln Arg Gln Lys Lys Gln Gln
545                 550                 555                 560

Thr Val Thr Leu Leu Pro Ala Ala Asp Leu Asp Asp Phe Ser Lys Gln
                565                 570                 575

Leu Gln Gln Ser Met Ser Ser Ala Asp Ser Thr Gln Ala Glu Phe Gly
            580                 585                 590

Gly Gly Ser Gly Gly Gly Ser Gly Gly Gly Ser Ala Trp Ser His Pro
        595                 600                 605

Gln Phe Glu Lys Gly Gly Gly Ser Gly Gly Gly Ser Gly Gly Ser Ala
    610                 615                 620

Trp Ser His Pro Gln Phe Glu Lys
625                 630


<210> SEQ ID NO 5
<211> LENGTH: 954
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(954)

<400> SEQUENCE: 5

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg ggc gcg cct caa gtt cag ctt caa gaa tct       96
Thr Thr Ala Leu Ser Met Gly Ala Pro Gln Val Gln Leu Gln Glu Ser
            20                  25                  30

ggc ggc gga agc gtt cag gct ggc gga tct ctg aga ctg agc tgt gtg      144
Gly Gly Gly Ser Val Gln Ala Gly Gly Ser Leu Arg Leu Ser Cys Val
        35                  40                  45

gcc agc ggc tac acc gat agc aca tac tgc gtc ggc tgg ttc aga cag      192
Ala Ser Gly Tyr Thr Asp Ser Thr Tyr Cys Val Gly Trp Phe Arg Gln
    50                  55                  60

gcc cct ggc aaa gag aga gag ggc gtc gcc aga atc aac acc atc agc      240
Ala Pro Gly Lys Glu Arg Glu Gly Val Ala Arg Ile Asn Thr Ile Ser
65                  70                  75                  80

ggc aga cct tgg tac gcc gac tct gtg aag ggc aga ttc aca atc agc      288
Gly Arg Pro Trp Tyr Ala Asp Ser Val Lys Gly Arg Phe Thr Ile Ser
                85                  90                  95

cag gac aac agc aag aac acc gtg tac ctg cag atg aac agc ctg aag      336
```

-continued

```
Gln Asp Asn Ser Lys Asn Thr Val Tyr Leu Gln Met Asn Ser Leu Lys
            100                 105                 110

cct gag gac acc gcc atc tac tac tgc acc ctg acc acc gcc aac agc      384
Pro Glu Asp Thr Ala Ile Tyr Tyr Cys Thr Leu Thr Thr Ala Asn Ser
        115                 120                 125

aga ggc ttt tgt tcc ggc ggc tac aac tac aaa ggc cag ggc acc caa      432
Arg Gly Phe Cys Ser Gly Gly Tyr Asn Tyr Lys Gly Gln Gly Thr Gln
    130                 135                 140

gtg acc gtg tct ggt ggt acc agc gga ggc gga gga tca ggt ggc gga      480
Val Thr Val Ser Gly Gly Thr Ser Gly Gly Gly Gly Ser Gly Gly Gly
145                 150                 155                 160

ggt agt ggt ggt ggc ggt agc gcg gcc gcc caa gaa tgt agc ctg cag      528
Gly Ser Gly Gly Gly Gly Ser Ala Ala Ala Gln Glu Cys Ser Leu Gln
                165                 170                 175

agc tgc aca cag cac cag cct tac gtg gtg gac gac ccc tgt cct atc      576
Ser Cys Thr Gln His Gln Pro Tyr Val Val Asp Asp Pro Cys Pro Ile
            180                 185                 190

cac ttc tac agc aag tgg tac atc aga gtg ggc gcc aga aag agc gcc      624
His Phe Tyr Ser Lys Trp Tyr Ile Arg Val Gly Ala Arg Lys Ser Ala
        195                 200                 205

cca ctg att gag ctg tgt gtg gat gag gcc ggc agc aag agc ccc atc      672
Pro Leu Ile Glu Leu Cys Val Asp Glu Ala Gly Ser Lys Ser Pro Ile
    210                 215                 220

cag tac atc gac atc ggc aac tac acc gtg tcc tgc ctg cct ttc acc      720
Gln Tyr Ile Asp Ile Gly Asn Tyr Thr Val Ser Cys Leu Pro Phe Thr
225                 230                 235                 240

atc aac tgc caa gag cct aag ctg ggc tct ctg gtc gtg cgg tgc agc      768
Ile Asn Cys Gln Glu Pro Lys Leu Gly Ser Leu Val Val Arg Cys Ser
                245                 250                 255

ttc tac gag gac ttc ctg gaa tac cac gac gtg cgc gtg gtg ctg gat      816
Phe Tyr Glu Asp Phe Leu Glu Tyr His Asp Val Arg Val Val Leu Asp
            260                 265                 270

ttc atc ccg cgg ggt ggt ggt agt ggc gga gga agt ggt ggc gga tct      864
Phe Ile Pro Arg Gly Gly Gly Ser Gly Gly Gly Ser Gly Gly Gly Ser
        275                 280                 285

gct tgg agc cat cct cag ttc gag aaa ggc ggc ggt tca ggt ggt gga      912
Ala Trp Ser His Pro Gln Phe Glu Lys Gly Gly Gly Ser Gly Gly Gly
    290                 295                 300

tca ggc ggt tct gca tgg tca cac cca cag ttt gag aag tga              954
Ser Gly Gly Ser Ala Trp Ser His Pro Gln Phe Glu Lys
305                 310                 315


<210> SEQ ID NO 6
<211> LENGTH: 317
<212> TYPE: PRT
<213> ORGANISM: Artificial Sequence
<220> FEATURE:
<223> OTHER INFORMATION: Synthetic Construct

<400> SEQUENCE: 6

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80
```

```
Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125

Arg Gly Phe Cys Ser Gly Gly Tyr Asn Tyr Lys Gly Gln Gly Thr Gln
    130                 135                 140

Val Thr Val Ser Gly Gly Thr Ser Gly Gly Gly Gly Ser Gly Gly Gly
145                 150                 155                 160

Gly Ser Gly Gly Gly Gly Ser Ala Ala Ala Gln Glu Cys Ser Leu Gln
                165                 170                 175

Ser Cys Thr Gln His Gln Pro Tyr Val Val Asp Asp Pro Cys Pro Ile
            180                 185                 190

His Phe Tyr Ser Lys Trp Tyr Ile Arg Val Gly Ala Arg Lys Ser Ala
        195                 200                 205

Pro Leu Ile Glu Leu Cys Val Asp Glu Ala Gly Ser Lys Ser Pro Ile
    210                 215                 220

Gln Tyr Ile Asp Ile Gly Asn Tyr Thr Val Ser Cys Leu Pro Phe Thr
225                 230                 235                 240

Ile Asn Cys Gln Glu Pro Lys Leu Gly Ser Leu Val Val Arg Cys Ser
                245                 250                 255

Phe Tyr Glu Asp Phe Leu Glu Tyr His Asp Val Arg Val Val Leu Asp
            260                 265                 270

Phe Ile Pro Arg Gly Gly Gly Ser Gly Gly Gly Ser Gly Gly Gly Ser
        275                 280                 285

Ala Trp Ser His Pro Gln Phe Glu Lys Gly Gly Gly Ser Gly Gly Gly
    290                 295                 300

Ser Gly Gly Ser Ala Trp Ser His Pro Gln Phe Glu Lys
305                 310                 315
```

```
<210> SEQ ID NO 7
<211> LENGTH: 1635
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1635)

<400> SEQUENCE: 7

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg ggc gcg cct caa gtt cag ctt caa gaa tct       96
Thr Thr Ala Leu Ser Met Gly Ala Pro Gln Val Gln Leu Gln Glu Ser
            20                  25                  30

ggc ggc gga agc gtt cag gct ggc gga tct ctg aga ctg agc tgt gtg      144
Gly Gly Gly Ser Val Gln Ala Gly Gly Ser Leu Arg Leu Ser Cys Val
        35                  40                  45

gcc agc ggc tac acc gat agc aca tac tgc gtc ggc tgg ttc aga cag      192
Ala Ser Gly Tyr Thr Asp Ser Thr Tyr Cys Val Gly Trp Phe Arg Gln
    50                  55                  60

gcc cct ggc aaa gag aga gag ggc gtc gcc aga atc aac acc atc agc      240
Ala Pro Gly Lys Glu Arg Glu Gly Val Ala Arg Ile Asn Thr Ile Ser
65                  70                  75                  80
```

-continued

```
ggc aga cct tgg tac gcc gac tct gtg aag ggc aga ttc aca atc agc      288
Gly Arg Pro Trp Tyr Ala Asp Ser Val Lys Gly Arg Phe Thr Ile Ser
                85                  90                  95

cag gac aac agc aag aac acc gtg tac ctg cag atg aac agc ctg aag      336
Gln Asp Asn Ser Lys Asn Thr Val Tyr Leu Gln Met Asn Ser Leu Lys
            100                 105                 110

cct gag gac acc gcc atc tac tac tgc acc ctg acc acc gcc aac agc      384
Pro Glu Asp Thr Ala Ile Tyr Tyr Cys Thr Leu Thr Thr Ala Asn Ser
        115                 120                 125

aga ggc ttt tgt tcc ggc ggc tac aac tac aaa ggc cag ggc acc caa      432
Arg Gly Phe Cys Ser Gly Gly Tyr Asn Tyr Lys Gly Gln Gly Thr Gln
    130                 135                 140

gtg acc gtg tct ggt ggt acc agc gga ggc gga gga tca ggt ggc gga      480
Val Thr Val Ser Gly Gly Thr Ser Gly Gly Gly Gly Ser Gly Gly Gly
145                 150                 155                 160

ggt agt ggt ggt ggc ggt agc gcg gcc gct aga ttc ccc aac atc acc      528
Gly Ser Gly Gly Gly Gly Ser Ala Ala Ala Arg Phe Pro Asn Ile Thr
                165                 170                 175

aat ctg tgc ccc ttc ggc gag gtg ttc aac gcc aca aga ttc gcc tct      576
Asn Leu Cys Pro Phe Gly Glu Val Phe Asn Ala Thr Arg Phe Ala Ser
            180                 185                 190

gtg tac gcc tgg aac cgg aag cgg atc agc aat tgc gtg gcc gac tac      624
Val Tyr Ala Trp Asn Arg Lys Arg Ile Ser Asn Cys Val Ala Asp Tyr
        195                 200                 205

agc gtg ctg tac aac agc gcc agc ttc tcc acc ttc aag tgc tac ggc      672
Ser Val Leu Tyr Asn Ser Ala Ser Phe Ser Thr Phe Lys Cys Tyr Gly
    210                 215                 220

gtg tcc cct acc aag ctg aac gac ctg tgc ttt acc aac gtg tac gcc      720
Val Ser Pro Thr Lys Leu Asn Asp Leu Cys Phe Thr Asn Val Tyr Ala
225                 230                 235                 240

gat agc ttc gtg atc cgg gga gat gaa gtg cgg cag atc gct cct gga      768
Asp Ser Phe Val Ile Arg Gly Asp Glu Val Arg Gln Ile Ala Pro Gly
                245                 250                 255

cag aca ggc aag atc gcc gac tat aac tac aag ctg ccc gac gac ttc      816
Gln Thr Gly Lys Ile Ala Asp Tyr Asn Tyr Lys Leu Pro Asp Asp Phe
            260                 265                 270

acc ggc tgt gtg att gcc tgg aac agc aac aac ctg gac agc aaa gtc      864
Thr Gly Cys Val Ile Ala Trp Asn Ser Asn Asn Leu Asp Ser Lys Val
        275                 280                 285

ggc ggc aac tac aat tac ctg tac cgg ctg ttc cgg aag tcc aat ctg      912
Gly Gly Asn Tyr Asn Tyr Leu Tyr Arg Leu Phe Arg Lys Ser Asn Leu
    290                 295                 300

aag ccc ttc gag cgg gac atc agc acc gag atc tat cag gcc ggc agc      960
Lys Pro Phe Glu Arg Asp Ile Ser Thr Glu Ile Tyr Gln Ala Gly Ser
305                 310                 315                 320

acc cct tgc aat ggc gtg gaa ggc ttc aac tgc tac ttc cca ctg cag     1008
Thr Pro Cys Asn Gly Val Glu Gly Phe Asn Cys Tyr Phe Pro Leu Gln
                325                 330                 335

tcc tac ggc ttc cag cct aca aac ggc gtg ggc tac cag cct tac aga     1056
Ser Tyr Gly Phe Gln Pro Thr Asn Gly Val Gly Tyr Gln Pro Tyr Arg
            340                 345                 350

gtg gtg gtc ctg agc ttc gag ctg ctg cat gcc cct gct aca gtg tgc     1104
Val Val Val Leu Ser Phe Glu Leu Leu His Ala Pro Ala Thr Val Cys
        355                 360                 365

ggc cct aag aag tct acc aac ctg gaa ttc tct ggc ggc gga gga tct     1152
Gly Pro Lys Lys Ser Thr Asn Leu Glu Phe Ser Gly Gly Gly Gly Ser
    370                 375                 380

ggc gga ggt gga agc gga ggc ggt gga tct gcg gcc gcc caa gaa tgt     1200
Gly Gly Gly Gly Ser Gly Gly Gly Gly Ser Ala Ala Ala Gln Glu Cys
385                 390                 395                 400
```

```
agc ctg cag agc tgc aca cag cac cag cct tac gtg gtg gac gac ccc      1248
Ser Leu Gln Ser Cys Thr Gln His Gln Pro Tyr Val Val Asp Asp Pro
                405                 410                 415

tgt cct atc cac ttc tac agc aag tgg tac atc aga gtg ggc gcc aga      1296
Cys Pro Ile His Phe Tyr Ser Lys Trp Tyr Ile Arg Val Gly Ala Arg
            420                 425                 430

aag agc gcc cca ctg att gag ctg tgt gtg gat gag gcc ggc agc aag      1344
Lys Ser Ala Pro Leu Ile Glu Leu Cys Val Asp Glu Ala Gly Ser Lys
        435                 440                 445

agc ccc atc cag tac atc gac atc ggc aac tac acc gtg tcc tgc ctg      1392
Ser Pro Ile Gln Tyr Ile Asp Ile Gly Asn Tyr Thr Val Ser Cys Leu
    450                 455                 460

cct ttc acc atc aac tgc caa gag cct aag ctg ggc tct ctg gtc gtg      1440
Pro Phe Thr Ile Asn Cys Gln Glu Pro Lys Leu Gly Ser Leu Val Val
465                 470                 475                 480

cgg tgc agc ttc tac gag gac ttc ctg gaa tac cac gac gtg cgc gtg      1488
Arg Cys Ser Phe Tyr Glu Asp Phe Leu Glu Tyr His Asp Val Arg Val
                485                 490                 495

gtg ctg gat ttc atc ccg cgg ggt ggt ggt agt ggc gga gga agt ggt      1536
Val Leu Asp Phe Ile Pro Arg Gly Gly Gly Ser Gly Gly Gly Ser Gly
            500                 505                 510

ggc gga tct gct tgg agc cat cct cag ttc gag aaa ggc ggc ggt tca      1584
Gly Gly Ser Ala Trp Ser His Pro Gln Phe Glu Lys Gly Gly Gly Ser
        515                 520                 525

ggt ggt gga tca ggc ggt tct gca tgg tca cac cca cag ttt gag aag      1632
Gly Gly Gly Ser Gly Gly Ser Ala Trp Ser His Pro Gln Phe Glu Lys
    530                 535                 540

tga                                                                  1635


<210> SEQ ID NO 8
<211> LENGTH: 544
<212> TYPE: PRT
<213> ORGANISM: Artificial Sequence
<220> FEATURE:
<223> OTHER INFORMATION: Synthetic Construct

<400> SEQUENCE: 8

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80

Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125

Arg Gly Phe Cys Ser Gly Gly Tyr Asn Tyr Lys Gly Gln Gly Thr Gln
    130                 135                 140

Val Thr Val Ser Gly Gly Thr Ser Gly Gly Gly Gly Ser Gly Gly Gly
145                 150                 155                 160
```

-continued

```
Gly Ser Gly Gly Gly Gly Ser Ala Ala Ala Arg Phe Pro Asn Ile Thr
                165                 170                 175

Asn Leu Cys Pro Phe Gly Glu Val Phe Asn Ala Thr Arg Phe Ala Ser
            180                 185                 190

Val Tyr Ala Trp Asn Arg Lys Arg Ile Ser Asn Cys Val Ala Asp Tyr
        195                 200                 205

Ser Val Leu Tyr Asn Ser Ala Ser Phe Ser Thr Phe Lys Cys Tyr Gly
    210                 215                 220

Val Ser Pro Thr Lys Leu Asn Asp Leu Cys Phe Thr Asn Val Tyr Ala
225                 230                 235                 240

Asp Ser Phe Val Ile Arg Gly Asp Glu Val Arg Gln Ile Ala Pro Gly
                245                 250                 255

Gln Thr Gly Lys Ile Ala Asp Tyr Asn Tyr Lys Leu Pro Asp Asp Phe
            260                 265                 270

Thr Gly Cys Val Ile Ala Trp Asn Ser Asn Asn Leu Asp Ser Lys Val
        275                 280                 285

Gly Gly Asn Tyr Asn Tyr Leu Tyr Arg Leu Phe Arg Lys Ser Asn Leu
    290                 295                 300

Lys Pro Phe Glu Arg Asp Ile Ser Thr Glu Ile Tyr Gln Ala Gly Ser
305                 310                 315                 320

Thr Pro Cys Asn Gly Val Glu Gly Phe Asn Cys Tyr Phe Pro Leu Gln
                325                 330                 335

Ser Tyr Gly Phe Gln Pro Thr Asn Gly Val Gly Tyr Gln Pro Tyr Arg
            340                 345                 350

Val Val Val Leu Ser Phe Glu Leu Leu His Ala Pro Ala Thr Val Cys
        355                 360                 365

Gly Pro Lys Lys Ser Thr Asn Leu Glu Phe Ser Gly Gly Gly Gly Ser
    370                 375                 380

Gly Gly Gly Gly Ser Gly Gly Gly Gly Ser Ala Ala Ala Gln Glu Cys
385                 390                 395                 400

Ser Leu Gln Ser Cys Thr Gln His Gln Pro Tyr Val Val Asp Asp Pro
                405                 410                 415

Cys Pro Ile His Phe Tyr Ser Lys Trp Tyr Ile Arg Val Gly Ala Arg
            420                 425                 430

Lys Ser Ala Pro Leu Ile Glu Leu Cys Val Asp Glu Ala Gly Ser Lys
        435                 440                 445

Ser Pro Ile Gln Tyr Ile Asp Ile Gly Asn Tyr Thr Val Ser Cys Leu
    450                 455                 460

Pro Phe Thr Ile Asn Cys Gln Glu Pro Lys Leu Gly Ser Leu Val Val
465                 470                 475                 480

Arg Cys Ser Phe Tyr Glu Asp Phe Leu Glu Tyr His Asp Val Arg Val
                485                 490                 495

Val Leu Asp Phe Ile Pro Arg Gly Gly Gly Ser Gly Gly Gly Ser Gly
            500                 505                 510

Gly Gly Ser Ala Trp Ser His Pro Gln Phe Glu Lys Gly Gly Gly Ser
        515                 520                 525

Gly Gly Gly Ser Gly Gly Ser Ala Trp Ser His Pro Gln Phe Glu Lys
    530                 535                 540
```

<210> SEQ ID NO 9
<211> LENGTH: 810
<212> TYPE: DNA
<213> ORGANISM: Artificial Sequence
<220> FEATURE:
<223> OTHER INFORMATION: Synthetic

```
<220> FEATURE:
<221> NAME/KEY: CDS
<222> LOCATION: (1)..(810)

<400> SEQUENCE: 9

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg ggc gcg cct caa gtt cag ctt caa gaa tct       96
Thr Thr Ala Leu Ser Met Gly Ala Pro Gln Val Gln Leu Gln Glu Ser
            20                  25                  30

ggc ggc gga agc gtt cag gct ggc gga tct ctg aga ctg agc tgt gtg      144
Gly Gly Gly Ser Val Gln Ala Gly Gly Ser Leu Arg Leu Ser Cys Val
        35                  40                  45

gcc agc ggc tac acc gat agc aca tac tgc gtc ggc tgg ttc aga cag      192
Ala Ser Gly Tyr Thr Asp Ser Thr Tyr Cys Val Gly Trp Phe Arg Gln
    50                  55                  60

gcc cct ggc aaa gag aga gag ggc gtc gcc aga atc aac acc atc agc      240
Ala Pro Gly Lys Glu Arg Glu Gly Val Ala Arg Ile Asn Thr Ile Ser
65                  70                  75                  80

ggc aga cct tgg tac gcc gac tct gtg aag ggc aga ttc aca atc agc      288
Gly Arg Pro Trp Tyr Ala Asp Ser Val Lys Gly Arg Phe Thr Ile Ser
                85                  90                  95

cag gac aac agc aag aac acc gtg tac ctg cag atg aac agc ctg aag      336
Gln Asp Asn Ser Lys Asn Thr Val Tyr Leu Gln Met Asn Ser Leu Lys
            100                 105                 110

cct gag gac acc gcc atc tac tac tgc acc ctg acc acc gcc aac agc      384
Pro Glu Asp Thr Ala Ile Tyr Tyr Cys Thr Leu Thr Thr Ala Asn Ser
        115                 120                 125

aga ggc ttt tgt tcc ggc ggc tac aac tac aaa ggc cag ggc acc caa      432
Arg Gly Phe Cys Ser Gly Gly Tyr Asn Tyr Lys Gly Gln Gly Thr Gln
    130                 135                 140

gtg acc gtg tct ggt ggt acc agc gga ggc gga gga tca ggt ggc gga      480
Val Thr Val Ser Gly Gly Thr Ser Gly Gly Gly Gly Ser Gly Gly Gly
145                 150                 155                 160

ggt agt ggt ggt ggc ggt agc gcg gcc gct atg gcc tac tgt tgg aga      528
Gly Ser Gly Gly Gly Gly Ser Ala Ala Ala Met Ala Tyr Cys Trp Arg
                165                 170                 175

tgc acc agc tgc tgc ttc agc gag cgg ttc cag aac cac aat cct cag      576
Cys Thr Ser Cys Cys Phe Ser Glu Arg Phe Gln Asn His Asn Pro Gln
            180                 185                 190

aaa gag atg gcc acc agc aca ctg cag ggc tgt tct ctg tgt ctg cag      624
Lys Glu Met Ala Thr Ser Thr Leu Gln Gly Cys Ser Leu Cys Leu Gln
        195                 200                 205

ctg gcc gtg gtg gtc aac tct ctg ctg acc cct ttc gcc aga tgc tgc      672
Leu Ala Val Val Val Asn Ser Leu Leu Thr Pro Phe Ala Arg Cys Cys
    210                 215                 220

tgg cct gaa ttc ggc gga ggc agc ggc ggt gga agc ggc gga ggc tct      720
Trp Pro Glu Phe Gly Gly Gly Ser Gly Gly Gly Ser Gly Gly Gly Ser
225                 230                 235                 240

gct tgg agc cac ccg cag ttc gaa aaa ggt gga ggt tct ggc ggt gga      768
Ala Trp Ser His Pro Gln Phe Glu Lys Gly Gly Gly Ser Gly Gly Gly
                245                 250                 255

tcg gga ggt tca gcg tgg agc cac ccg cag ttc gag aaa tga              810
Ser Gly Gly Ser Ala Trp Ser His Pro Gln Phe Glu Lys
            260                 265


<210> SEQ ID NO 10
<211> LENGTH: 269
<212> TYPE: PRT
<213> ORGANISM: Artificial Sequence
```

```
<220> FEATURE:
<223> OTHER INFORMATION: Synthetic Construct

<400> SEQUENCE: 10

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80

Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125

Arg Gly Phe Cys Ser Gly Gly Tyr Asn Tyr Lys Gly Gln Gly Thr Gln
    130                 135                 140

Val Thr Val Ser Gly Gly Thr Ser Gly Gly Gly Gly Ser Gly Gly Gly
145                 150                 155                 160

Gly Ser Gly Gly Gly Gly Ser Ala Ala Ala Met Ala Tyr Cys Trp Arg
                165                 170                 175

Cys Thr Ser Cys Cys Phe Ser Glu Arg Phe Gln Asn His Asn Pro Gln
            180                 185                 190

Lys Glu Met Ala Thr Ser Thr Leu Gln Gly Cys Ser Leu Cys Leu Gln
        195                 200                 205

Leu Ala Val Val Val Asn Ser Leu Leu Thr Pro Phe Ala Arg Cys Cys
    210                 215                 220

Trp Pro Glu Phe Gly Gly Gly Ser Gly Gly Gly Ser Gly Gly Gly Ser
225                 230                 235                 240

Ala Trp Ser His Pro Gln Phe Glu Lys Gly Gly Gly Ser Gly Gly Gly
                245                 250                 255

Ser Gly Gly Ser Ala Trp Ser His Pro Gln Phe Glu Lys
            260                 265


<210> SEQ ID NO 11
<211> LENGTH: 1491
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1491)

<400> SEQUENCE: 11

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg ggc gcg cct caa gtt cag ctt caa gaa tct       96
Thr Thr Ala Leu Ser Met Gly Ala Pro Gln Val Gln Leu Gln Glu Ser
            20                  25                  30

ggc ggc gga agc gtt cag gct ggc gga tct ctg aga ctg agc tgt gtg      144
Gly Gly Gly Ser Val Gln Ala Gly Gly Ser Leu Arg Leu Ser Cys Val
```

-continued

```
        35                  40                  45

gcc agc ggc tac acc gat agc aca tac tgc gtc ggc tgg ttc aga cag      192
Ala Ser Gly Tyr Thr Asp Ser Thr Tyr Cys Val Gly Trp Phe Arg Gln
    50                  55                  60

gcc cct ggc aaa gag aga gag ggc gtc gcc aga atc aac acc atc agc      240
Ala Pro Gly Lys Glu Arg Glu Gly Val Ala Arg Ile Asn Thr Ile Ser
65                  70                  75                  80

ggc aga cct tgg tac gcc gac tct gtg aag ggc aga ttc aca atc agc      288
Gly Arg Pro Trp Tyr Ala Asp Ser Val Lys Gly Arg Phe Thr Ile Ser
                85                  90                  95

cag gac aac agc aag aac acc gtg tac ctg cag atg aac agc ctg aag      336
Gln Asp Asn Ser Lys Asn Thr Val Tyr Leu Gln Met Asn Ser Leu Lys
            100                 105                 110

cct gag gac acc gcc atc tac tac tgc acc ctg acc acc gcc aac agc      384
Pro Glu Asp Thr Ala Ile Tyr Tyr Cys Thr Leu Thr Thr Ala Asn Ser
        115                 120                 125

aga ggc ttt tgt tcc ggc ggc tac aac tac aaa ggc cag ggc acc caa      432
Arg Gly Phe Cys Ser Gly Gly Tyr Asn Tyr Lys Gly Gln Gly Thr Gln
    130                 135                 140

gtg acc gtg tct ggt ggt acc agc gga ggc gga gga tca ggt ggc gga      480
Val Thr Val Ser Gly Gly Thr Ser Gly Gly Gly Gly Ser Gly Gly Gly
145                 150                 155                 160

ggt agt ggt ggt ggc ggt agc gcg gcc gct aga ttc ccc aac atc acc      528
Gly Ser Gly Gly Gly Gly Ser Ala Ala Ala Arg Phe Pro Asn Ile Thr
                165                 170                 175

aat ctg tgc ccc ttc ggc gag gtg ttc aac gcc aca aga ttc gcc tct      576
Asn Leu Cys Pro Phe Gly Glu Val Phe Asn Ala Thr Arg Phe Ala Ser
            180                 185                 190

gtg tac gcc tgg aac cgg aag cgg atc agc aat tgc gtg gcc gac tac      624
Val Tyr Ala Trp Asn Arg Lys Arg Ile Ser Asn Cys Val Ala Asp Tyr
        195                 200                 205

agc gtg ctg tac aac agc gcc agc ttc tcc acc ttc aag tgc tac ggc      672
Ser Val Leu Tyr Asn Ser Ala Ser Phe Ser Thr Phe Lys Cys Tyr Gly
    210                 215                 220

gtg tcc cct acc aag ctg aac gac ctg tgc ttt acc aac gtg tac gcc      720
Val Ser Pro Thr Lys Leu Asn Asp Leu Cys Phe Thr Asn Val Tyr Ala
225                 230                 235                 240

gat agc ttc gtg atc cgg gga gat gaa gtg cgg cag atc gct cct gga      768
Asp Ser Phe Val Ile Arg Gly Asp Glu Val Arg Gln Ile Ala Pro Gly
                245                 250                 255

cag aca ggc aag atc gcc gac tat aac tac aag ctg ccc gac gac ttc      816
Gln Thr Gly Lys Ile Ala Asp Tyr Asn Tyr Lys Leu Pro Asp Asp Phe
            260                 265                 270

acc ggc tgt gtg att gcc tgg aac agc aac aac ctg gac agc aaa gtc      864
Thr Gly Cys Val Ile Ala Trp Asn Ser Asn Asn Leu Asp Ser Lys Val
        275                 280                 285

ggc ggc aac tac aat tac ctg tac cgg ctg ttc cgg aag tcc aat ctg      912
Gly Gly Asn Tyr Asn Tyr Leu Tyr Arg Leu Phe Arg Lys Ser Asn Leu
    290                 295                 300

aag ccc ttc gag cgg gac atc agc acc gag atc tat cag gcc ggc agc      960
Lys Pro Phe Glu Arg Asp Ile Ser Thr Glu Ile Tyr Gln Ala Gly Ser
305                 310                 315                 320

acc cct tgc aat ggc gtg gaa ggc ttc aac tgc tac ttc cca ctg cag     1008
Thr Pro Cys Asn Gly Val Glu Gly Phe Asn Cys Tyr Phe Pro Leu Gln
                325                 330                 335

tcc tac ggc ttc cag cct aca aac ggc gtg ggc tac cag cct tac aga     1056
Ser Tyr Gly Phe Gln Pro Thr Asn Gly Val Gly Tyr Gln Pro Tyr Arg
            340                 345                 350

gtg gtg gtc ctg agc ttc gag ctg ctg cat gcc cct gct aca gtg tgc     1104
```

-continued

```
Val Val Val Leu Ser Phe Glu Leu Leu His Ala Pro Ala Thr Val Cys
        355                 360                 365

ggc cct aag aag tct acc aac ctg gaa ttc tct ggc ggc gga gga tct     1152
Gly Pro Lys Lys Ser Thr Asn Leu Glu Phe Ser Gly Gly Gly Gly Ser
    370                 375                 380

ggc gga ggt gga agc gga ggc ggt gga tct gcg gcc gct atg gcc tac     1200
Gly Gly Gly Gly Ser Gly Gly Gly Gly Ser Ala Ala Ala Met Ala Tyr
385                 390                 395                 400

tgt tgg aga tgc acc agc tgc tgc ttc agc gag cgg ttc cag aac cac     1248
Cys Trp Arg Cys Thr Ser Cys Cys Phe Ser Glu Arg Phe Gln Asn His
            405                 410                 415

aat cct cag aaa gag atg gcc acc agc aca ctg cag ggc tgt tct ctg     1296
Asn Pro Gln Lys Glu Met Ala Thr Ser Thr Leu Gln Gly Cys Ser Leu
            420                 425                 430

tgt ctg cag ctg gcc gtg gtg gtc aac tct ctg ctg acc cct ttc gcc     1344
Cys Leu Gln Leu Ala Val Val Val Asn Ser Leu Leu Thr Pro Phe Ala
        435                 440                 445

aga tgc tgc tgg cct gaa ttc ggc gga ggc agc ggc ggt gga agc ggc     1392
Arg Cys Cys Trp Pro Glu Phe Gly Gly Gly Ser Gly Gly Gly Ser Gly
    450                 455                 460

gga ggc tct gct tgg agc cac ccg cag ttc gaa aaa ggt gga ggt tct     1440
Gly Gly Ser Ala Trp Ser His Pro Gln Phe Glu Lys Gly Gly Gly Ser
465                 470                 475                 480

ggc ggt gga tcg gga ggt tca gcg tgg agc cac ccg cag ttc gag aaa     1488
Gly Gly Gly Ser Gly Gly Ser Ala Trp Ser His Pro Gln Phe Glu Lys
                485                 490                 495

tga                                                                 1491


<210> SEQ ID NO 12
<211> LENGTH: 496
<212> TYPE: PRT
<213> ORGANISM: Artificial Sequence
<220> FEATURE:
<223> OTHER INFORMATION: Synthetic Construct

<400> SEQUENCE: 12

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80

Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125

Arg Gly Phe Cys Ser Gly Gly Tyr Asn Tyr Lys Gly Gln Gly Thr Gln
    130                 135                 140

Val Thr Val Ser Gly Gly Thr Ser Gly Gly Gly Gly Ser Gly Gly Gly
145                 150                 155                 160

Gly Ser Gly Gly Gly Gly Ser Ala Ala Ala Arg Phe Pro Asn Ile Thr
                165                 170                 175
```

```
Asn Leu Cys Pro Phe Gly Glu Val Phe Asn Ala Thr Arg Phe Ala Ser
            180                 185                 190

Val Tyr Ala Trp Asn Arg Lys Arg Ile Ser Asn Cys Val Ala Asp Tyr
        195                 200                 205

Ser Val Leu Tyr Asn Ser Ala Ser Phe Ser Thr Phe Lys Cys Tyr Gly
    210                 215                 220

Val Ser Pro Thr Lys Leu Asn Asp Leu Cys Phe Thr Asn Val Tyr Ala
225                 230                 235                 240

Asp Ser Phe Val Ile Arg Gly Asp Glu Val Arg Gln Ile Ala Pro Gly
                245                 250                 255

Gln Thr Gly Lys Ile Ala Asp Tyr Asn Tyr Lys Leu Pro Asp Asp Phe
            260                 265                 270

Thr Gly Cys Val Ile Ala Trp Asn Ser Asn Asn Leu Asp Ser Lys Val
        275                 280                 285

Gly Gly Asn Tyr Asn Tyr Leu Tyr Arg Leu Phe Arg Lys Ser Asn Leu
    290                 295                 300

Lys Pro Phe Glu Arg Asp Ile Ser Thr Glu Ile Tyr Gln Ala Gly Ser
305                 310                 315                 320

Thr Pro Cys Asn Gly Val Glu Gly Phe Asn Cys Tyr Phe Pro Leu Gln
                325                 330                 335

Ser Tyr Gly Phe Gln Pro Thr Asn Gly Val Gly Tyr Gln Pro Tyr Arg
            340                 345                 350

Val Val Val Leu Ser Phe Glu Leu Leu His Ala Pro Ala Thr Val Cys
        355                 360                 365

Gly Pro Lys Lys Ser Thr Asn Leu Glu Phe Ser Gly Gly Gly Gly Ser
    370                 375                 380

Gly Gly Gly Gly Ser Gly Gly Gly Gly Ser Ala Ala Ala Met Ala Tyr
385                 390                 395                 400

Cys Trp Arg Cys Thr Ser Cys Cys Phe Ser Glu Arg Phe Gln Asn His
                405                 410                 415

Asn Pro Gln Lys Glu Met Ala Thr Ser Thr Leu Gln Gly Cys Ser Leu
            420                 425                 430

Cys Leu Gln Leu Ala Val Val Val Asn Ser Leu Leu Thr Pro Phe Ala
        435                 440                 445

Arg Cys Cys Trp Pro Glu Phe Gly Gly Gly Ser Gly Gly Gly Ser Gly
    450                 455                 460

Gly Gly Ser Ala Trp Ser His Pro Gln Phe Glu Lys Gly Gly Gly Ser
465                 470                 475                 480

Gly Gly Gly Ser Gly Gly Ser Ala Trp Ser His Pro Gln Phe Glu Lys
                485                 490                 495


<210> SEQ ID NO 13
<211> LENGTH: 579
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(579)

<400> SEQUENCE: 13

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg ggc gcg cct caa gtt cag ctt caa gaa tct       96
```

```
Thr Thr Ala Leu Ser Met Gly Ala Pro Gln Val Gln Leu Gln Glu Ser
            20                  25                  30

ggc ggc gga agc gtt cag gct ggc gga tct ctg aga ctg agc tgt gtg      144
Gly Gly Gly Ser Val Gln Ala Gly Gly Ser Leu Arg Leu Ser Cys Val
        35                  40                  45

gcc agc ggc tac acc gat agc aca tac tgc gtc ggc tgg ttc aga cag      192
Ala Ser Gly Tyr Thr Asp Ser Thr Tyr Cys Val Gly Trp Phe Arg Gln
    50                  55                  60

gcc cct ggc aaa gag aga gag ggc gtc gcc aga atc aac acc atc agc      240
Ala Pro Gly Lys Glu Arg Glu Gly Val Ala Arg Ile Asn Thr Ile Ser
65                  70                  75                  80

ggc aga cct tgg tac gcc gac tct gtg aag ggc aga ttc aca atc agc      288
Gly Arg Pro Trp Tyr Ala Asp Ser Val Lys Gly Arg Phe Thr Ile Ser
                85                  90                  95

cag gac aac agc aag aac acc gtg tac ctg cag atg aac agc ctg aag      336
Gln Asp Asn Ser Lys Asn Thr Val Tyr Leu Gln Met Asn Ser Leu Lys
            100                 105                 110

cct gag gac acc gcc atc tac tac tgc acc ctg acc acc gcc aac agc      384
Pro Glu Asp Thr Ala Ile Tyr Tyr Cys Thr Leu Thr Thr Ala Asn Ser
        115                 120                 125

aga ggc ttt tgt tcc ggc ggc tac aac tac aaa ggc cag ggc acc caa      432
Arg Gly Phe Cys Ser Gly Gly Tyr Asn Tyr Lys Gly Gln Gly Thr Gln
    130                 135                 140

gtg acc gtg tct ggt gaa ttc ggc gga ggc agc ggc ggt gga agc ggc      480
Val Thr Val Ser Gly Glu Phe Gly Gly Gly Ser Gly Gly Gly Ser Gly
145                 150                 155                 160

gga ggc tct gct tgg agc cac ccg cag ttc gaa aaa ggt gga ggt tct      528
Gly Gly Ser Ala Trp Ser His Pro Gln Phe Glu Lys Gly Gly Gly Ser
                165                 170                 175

ggc ggt gga tcg gga ggt tca gcg tgg agc cac ccg cag ttc gag aaa      576
Gly Gly Gly Ser Gly Gly Ser Ala Trp Ser His Pro Gln Phe Glu Lys
            180                 185                 190

tga                                                                  579


<210> SEQ ID NO 14
<211> LENGTH: 192
<212> TYPE: PRT
<213> ORGANISM: Artificial Sequence
<220> FEATURE:
<223> OTHER INFORMATION: Synthetic Construct

<400> SEQUENCE: 14

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Gln Glu Ser
            20                  25                  30

Gly Gly Gly Ser Val Gln Ala Gly Gly Ser Leu Arg Leu Ser Cys Val
        35                  40                  45

Ala Ser Gly Tyr Thr Asp Ser Thr Tyr Cys Val Gly Trp Phe Arg Gln
    50                  55                  60

Ala Pro Gly Lys Glu Arg Glu Gly Val Ala Arg Ile Asn Thr Ile Ser
65                  70                  75                  80

Gly Arg Pro Trp Tyr Ala Asp Ser Val Lys Gly Arg Phe Thr Ile Ser
                85                  90                  95

Gln Asp Asn Ser Lys Asn Thr Val Tyr Leu Gln Met Asn Ser Leu Lys
            100                 105                 110

Pro Glu Asp Thr Ala Ile Tyr Tyr Cys Thr Leu Thr Thr Ala Asn Ser
        115                 120                 125
```

```
Arg Gly Phe Cys Ser Gly Gly Tyr Asn Tyr Lys Gly Gln Gly Thr Gln
    130                 135                 140

Val Thr Val Ser Gly Glu Phe Gly Gly Gly Ser Gly Gly Gly Ser Gly
145                 150                 155                 160

Gly Gly Ser Ala Trp Ser His Pro Gln Phe Glu Lys Gly Gly Gly Ser
                165                 170                 175

Gly Gly Gly Ser Gly Gly Ser Ala Trp Ser His Pro Gln Phe Glu Lys
            180                 185                 190


<210> SEQ ID NO 15
<211> LENGTH: 1776
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1776)

<400> SEQUENCE: 15

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg ggc gcg cct cag gtt cag ctg gtt gaa tct       96
Thr Thr Ala Leu Ser Met Gly Ala Pro Gln Val Gln Leu Val Glu Ser
            20                  25                  30

ggc gga ggc ctg atg caa gct ggc gga tct ctg aga ctg agc tgt gcc      144
Gly Gly Gly Leu Met Gln Ala Gly Gly Ser Leu Arg Leu Ser Cys Ala
        35                  40                  45

gtg tcc ggc aga acc ttt tct aca gcc gcc atg ggc tgg ttc aga cag      192
Val Ser Gly Arg Thr Phe Ser Thr Ala Ala Met Gly Trp Phe Arg Gln
    50                  55                  60

gcc cct gga aaa gaa cgc gag ttc gtg gcc gct atc cgt tgg agc gga      240
Ala Pro Gly Lys Glu Arg Glu Phe Val Ala Ala Ile Arg Trp Ser Gly
65                  70                  75                  80

ggc tct gcc tac tac gcc gat tct gtg aag ggc aga ttc acc atc agc      288
Gly Ser Ala Tyr Tyr Ala Asp Ser Val Lys Gly Arg Phe Thr Ile Ser
                85                  90                  95

aga gac aag gcc aag aac acc gtg tac ctg cag atg aac agc ctg aag      336
Arg Asp Lys Ala Lys Asn Thr Val Tyr Leu Gln Met Asn Ser Leu Lys
            100                 105                 110

tac gag gac acc gcc gtg tac tac tgc gcc aga aca gag aat gtg cgg      384
Tyr Glu Asp Thr Ala Val Tyr Tyr Cys Ala Arg Thr Glu Asn Val Arg
        115                 120                 125

agc ctg ctg agc gac tac gcc acc tgg cct tac gat tat tgg ggc cag      432
Ser Leu Leu Ser Asp Tyr Ala Thr Trp Pro Tyr Asp Tyr Trp Gly Gln
    130                 135                 140

ggc acc caa gtg acc gtt tct ggt ggc gga gga agc gga ggc gga gga      480
Gly Thr Gln Val Thr Val Ser Gly Gly Gly Gly Ser Gly Gly Gly Gly
145                 150                 155                 160

tca ggt ggc ggt gga tct atc gat cag gtg cag ctc gtg gaa agc ggt      528
Ser Gly Gly Gly Gly Ser Ile Asp Gln Val Gln Leu Val Glu Ser Gly
                165                 170                 175

ggc gga ctt atg cag gca ggc gga agc ctg aga ctg tct tgt gct gtg      576
Gly Gly Leu Met Gln Ala Gly Gly Ser Leu Arg Leu Ser Cys Ala Val
            180                 185                 190

tct ggc cgg acc ttt agc acc gct gct atg gga tgg ttt agg cag gct      624
Ser Gly Arg Thr Phe Ser Thr Ala Ala Met Gly Trp Phe Arg Gln Ala
        195                 200                 205

cca ggc aaa gaa agg gaa ttt gtg gcc gcc att cgt tgg agt ggc ggc      672
Pro Gly Lys Glu Arg Glu Phe Val Ala Ala Ile Arg Trp Ser Gly Gly
```

```
    210                 215                 220

agc gcc tat tat gcc gat agc gtg aaa ggc cgg ttc acc atc tct cgc      720
Ser Ala Tyr Tyr Ala Asp Ser Val Lys Gly Arg Phe Thr Ile Ser Arg
225                 230                 235                 240

gat aag gct aag aat acg gtc tat ctc cag atg aac tcc ctc aaa tat      768
Asp Lys Ala Lys Asn Thr Val Tyr Leu Gln Met Asn Ser Leu Lys Tyr
                245                 250                 255

gag gat acg gcc gtc tac tat tgt gcc cgg acc gaa aat gtg cgc tcc      816
Glu Asp Thr Ala Val Tyr Tyr Cys Ala Arg Thr Glu Asn Val Arg Ser
            260                 265                 270

ctg ctg tct gat tat gcc aca tgg ccc tat gac tac tgg gga cag gga      864
Leu Leu Ser Asp Tyr Ala Thr Trp Pro Tyr Asp Tyr Trp Gly Gln Gly
        275                 280                 285

aca caa gtc aca gtg tcc agc ggt acc ggc gga ggt gga agc gga ggc      912
Thr Gln Val Thr Val Ser Ser Gly Thr Gly Gly Gly Gly Ser Gly Gly
    290                 295                 300

gga ggc tct ggc ggc ggt gga tct gga tcc gag cct aag agc tgc gac      960
Gly Gly Ser Gly Gly Gly Gly Ser Gly Ser Glu Pro Lys Ser Cys Asp
305                 310                 315                 320

aag acc cac acc tgt cct cca tgt cct gct cca gaa ctg ctc ggc gga     1008
Lys Thr His Thr Cys Pro Pro Cys Pro Ala Pro Glu Leu Leu Gly Gly
                325                 330                 335

cct tcc gtg ttc ctg ttt cct cca aag cct aag gac acc ctg atg atc     1056
Pro Ser Val Phe Leu Phe Pro Pro Lys Pro Lys Asp Thr Leu Met Ile
            340                 345                 350

agc aga acc cct gaa gtg acc tgc gtg gtg gtg gat gtg tcc cac gaa     1104
Ser Arg Thr Pro Glu Val Thr Cys Val Val Val Asp Val Ser His Glu
        355                 360                 365

gat ccc gaa gtg aag ttc aat tgg tac gtg gac ggc gtg gaa gtg cac     1152
Asp Pro Glu Val Lys Phe Asn Trp Tyr Val Asp Gly Val Glu Val His
    370                 375                 380

aac gcc aag acc aag cct aga gag gaa cag tac aac agc acc tac aga     1200
Asn Ala Lys Thr Lys Pro Arg Glu Glu Gln Tyr Asn Ser Thr Tyr Arg
385                 390                 395                 400

gtg gtg tcc gtg ctg acc gtg ctg cac cag gat tgg ctg aac ggc aaa     1248
Val Val Ser Val Leu Thr Val Leu His Gln Asp Trp Leu Asn Gly Lys
                405                 410                 415

gag tac aag tgc aag gtg tcc aac aag gcc ctg cct gct cct atc gag     1296
Glu Tyr Lys Cys Lys Val Ser Asn Lys Ala Leu Pro Ala Pro Ile Glu
            420                 425                 430

aaa acc atc agc aag gcc aag ggc cag cct agg gaa ccc cag gtt tac     1344
Lys Thr Ile Ser Lys Ala Lys Gly Gln Pro Arg Glu Pro Gln Val Tyr
        435                 440                 445

aca ctg cct cca agc cgg gaa gag atg acc aag aac cag gtg tcc ctg     1392
Thr Leu Pro Pro Ser Arg Glu Glu Met Thr Lys Asn Gln Val Ser Leu
    450                 455                 460

acc tgc ctg gtc aag ggc ttc tac cct tcc gat atc gcc gtg gaa tgg     1440
Thr Cys Leu Val Lys Gly Phe Tyr Pro Ser Asp Ile Ala Val Glu Trp
465                 470                 475                 480

gag agc aat ggc cag cct gag aac aac tac aag aca acc cct cct gtg     1488
Glu Ser Asn Gly Gln Pro Glu Asn Asn Tyr Lys Thr Thr Pro Pro Val
                485                 490                 495

ctg gac agc gac ggc tca ttc ttc ctg tat agc aag ctg aca gtg gac     1536
Leu Asp Ser Asp Gly Ser Phe Phe Leu Tyr Ser Lys Leu Thr Val Asp
            500                 505                 510

aag agc aga tgg cag cag ggc aac gtg ttc agc tgc agc gtg atg cac     1584
Lys Ser Arg Trp Gln Gln Gly Asn Val Phe Ser Cys Ser Val Met His
        515                 520                 525

gag gcc ctg cac aac cac tac acc cag aag tcc ctg agc ctg tct cct     1632
```

-continued

```
Glu Ala Leu His Asn His Tyr Thr Gln Lys Ser Leu Ser Leu Ser Pro
    530                 535                 540

ggc aag ccg cgg ggt ggt ggt tcc ggc gga ggt agt ggc ggc gga tct      1680
Gly Lys Pro Arg Gly Gly Gly Ser Gly Gly Gly Ser Gly Gly Gly Ser
545                 550                 555                 560

gcg gcc gct tgg agc cat cct cag ttc gag aaa ggc gga gga agc ggc      1728
Ala Ala Ala Trp Ser His Pro Gln Phe Glu Lys Gly Gly Gly Ser Gly
                565                 570                 575

gga ggc agc ggt ggt ggc tct tgg tca cat ccc cag ttt gag aag tga      1776
Gly Gly Ser Gly Gly Gly Ser Trp Ser His Pro Gln Phe Glu Lys
            580                 585                 590


<210> SEQ ID NO 16
<211> LENGTH: 591
<212> TYPE: PRT
<213> ORGANISM: Artificial Sequence
<220> FEATURE:
<223> OTHER INFORMATION: Synthetic Construct

<400> SEQUENCE: 16

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Val Glu Ser
            20                  25                  30

Gly Gly Gly Leu Met Gln Ala Gly Gly Ser Leu Arg Leu Ser Cys Ala
        35                  40                  45

Val Ser Gly Arg Thr Phe Ser Thr Ala Ala Met Gly Trp Phe Arg Gln
    50                  55                  60

Ala Pro Gly Lys Glu Arg Glu Phe Val Ala Ala Ile Arg Trp Ser Gly
65                  70                  75                  80

Gly Ser Ala Tyr Tyr Ala Asp Ser Val Lys Gly Arg Phe Thr Ile Ser
                85                  90                  95

Arg Asp Lys Ala Lys Asn Thr Val Tyr Leu Gln Met Asn Ser Leu Lys
            100                 105                 110

Tyr Glu Asp Thr Ala Val Tyr Tyr Cys Ala Arg Thr Glu Asn Val Arg
        115                 120                 125

Ser Leu Leu Ser Asp Tyr Ala Thr Trp Pro Tyr Asp Tyr Trp Gly Gln
    130                 135                 140

Gly Thr Gln Val Thr Val Ser Gly Gly Gly Gly Ser Gly Gly Gly Gly
145                 150                 155                 160

Ser Gly Gly Gly Gly Ser Ile Asp Gln Val Gln Leu Val Glu Ser Gly
                165                 170                 175

Gly Gly Leu Met Gln Ala Gly Gly Ser Leu Arg Leu Ser Cys Ala Val
            180                 185                 190

Ser Gly Arg Thr Phe Ser Thr Ala Ala Met Gly Trp Phe Arg Gln Ala
        195                 200                 205

Pro Gly Lys Glu Arg Glu Phe Val Ala Ala Ile Arg Trp Ser Gly Gly
    210                 215                 220

Ser Ala Tyr Tyr Ala Asp Ser Val Lys Gly Arg Phe Thr Ile Ser Arg
225                 230                 235                 240

Asp Lys Ala Lys Asn Thr Val Tyr Leu Gln Met Asn Ser Leu Lys Tyr
                245                 250                 255

Glu Asp Thr Ala Val Tyr Tyr Cys Ala Arg Thr Glu Asn Val Arg Ser
            260                 265                 270

Leu Leu Ser Asp Tyr Ala Thr Trp Pro Tyr Asp Tyr Trp Gly Gln Gly
        275                 280                 285
```

-continued

```
Thr Gln Val Thr Val Ser Ser Gly Thr Gly Gly Gly Gly Ser Gly Gly
    290                 295                 300

Gly Gly Ser Gly Gly Gly Gly Ser Gly Ser Glu Pro Lys Ser Cys Asp
305                 310                 315                 320

Lys Thr His Thr Cys Pro Pro Cys Pro Ala Pro Glu Leu Leu Gly Gly
                325                 330                 335

Pro Ser Val Phe Leu Phe Pro Pro Lys Pro Lys Asp Thr Leu Met Ile
            340                 345                 350

Ser Arg Thr Pro Glu Val Thr Cys Val Val Val Asp Val Ser His Glu
        355                 360                 365

Asp Pro Glu Val Lys Phe Asn Trp Tyr Val Asp Gly Val Glu Val His
    370                 375                 380

Asn Ala Lys Thr Lys Pro Arg Glu Glu Gln Tyr Asn Ser Thr Tyr Arg
385                 390                 395                 400

Val Val Ser Val Leu Thr Val Leu His Gln Asp Trp Leu Asn Gly Lys
                405                 410                 415

Glu Tyr Lys Cys Lys Val Ser Asn Lys Ala Leu Pro Ala Pro Ile Glu
            420                 425                 430

Lys Thr Ile Ser Lys Ala Lys Gly Gln Pro Arg Glu Pro Gln Val Tyr
        435                 440                 445

Thr Leu Pro Pro Ser Arg Glu Glu Met Thr Lys Asn Gln Val Ser Leu
    450                 455                 460

Thr Cys Leu Val Lys Gly Phe Tyr Pro Ser Asp Ile Ala Val Glu Trp
465                 470                 475                 480

Glu Ser Asn Gly Gln Pro Glu Asn Asn Tyr Lys Thr Thr Pro Pro Val
                485                 490                 495

Leu Asp Ser Asp Gly Ser Phe Phe Leu Tyr Ser Lys Leu Thr Val Asp
            500                 505                 510

Lys Ser Arg Trp Gln Gln Gly Asn Val Phe Ser Cys Ser Val Met His
        515                 520                 525

Glu Ala Leu His Asn His Tyr Thr Gln Lys Ser Leu Ser Leu Ser Pro
    530                 535                 540

Gly Lys Pro Arg Gly Gly Gly Ser Gly Gly Gly Ser Gly Gly Gly Ser
545                 550                 555                 560

Ala Ala Ala Trp Ser His Pro Gln Phe Glu Lys Gly Gly Gly Ser Gly
                565                 570                 575

Gly Gly Ser Gly Gly Gly Ser Trp Ser His Pro Gln Phe Glu Lys
            580                 585                 590


<210> SEQ ID NO 17
<211> LENGTH: 1215
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(1215)

<400> SEQUENCE: 17

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg ggc gcg cct cag gtt cag ctg gtt gaa tct       96
Thr Thr Ala Leu Ser Met Gly Ala Pro Gln Val Gln Leu Val Glu Ser
            20                  25                  30

ggc gga ggc ctg atg caa gct ggc gga tct ctg aga ctg agc tgt gcc      144
```

-continued

```
Gly Gly Gly Leu Met Gln Ala Gly Gly Ser Leu Arg Leu Ser Cys Ala
        35                  40                  45

gtg tcc ggc aga acc ttt tct aca gcc gcc atg ggc tgg ttc aga cag      192
Val Ser Gly Arg Thr Phe Ser Thr Ala Ala Met Gly Trp Phe Arg Gln
    50                  55                  60

gcc cct gga aaa gaa cgc gag ttc gtg gcc gct atc cgt tgg agc gga      240
Ala Pro Gly Lys Glu Arg Glu Phe Val Ala Ala Ile Arg Trp Ser Gly
65                  70                  75                  80

ggc tct gcc tac tac gcc gat tct gtg aag ggc aga ttc acc atc agc      288
Gly Ser Ala Tyr Tyr Ala Asp Ser Val Lys Gly Arg Phe Thr Ile Ser
                85                  90                  95

aga gac aag gcc aag aac acc gtg tac ctg cag atg aac agc ctg aag      336
Arg Asp Lys Ala Lys Asn Thr Val Tyr Leu Gln Met Asn Ser Leu Lys
            100                 105                 110

tac gag gac acc gcc gtg tac tac tgc gcc aga aca gag aat gtg cgg      384
Tyr Glu Asp Thr Ala Val Tyr Tyr Cys Ala Arg Thr Glu Asn Val Arg
        115                 120                 125

agc ctg ctg agc gac tac gcc acc tgg cct tac gat tat tgg ggc cag      432
Ser Leu Leu Ser Asp Tyr Ala Thr Trp Pro Tyr Asp Tyr Trp Gly Gln
    130                 135                 140

ggc acc caa gtg acc gtt tct ggt ggc gga gga agc gga ggc gga gga      480
Gly Thr Gln Val Thr Val Ser Gly Gly Gly Gly Ser Gly Gly Gly Gly
145                 150                 155                 160

tca ggt ggc ggt gga tct atc gat cag gtg cag ctc gtg gaa agc ggt      528
Ser Gly Gly Gly Gly Ser Ile Asp Gln Val Gln Leu Val Glu Ser Gly
                165                 170                 175

ggc gga ctt atg cag gca ggc gga agc ctg aga ctg tct tgt gct gtg      576
Gly Gly Leu Met Gln Ala Gly Gly Ser Leu Arg Leu Ser Cys Ala Val
            180                 185                 190

tct ggc cgg acc ttt agc acc gct gct atg gga tgg ttt agg cag gct      624
Ser Gly Arg Thr Phe Ser Thr Ala Ala Met Gly Trp Phe Arg Gln Ala
        195                 200                 205

cca ggc aaa gaa agg gaa ttt gtg gcc gcc att cgt tgg agt ggc ggc      672
Pro Gly Lys Glu Arg Glu Phe Val Ala Ala Ile Arg Trp Ser Gly Gly
    210                 215                 220

agc gcc tat tat gcc gat agc gtg aaa ggc cgg ttc acc atc tct cgc      720
Ser Ala Tyr Tyr Ala Asp Ser Val Lys Gly Arg Phe Thr Ile Ser Arg
225                 230                 235                 240

gat aag gct aag aat acg gtc tat ctc cag atg aac tcc ctc aaa tat      768
Asp Lys Ala Lys Asn Thr Val Tyr Leu Gln Met Asn Ser Leu Lys Tyr
                245                 250                 255

gag gat acg gcc gtc tac tat tgt gcc cgg acc gaa aat gtg cgc tcc      816
Glu Asp Thr Ala Val Tyr Tyr Cys Ala Arg Thr Glu Asn Val Arg Ser
            260                 265                 270

ctg ctg tct gat tat gcc aca tgg ccc tat gac tac tgg gga cag gga      864
Leu Leu Ser Asp Tyr Ala Thr Trp Pro Tyr Asp Tyr Trp Gly Gln Gly
        275                 280                 285

aca caa gtc aca gtg tcc agc ggt acc gag cct aag atc cct cag cct      912
Thr Gln Val Thr Val Ser Ser Gly Thr Glu Pro Lys Ile Pro Gln Pro
    290                 295                 300

cag cca aag cct caa cca caa ccg cag cca cag cct aaa ccg cag cct      960
Gln Pro Lys Pro Gln Pro Gln Pro Gln Pro Gln Pro Lys Pro Gln Pro
305                 310                 315                 320

aag cca gag cct gag cag cgg atg aag cag atc gag gac aag atc gaa     1008
Lys Pro Glu Pro Glu Gln Arg Met Lys Gln Ile Glu Asp Lys Ile Glu
                325                 330                 335

gag atc ctg agc aaa atc tac cac atc gag aac gag atc gcc cgg atc     1056
Glu Ile Leu Ser Lys Ile Tyr His Ile Glu Asn Glu Ile Ala Arg Ile
            340                 345                 350
```

-continued

```
aag aag ctc gtc ggc gaa aga ccg cgg ggt ggt ggt tcc ggc gga ggt      1104
Lys Lys Leu Val Gly Glu Arg Pro Arg Gly Gly Gly Ser Gly Gly Gly
        355                 360                 365

agt ggc ggc gga tct gcg gcc gct tgg agc cat cct cag ttc gag aaa      1152
Ser Gly Gly Gly Ser Ala Ala Ala Trp Ser His Pro Gln Phe Glu Lys
    370                 375                 380

ggc gga gga agc ggc gga ggc agc ggt ggt ggc tct tgg tca cat ccc      1200
Gly Gly Gly Ser Gly Gly Gly Ser Gly Gly Gly Ser Trp Ser His Pro
385                 390                 395                 400

cag ttt gag aag tga                                                  1215
Gln Phe Glu Lys


<210> SEQ ID NO 18
<211> LENGTH: 404
<212> TYPE: PRT
<213> ORGANISM: Artificial Sequence
<220> FEATURE:
<223> OTHER INFORMATION: Synthetic Construct

<400> SEQUENCE: 18

Met Thr Asn Lys Cys Leu Leu Gln Ile Ala Leu Leu Leu Cys Phe Ser
1               5                   10                  15

Thr Thr Ala Leu Ser Met Gly Ala Pro Gln Val Gln Leu Val Glu Ser
            20                  25                  30

Gly Gly Gly Leu Met Gln Ala Gly Gly Ser Leu Arg Leu Ser Cys Ala
        35                  40                  45

Val Ser Gly Arg Thr Phe Ser Thr Ala Ala Met Gly Trp Phe Arg Gln
    50                  55                  60

Ala Pro Gly Lys Glu Arg Glu Phe Val Ala Ala Ile Arg Trp Ser Gly
65                  70                  75                  80

Gly Ser Ala Tyr Tyr Ala Asp Ser Val Lys Gly Arg Phe Thr Ile Ser
                85                  90                  95

Arg Asp Lys Ala Lys Asn Thr Val Tyr Leu Gln Met Asn Ser Leu Lys
            100                 105                 110

Tyr Glu Asp Thr Ala Val Tyr Tyr Cys Ala Arg Thr Glu Asn Val Arg
        115                 120                 125

Ser Leu Leu Ser Asp Tyr Ala Thr Trp Pro Tyr Asp Tyr Trp Gly Gln
    130                 135                 140

Gly Thr Gln Val Thr Val Ser Gly Gly Gly Gly Ser Gly Gly Gly Gly
145                 150                 155                 160

Ser Gly Gly Gly Gly Ser Ile Asp Gln Val Gln Leu Val Glu Ser Gly
                165                 170                 175

Gly Gly Leu Met Gln Ala Gly Gly Ser Leu Arg Leu Ser Cys Ala Val
            180                 185                 190

Ser Gly Arg Thr Phe Ser Thr Ala Ala Met Gly Trp Phe Arg Gln Ala
        195                 200                 205

Pro Gly Lys Glu Arg Glu Phe Val Ala Ala Ile Arg Trp Ser Gly Gly
    210                 215                 220

Ser Ala Tyr Tyr Ala Asp Ser Val Lys Gly Arg Phe Thr Ile Ser Arg
225                 230                 235                 240

Asp Lys Ala Lys Asn Thr Val Tyr Leu Gln Met Asn Ser Leu Lys Tyr
                245                 250                 255

Glu Asp Thr Ala Val Tyr Tyr Cys Ala Arg Thr Glu Asn Val Arg Ser
            260                 265                 270

Leu Leu Ser Asp Tyr Ala Thr Trp Pro Tyr Asp Tyr Trp Gly Gln Gly
        275                 280                 285
```

```
Thr Gln Val Thr Val Ser Ser Gly Thr Glu Pro Lys Ile Pro Gln Pro
    290                 295                 300

Gln Pro Lys Pro Gln Pro Gln Pro Gln Pro Gln Pro Lys Pro Gln Pro
305                 310                 315                 320

Lys Pro Glu Pro Glu Gln Arg Met Lys Gln Ile Glu Asp Lys Ile Glu
                325                 330                 335

Glu Ile Leu Ser Lys Ile Tyr His Ile Glu Asn Glu Ile Ala Arg Ile
            340                 345                 350

Lys Lys Leu Val Gly Glu Arg Pro Arg Gly Gly Gly Ser Gly Gly Gly
        355                 360                 365

Ser Gly Gly Gly Ser Ala Ala Ala Trp Ser His Pro Gln Phe Glu Lys
    370                 375                 380

Gly Gly Gly Ser Gly Gly Gly Ser Gly Gly Gly Ser Trp Ser His Pro
385                 390                 395                 400

Gln Phe Glu Lys


<210> SEQ ID NO 19
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(66)

<400> SEQUENCE: 19

atg acc aac aag tgc ctg ctg cag att gcc ctg ctg ctg tgc ttc agc       48
Met Thr Asn Lys Cys Leu Leu Gln Ile Ala Leu Leu Leu Cys Phe Ser
1               5                   10                  15

aca aca gcc ctg tct atg                                               66
Thr Thr Ala Leu Ser Met
            20


<210> SEQ ID NO 20
<211> LENGTH: 22
<212> TYPE: PRT
<213> ORGANISM: Artificial Sequence
<220> FEATURE:
<223> OTHER INFORMATION: Synthetic Construct

<400> SEQUENCE: 20

Met Thr Asn Lys Cys Leu Leu Gln Ile Ala Leu Leu Leu Cys Phe Ser
1               5                   10                  15

Thr Thr Ala Leu Ser Met
            20


<210> SEQ ID NO 21
<211> LENGTH: 369
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(369)

<400> SEQUENCE: 21

caa gtt cag ctt caa gaa tct ggc ggc gga agc gtt cag gct ggc gga       48
Gln Val Gln Leu Gln Glu Ser Gly Gly Gly Ser Val Gln Ala Gly Gly
1               5                   10                  15

tct ctg aga ctg agc tgt gtg gcc agc ggc tac acc gat agc aca tac       96
Ser Leu Arg Leu Ser Cys Val Ala Ser Gly Tyr Thr Asp Ser Thr Tyr
```

```
            20                  25                  30

tgc gtc ggc tgg ttc aga cag gcc cct ggc aaa gag aga gag ggc gtc       144
Cys Val Gly Trp Phe Arg Gln Ala Pro Gly Lys Glu Arg Glu Gly Val
        35                  40                  45

gcc aga atc aac acc atc agc ggc aga cct tgg tac gcc gac tct gtg       192
Ala Arg Ile Asn Thr Ile Ser Gly Arg Pro Trp Tyr Ala Asp Ser Val
    50                  55                  60

aag ggc aga ttc aca atc agc cag gac aac agc aag aac acc gtg tac       240
Lys Gly Arg Phe Thr Ile Ser Gln Asp Asn Ser Lys Asn Thr Val Tyr
65                  70                  75                  80

ctg cag atg aac agc ctg aag cct gag gac acc gcc atc tac tac tgc       288
Leu Gln Met Asn Ser Leu Lys Pro Glu Asp Thr Ala Ile Tyr Tyr Cys
                85                  90                  95

acc ctg acc acc gcc aac agc aga ggc ttt tgt tcc ggc ggc tac aac       336
Thr Leu Thr Thr Ala Asn Ser Arg Gly Phe Cys Ser Gly Gly Tyr Asn
            100                 105                 110

tac aaa ggc cag ggc acc caa gtg acc gtg tct                           369
Tyr Lys Gly Gln Gly Thr Gln Val Thr Val Ser
        115                 120


<210> SEQ ID NO 22
<211> LENGTH: 123
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asp Ser Thr Tyr
            20                  25                  30

Cys Val Gly Trp Phe Arg Gln Ala Pro Gly Lys Glu Arg Glu Gly Val
        35                  40                  45

Ala Arg Ile Asn Thr Ile Ser Gly Arg Pro Trp Tyr Ala Asp Ser Val
    50                  55                  60

Lys Gly Arg Phe Thr Ile Ser Gln Asp Asn Ser Lys Asn Thr Val Tyr
65                  70                  75                  80

Leu Gln Met Asn Ser Leu Lys Pro Glu Asp Thr Ala Ile Tyr Tyr Cys
                85                  90                  95

Thr Leu Thr Thr Ala Asn Ser Arg Gly Phe Cys Ser Gly Gly Tyr Asn
            100                 105                 110

Tyr Lys Gly Gln Gly Thr Gln Val Thr Val Ser
        115                 120


<210> SEQ ID NO 23
<211> LENGTH: 3822
<212> TYPE: DNA
<213> ORGANISM: SARS-CoV-2
<220> FEATURE:
<221> NAME/KEY: CDS
<222> LOCATION: (1)..(3822)

<400> SEQUENCE: 23

atg ttt gtt ttt ctt gtt tta ttg cca cta gtc tct agt cag tgt gtt        48
Met Phe Val Phe Leu Val Leu Leu Pro Leu Val Ser Ser Gln Cys Val
1               5                   10                  15

aat ctt aca acc aga act caa tta ccc cct gca tac act aat tct ttc        96
Asn Leu Thr Thr Arg Thr Gln Leu Pro Pro Ala Tyr Thr Asn Ser Phe
            20                  25                  30
```

-continued

```
aca cgt ggt gtt tat tac cct gac aaa gtt ttc aga tcc tca gtt tta      144
Thr Arg Gly Val Tyr Tyr Pro Asp Lys Val Phe Arg Ser Ser Val Leu
        35                  40                  45

cat tca act cag gac ttg ttc tta cct ttc ttt tcc aat gtt act tgg      192
His Ser Thr Gln Asp Leu Phe Leu Pro Phe Phe Ser Asn Val Thr Trp
    50                  55                  60

ttc cat gct ata cat gtc tct ggg acc aat ggt act aag agg ttt gat      240
Phe His Ala Ile His Val Ser Gly Thr Asn Gly Thr Lys Arg Phe Asp
65                  70                  75                  80

aac cct gtc cta cca ttt aat gat ggt gtt tat ttt gct tcc act gag      288
Asn Pro Val Leu Pro Phe Asn Asp Gly Val Tyr Phe Ala Ser Thr Glu
                85                  90                  95

aag tct aac ata ata aga ggc tgg att ttt ggt act act tta gat tcg      336
Lys Ser Asn Ile Ile Arg Gly Trp Ile Phe Gly Thr Thr Leu Asp Ser
            100                 105                 110

aag acc cag tcc cta ctt att gtt aat aac gct act aat gtt gtt att      384
Lys Thr Gln Ser Leu Leu Ile Val Asn Asn Ala Thr Asn Val Val Ile
        115                 120                 125

aaa gtc tgt gaa ttt caa ttt tgt aat gat cca ttt ttg ggt gtt tat      432
Lys Val Cys Glu Phe Gln Phe Cys Asn Asp Pro Phe Leu Gly Val Tyr
    130                 135                 140

tac cac aaa aac aac aaa agt tgg atg gaa agt gag ttc aga gtt tat      480
Tyr His Lys Asn Asn Lys Ser Trp Met Glu Ser Glu Phe Arg Val Tyr
145                 150                 155                 160

tct agt gcg aat aat tgc act ttt gaa tat gtc tct cag cct ttt ctt      528
Ser Ser Ala Asn Asn Cys Thr Phe Glu Tyr Val Ser Gln Pro Phe Leu
                165                 170                 175

atg gac ctt gaa gga aaa cag ggt aat ttc aaa aat ctt agg gaa ttt      576
Met Asp Leu Glu Gly Lys Gln Gly Asn Phe Lys Asn Leu Arg Glu Phe
            180                 185                 190

gtg ttt aag aat att gat ggt tat ttt aaa ata tat tct aag cac acg      624
Val Phe Lys Asn Ile Asp Gly Tyr Phe Lys Ile Tyr Ser Lys His Thr
        195                 200                 205

cct att aat tta gtg cgt gat ctc cct cag ggt ttt tcg gct tta gaa      672
Pro Ile Asn Leu Val Arg Asp Leu Pro Gln Gly Phe Ser Ala Leu Glu
    210                 215                 220

cca ttg gta gat ttg cca ata ggt att aac atc act agg ttt caa act      720
Pro Leu Val Asp Leu Pro Ile Gly Ile Asn Ile Thr Arg Phe Gln Thr
225                 230                 235                 240

tta ctt gct tta cat aga agt tat ttg act cct ggt gat tct tct tca      768
Leu Leu Ala Leu His Arg Ser Tyr Leu Thr Pro Gly Asp Ser Ser Ser
                245                 250                 255

ggt tgg aca gct ggt gct gca gct tat tat gtg ggt tat ctt caa cct      816
Gly Trp Thr Ala Gly Ala Ala Ala Tyr Tyr Val Gly Tyr Leu Gln Pro
            260                 265                 270

agg act ttt cta tta aaa tat aat gaa aat gga acc att aca gat gct      864
Arg Thr Phe Leu Leu Lys Tyr Asn Glu Asn Gly Thr Ile Thr Asp Ala
        275                 280                 285

gta gac tgt gca ctt gac cct ctc tca gaa aca aag tgt acg ttg aaa      912
Val Asp Cys Ala Leu Asp Pro Leu Ser Glu Thr Lys Cys Thr Leu Lys
    290                 295                 300

tcc ttc act gta gaa aaa gga atc tat caa act tct aac ttt aga gtc      960
Ser Phe Thr Val Glu Lys Gly Ile Tyr Gln Thr Ser Asn Phe Arg Val
305                 310                 315                 320

caa cca aca gaa tct att gtt aga ttt cct aat att aca aac ttg tgc     1008
Gln Pro Thr Glu Ser Ile Val Arg Phe Pro Asn Ile Thr Asn Leu Cys
                325                 330                 335

cct ttt ggt gaa gtt ttt aac gcc acc aga ttt gca tct gtt tat gct     1056
Pro Phe Gly Glu Val Phe Asn Ala Thr Arg Phe Ala Ser Val Tyr Ala
            340                 345                 350
```

-continued

```
tgg aac agg aag aga atc agc aac tgt gtt gct gat tat tct gtc cta     1104
Trp Asn Arg Lys Arg Ile Ser Asn Cys Val Ala Asp Tyr Ser Val Leu
        355                 360                 365

tat aat tcc gca tca ttt tcc act ttt aag tgt tat gga gtg tct cct     1152
Tyr Asn Ser Ala Ser Phe Ser Thr Phe Lys Cys Tyr Gly Val Ser Pro
    370                 375                 380

act aaa tta aat gat ctc tgc ttt act aat gtc tat gca gat tca ttt     1200
Thr Lys Leu Asn Asp Leu Cys Phe Thr Asn Val Tyr Ala Asp Ser Phe
385                 390                 395                 400

gta att aga ggt gat gaa gtc aga caa atc gct cca ggg caa act gga     1248
Val Ile Arg Gly Asp Glu Val Arg Gln Ile Ala Pro Gly Gln Thr Gly
                405                 410                 415

aag att gct gat tat aat tat aaa tta cca gat gat ttt aca ggc tgc     1296
Lys Ile Ala Asp Tyr Asn Tyr Lys Leu Pro Asp Asp Phe Thr Gly Cys
            420                 425                 430

gtt ata gct tgg aat tct aac aat ctt gat tct aag gtt ggt ggt aat     1344
Val Ile Ala Trp Asn Ser Asn Asn Leu Asp Ser Lys Val Gly Gly Asn
        435                 440                 445

tat aat tac ctg tat aga ttg ttt agg aag tct aat ctc aaa cct ttt     1392
Tyr Asn Tyr Leu Tyr Arg Leu Phe Arg Lys Ser Asn Leu Lys Pro Phe
    450                 455                 460

gag aga gat att tca act gaa atc tat cag gcc ggt agc aca cct tgt     1440
Glu Arg Asp Ile Ser Thr Glu Ile Tyr Gln Ala Gly Ser Thr Pro Cys
465                 470                 475                 480

aat ggt gtt gaa ggt ttt aat tgt tac ttt cct tta caa tca tat ggt     1488
Asn Gly Val Glu Gly Phe Asn Cys Tyr Phe Pro Leu Gln Ser Tyr Gly
                485                 490                 495

ttc caa ccc act aat ggt gtt ggt tac caa cca tac aga gta gta gta     1536
Phe Gln Pro Thr Asn Gly Val Gly Tyr Gln Pro Tyr Arg Val Val Val
            500                 505                 510

ctt tct ttt gaa ctt cta cat gca cca gca act gtt tgt gga cct aaa     1584
Leu Ser Phe Glu Leu Leu His Ala Pro Ala Thr Val Cys Gly Pro Lys
        515                 520                 525

aag tct act aat ttg gtt aaa aac aaa tgt gtc aat ttc aac ttc aat     1632
Lys Ser Thr Asn Leu Val Lys Asn Lys Cys Val Asn Phe Asn Phe Asn
    530                 535                 540

ggt tta aca ggc aca ggt gtt ctt act gag tct aac aaa aag ttt ctg     1680
Gly Leu Thr Gly Thr Gly Val Leu Thr Glu Ser Asn Lys Lys Phe Leu
545                 550                 555                 560

cct ttc caa caa ttt ggc aga gac att gct gac act act gat gct gtc     1728
Pro Phe Gln Gln Phe Gly Arg Asp Ile Ala Asp Thr Thr Asp Ala Val
                565                 570                 575

cgt gat cca cag aca ctt gag att ctt gac att aca cca tgt tct ttt     1776
Arg Asp Pro Gln Thr Leu Glu Ile Leu Asp Ile Thr Pro Cys Ser Phe
            580                 585                 590

ggt ggt gtc agt gtt ata aca cca gga aca aat act tct aac cag gtt     1824
Gly Gly Val Ser Val Ile Thr Pro Gly Thr Asn Thr Ser Asn Gln Val
        595                 600                 605

gct gtt ctt tat cag gat gtt aac tgc aca gaa gtc cct gtt gct att     1872
Ala Val Leu Tyr Gln Asp Val Asn Cys Thr Glu Val Pro Val Ala Ile
    610                 615                 620

cat gca gat caa ctt act cct act tgg cgt gtt tat tct aca ggt tct     1920
His Ala Asp Gln Leu Thr Pro Thr Trp Arg Val Tyr Ser Thr Gly Ser
625                 630                 635                 640

aat gtt ttt caa aca cgt gca ggc tgt tta ata ggg gct gaa cat gtc     1968
Asn Val Phe Gln Thr Arg Ala Gly Cys Leu Ile Gly Ala Glu His Val
                645                 650                 655

aac aac tca tat gag tgt gac ata ccc att ggt gca ggt ata tgc gct     2016
Asn Asn Ser Tyr Glu Cys Asp Ile Pro Ile Gly Ala Gly Ile Cys Ala
```

```
            660                 665                 670

agt tat cag act cag act aat tct cct cgg cgg gca cgt agt gta gct      2064
Ser Tyr Gln Thr Gln Thr Asn Ser Pro Arg Arg Ala Arg Ser Val Ala
        675                 680                 685

agt caa tcc atc att gcc tac act atg tca ctt ggt gca gaa aat tca      2112
Ser Gln Ser Ile Ile Ala Tyr Thr Met Ser Leu Gly Ala Glu Asn Ser
    690                 695                 700

gtt gct tac tct aat aac tct att gcc ata ccc aca aat ttt act att      2160
Val Ala Tyr Ser Asn Asn Ser Ile Ala Ile Pro Thr Asn Phe Thr Ile
705                 710                 715                 720

agt gtt acc aca gaa att cta cca gtg tct atg acc aag aca tca gta      2208
Ser Val Thr Thr Glu Ile Leu Pro Val Ser Met Thr Lys Thr Ser Val
                725                 730                 735

gat tgt aca atg tac att tgt ggt gat tca act gaa tgc agc aat ctt      2256
Asp Cys Thr Met Tyr Ile Cys Gly Asp Ser Thr Glu Cys Ser Asn Leu
            740                 745                 750

ttg ttg caa tat ggc agt ttt tgt aca caa tta aac cgt gct tta act      2304
Leu Leu Gln Tyr Gly Ser Phe Cys Thr Gln Leu Asn Arg Ala Leu Thr
        755                 760                 765

gga ata gct gtt gaa caa gac aaa aac acc caa gaa gtt ttt gca caa      2352
Gly Ile Ala Val Glu Gln Asp Lys Asn Thr Gln Glu Val Phe Ala Gln
    770                 775                 780

gtc aaa caa att tac aaa aca cca cca att aaa gat ttt ggt ggt ttt      2400
Val Lys Gln Ile Tyr Lys Thr Pro Pro Ile Lys Asp Phe Gly Gly Phe
785                 790                 795                 800

aat ttt tca caa ata tta cca gat cca tca aaa cca agc aag agg tca      2448
Asn Phe Ser Gln Ile Leu Pro Asp Pro Ser Lys Pro Ser Lys Arg Ser
                805                 810                 815

ttt att gaa gat cta ctt ttc aac aaa gtg aca ctt gca gat gct ggc      2496
Phe Ile Glu Asp Leu Leu Phe Asn Lys Val Thr Leu Ala Asp Ala Gly
            820                 825                 830

ttc atc aaa caa tat ggt gat tgc ctt ggt gat att gct gct aga gac      2544
Phe Ile Lys Gln Tyr Gly Asp Cys Leu Gly Asp Ile Ala Ala Arg Asp
        835                 840                 845

ctc att tgt gca caa aag ttt aac ggc ctt act gtt ttg cca cct ttg      2592
Leu Ile Cys Ala Gln Lys Phe Asn Gly Leu Thr Val Leu Pro Pro Leu
    850                 855                 860

ctc aca gat gaa atg att gct caa tac act tct gca ctg tta gcg ggt      2640
Leu Thr Asp Glu Met Ile Ala Gln Tyr Thr Ser Ala Leu Leu Ala Gly
865                 870                 875                 880

aca atc act tct ggt tgg acc ttt ggt gca ggt gct gca tta caa ata      2688
Thr Ile Thr Ser Gly Trp Thr Phe Gly Ala Gly Ala Ala Leu Gln Ile
                885                 890                 895

cca ttt gct atg caa atg gct tat agg ttt aat ggt att gga gtt aca      2736
Pro Phe Ala Met Gln Met Ala Tyr Arg Phe Asn Gly Ile Gly Val Thr
            900                 905                 910

cag aat gtt ctc tat gag aac caa aaa ttg att gcc aac caa ttt aat      2784
Gln Asn Val Leu Tyr Glu Asn Gln Lys Leu Ile Ala Asn Gln Phe Asn
        915                 920                 925

agt gct att ggc aaa att caa gac tca ctt tct tcc aca gca agt gca      2832
Ser Ala Ile Gly Lys Ile Gln Asp Ser Leu Ser Ser Thr Ala Ser Ala
    930                 935                 940

ctt gga aaa ctt caa gat gtg gtc aac caa aat gca caa gct tta aac      2880
Leu Gly Lys Leu Gln Asp Val Val Asn Gln Asn Ala Gln Ala Leu Asn
945                 950                 955                 960

acg ctt gtt aaa caa ctt agc tcc aat ttt ggt gca att tca agt gtt      2928
Thr Leu Val Lys Gln Leu Ser Ser Asn Phe Gly Ala Ile Ser Ser Val
                965                 970                 975

tta aat gat atc ctt tca cgt ctt gac aaa gtt gag gct gaa gtg caa      2976
```

-continued

```
Leu Asn Asp Ile Leu Ser Arg Leu Asp Lys Val Glu Ala Glu Val Gln
            980                 985                 990

att gat agg ttg atc aca ggc aga  ctt caa agt ttg cag  aca tat gtg   3024
Ile Asp Arg Leu Ile Thr Gly Arg  Leu Gln Ser Leu Gln  Thr Tyr Val
        995                 1000                 1005

act caa  caa tta att aga gct  gca gaa atc aga gct  tct gct aat     3069
Thr Gln  Gln Leu Ile Arg Ala  Ala Glu Ile Arg Ala  Ser Ala Asn
    1010                 1015                 1020

ctt gct  gct act aaa atg tca  gag tgt gta ctt gga  caa tca aaa     3114
Leu Ala  Ala Thr Lys Met Ser  Glu Cys Val Leu Gly  Gln Ser Lys
    1025                 1030                 1035

aga gtt  gat ttt tgt gga aag  ggc tat cat ctt atg  tcc ttc cct     3159
Arg Val  Asp Phe Cys Gly Lys  Gly Tyr His Leu Met  Ser Phe Pro
    1040                 1045                 1050

cag tca  gca cct cat ggt gta  gtc ttc ttg cat gtg  act tat gtc     3204
Gln Ser  Ala Pro His Gly Val  Val Phe Leu His Val  Thr Tyr Val
    1055                 1060                 1065

cct gca  caa gaa aag aac ttc  aca act gct cct gcc  att tgt cat     3249
Pro Ala  Gln Glu Lys Asn Phe  Thr Thr Ala Pro Ala  Ile Cys His
    1070                 1075                 1080

gat gga  aaa gca cac ttt cct  cgt gaa ggt gtc ttt  gtt tca aat     3294
Asp Gly  Lys Ala His Phe Pro  Arg Glu Gly Val Phe  Val Ser Asn
    1085                 1090                 1095

ggc aca  cac tgg ttt gta aca  caa agg aat ttt tat  gaa cca caa     3339
Gly Thr  His Trp Phe Val Thr  Gln Arg Asn Phe Tyr  Glu Pro Gln
    1100                 1105                 1110

atc att  act aca gac aac aca  ttt gtg tct ggt aac  tgt gat gtt     3384
Ile Ile  Thr Thr Asp Asn Thr  Phe Val Ser Gly Asn  Cys Asp Val
    1115                 1120                 1125

gta ata  gga att gtc aac aac  aca gtt tat gat cct  ttg caa cct     3429
Val Ile  Gly Ile Val Asn Asn  Thr Val Tyr Asp Pro  Leu Gln Pro
    1130                 1135                 1140

gaa tta  gac tca ttc aag gag  gag tta gat aaa tat  ttt aag aat     3474
Glu Leu  Asp Ser Phe Lys Glu  Glu Leu Asp Lys Tyr  Phe Lys Asn
    1145                 1150                 1155

cat aca  tca cca gat gtt gat  tta ggt gac atc tct  ggc att aat     3519
His Thr  Ser Pro Asp Val Asp  Leu Gly Asp Ile Ser  Gly Ile Asn
    1160                 1165                 1170

gct tca  gtt gta aac att caa  aaa gaa att gac cgc  ctc aat gag     3564
Ala Ser  Val Val Asn Ile Gln  Lys Glu Ile Asp Arg  Leu Asn Glu
    1175                 1180                 1185

gtt gcc  aag aat tta aat gaa  tct ctc atc gat ctc  caa gaa ctt     3609
Val Ala  Lys Asn Leu Asn Glu  Ser Leu Ile Asp Leu  Gln Glu Leu
    1190                 1195                 1200

gga aag  tat gag cag tat ata  aaa tgg cca tgg tac  att tgg cta     3654
Gly Lys  Tyr Glu Gln Tyr Ile  Lys Trp Pro Trp Tyr  Ile Trp Leu
    1205                 1210                 1215

ggt ttt  ata gct ggc ttg att  gcc ata gta atg gtg  aca att atg     3699
Gly Phe  Ile Ala Gly Leu Ile  Ala Ile Val Met Val  Thr Ile Met
    1220                 1225                 1230

ctt tgc  tgt atg acc agt tgc  tgt agt tgt ctc aag  ggc tgt tgt     3744
Leu Cys  Cys Met Thr Ser Cys  Cys Ser Cys Leu Lys  Gly Cys Cys
    1235                 1240                 1245

tct tgt  gga tcc tgc tgc aaa  ttt gat gaa gac gac  tct gag cca     3789
Ser Cys  Gly Ser Cys Cys Lys  Phe Asp Glu Asp Asp  Ser Glu Pro
    1250                 1255                 1260

gtg ctc  aaa gga gtc aaa tta  cat tac aca taa                      3822
Val Leu  Lys Gly Val Lys Leu  His Tyr Thr
    1265                 1270
```

<210> SEQ ID NO 24
<211> LENGTH: 1273
<212> TYPE: PRT
<213> ORGANISM: SARS-CoV-2

<400> SEQUENCE: 24

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380
```

-continued

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800
```

-continued

```
Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
```

```
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270


<210> SEQ ID NO 25
<211> LENGTH: 1260
<212> TYPE: DNA
<213> ORGANISM: SARS-CoV-2
<220> FEATURE:
<221> NAME/KEY: CDS
<222> LOCATION: (1)..(1260)

<400> SEQUENCE: 25

atg tct gat aat gga ccc caa aat cag cga aat gca ccc cgc att acg       48
Met Ser Asp Asn Gly Pro Gln Asn Gln Arg Asn Ala Pro Arg Ile Thr
1               5                   10                  15

ttt ggt gga ccc tca gat tca act ggc agt aac cag aat gga gaa cgc       96
Phe Gly Gly Pro Ser Asp Ser Thr Gly Ser Asn Gln Asn Gly Glu Arg
            20                  25                  30

agt ggg gcg cga tca aaa caa cgt cgg ccc caa ggt tta ccc aat aat      144
Ser Gly Ala Arg Ser Lys Gln Arg Arg Pro Gln Gly Leu Pro Asn Asn
        35                  40                  45

act gcg tct tgg ttc acc gct ctc act caa cat ggc aag gaa gac ctt      192
Thr Ala Ser Trp Phe Thr Ala Leu Thr Gln His Gly Lys Glu Asp Leu
    50                  55                  60

aaa ttc cct cga gga caa ggc gtt cca att aac acc aat agc agt cca      240
Lys Phe Pro Arg Gly Gln Gly Val Pro Ile Asn Thr Asn Ser Ser Pro
65                  70                  75                  80

gat gac caa att ggc tac tac cga aga gct acc aga cga att cgt ggt      288
Asp Asp Gln Ile Gly Tyr Tyr Arg Arg Ala Thr Arg Arg Ile Arg Gly
                85                  90                  95

ggt gac ggt aaa atg aaa gat ctc agt cca aga tgg tat ttc tac tac      336
Gly Asp Gly Lys Met Lys Asp Leu Ser Pro Arg Trp Tyr Phe Tyr Tyr
            100                 105                 110

cta gga act ggg cca gaa gct gga ctt ccc tat ggt gct aac aaa gac      384
Leu Gly Thr Gly Pro Glu Ala Gly Leu Pro Tyr Gly Ala Asn Lys Asp
        115                 120                 125

ggc atc ata tgg gtt gca act gag gga gcc ttg aat aca cca aaa gat      432
Gly Ile Ile Trp Val Ala Thr Glu Gly Ala Leu Asn Thr Pro Lys Asp
    130                 135                 140

cac att ggc acc cgc aat cct gct aac aat gct gca atc gtg cta caa      480
His Ile Gly Thr Arg Asn Pro Ala Asn Asn Ala Ala Ile Val Leu Gln
145                 150                 155                 160

ctt cct caa gga aca aca ttg cca aaa ggc ttc tac gca gaa ggg agc      528
Leu Pro Gln Gly Thr Thr Leu Pro Lys Gly Phe Tyr Ala Glu Gly Ser
                165                 170                 175

aga ggc ggc agt caa gcc tct tct cgt tcc tca tca cgt agt cgc aac      576
Arg Gly Gly Ser Gln Ala Ser Ser Arg Ser Ser Ser Arg Ser Arg Asn
            180                 185                 190

agt tca aga aat tca act cca ggc agc agt agg gga act tct cct gct      624
Ser Ser Arg Asn Ser Thr Pro Gly Ser Ser Arg Gly Thr Ser Pro Ala
        195                 200                 205

aga atg gct ggc aat ggc ggt gat gct gct ctt gct ttg ctg ctg ctt      672
Arg Met Ala Gly Asn Gly Gly Asp Ala Ala Leu Ala Leu Leu Leu Leu
```

```
    210                 215                 220

gac aga ttg aac cag ctt gag agc aaa atg tct ggt aaa ggc caa caa      720
Asp Arg Leu Asn Gln Leu Glu Ser Lys Met Ser Gly Lys Gly Gln Gln
225                 230                 235                 240

caa caa ggc caa act gtc act aag aaa tct gct gct gag gct tct aag      768
Gln Gln Gly Gln Thr Val Thr Lys Lys Ser Ala Ala Glu Ala Ser Lys
                245                 250                 255

aag cct cgg caa aaa cgt act gcc act aaa gca tac aat gta aca caa      816
Lys Pro Arg Gln Lys Arg Thr Ala Thr Lys Ala Tyr Asn Val Thr Gln
            260                 265                 270

gct ttc ggc aga cgt ggt cca gaa caa acc caa gga aat ttt ggg gac      864
Ala Phe Gly Arg Arg Gly Pro Glu Gln Thr Gln Gly Asn Phe Gly Asp
        275                 280                 285

cag gaa cta atc aga caa gga act gat tac aaa cat tgg ccg caa att      912
Gln Glu Leu Ile Arg Gln Gly Thr Asp Tyr Lys His Trp Pro Gln Ile
    290                 295                 300

gca caa ttt gcc ccc agc gct tca gcg ttc ttc gga atg tcg cgc att      960
Ala Gln Phe Ala Pro Ser Ala Ser Ala Phe Phe Gly Met Ser Arg Ile
305                 310                 315                 320

ggc atg gaa gtc aca cct tcg gga acg tgg ttg acc tac aca ggt gcc     1008
Gly Met Glu Val Thr Pro Ser Gly Thr Trp Leu Thr Tyr Thr Gly Ala
                325                 330                 335

atc aaa ttg gat gac aaa gat cca aat ttc aaa gat caa gtc att ttg     1056
Ile Lys Leu Asp Asp Lys Asp Pro Asn Phe Lys Asp Gln Val Ile Leu
            340                 345                 350

ctg aat aag cat att gac gca tac aaa aca ttc cca cca aca gag cct     1104
Leu Asn Lys His Ile Asp Ala Tyr Lys Thr Phe Pro Pro Thr Glu Pro
        355                 360                 365

aaa aag gac aaa aag aag aag gct gat gaa act caa gcc tta ccg cag     1152
Lys Lys Asp Lys Lys Lys Lys Ala Asp Glu Thr Gln Ala Leu Pro Gln
    370                 375                 380

aga cag aag aaa cag caa act gtg act ctt ctt cct gct gca gat ttg     1200
Arg Gln Lys Lys Gln Gln Thr Val Thr Leu Leu Pro Ala Ala Asp Leu
385                 390                 395                 400

gat gat ttc tcc aaa caa ttg caa caa tcc atg agc agt gct gac tca     1248
Asp Asp Phe Ser Lys Gln Leu Gln Gln Ser Met Ser Ser Ala Asp Ser
                405                 410                 415

act cag gcc taa                                                     1260
Thr Gln Ala


<210> SEQ ID NO 26
<211> LENGTH: 419
<212> TYPE: PRT
<213> ORGANISM: SARS-CoV-2

<400> SEQUENCE: 26

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95
```

-continued

```
Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala


<210> SEQ ID NO 27
<211> LENGTH: 366
<212> TYPE: DNA
<213> ORGANISM: SARS-CoV-2
<220> FEATURE:
<221> NAME/KEY: CDS
<222> LOCATION: (1)..(366)

<400> SEQUENCE: 27

atg aaa ttt ctt gtt ttc tta gga atc atc aca act gta gct gca ttt       48
Met Lys Phe Leu Val Phe Leu Gly Ile Ile Thr Thr Val Ala Ala Phe
1               5                   10                  15

cac caa gaa tgt agt tta cag tca tgt act caa cat caa cca tat gta       96
His Gln Glu Cys Ser Leu Gln Ser Cys Thr Gln His Gln Pro Tyr Val
```

```
            20                  25                  30

gtt gat gac ccg tgt cct att cac ttc tat tct aaa tgg tat att aga      144
Val Asp Asp Pro Cys Pro Ile His Phe Tyr Ser Lys Trp Tyr Ile Arg
        35                  40                  45

gta gga gct aga aaa tca gca cct tta att gaa ttg tgc gtg gat gag      192
Val Gly Ala Arg Lys Ser Ala Pro Leu Ile Glu Leu Cys Val Asp Glu
    50                  55                  60

gct ggt tct aaa tca ccc att cag tac atc gat atc ggt aat tat aca      240
Ala Gly Ser Lys Ser Pro Ile Gln Tyr Ile Asp Ile Gly Asn Tyr Thr
65                  70                  75                  80

gtt tcc tgt tta cct ttt aca att aat tgc cag gaa cct aaa ttg ggt      288
Val Ser Cys Leu Pro Phe Thr Ile Asn Cys Gln Glu Pro Lys Leu Gly
                85                  90                  95

agt ctt gta gtg cgt tgt tcg ttc tat gaa gac ttt tta gag tat cat      336
Ser Leu Val Val Arg Cys Ser Phe Tyr Glu Asp Phe Leu Glu Tyr His
            100                 105                 110

gac gtt cgt gtt gtt tta gat ttc atc taa                              366
Asp Val Arg Val Val Leu Asp Phe Ile
        115                 120


<210> SEQ ID NO 28
<211> LENGTH: 121
<212> TYPE: PRT
<213> ORGANISM: SARS-CoV-2

<400> SEQUENCE: 28

Met Lys Phe Leu Val Phe Leu Gly Ile Ile Thr Thr Val Ala Ala Phe
1               5                   10                  15

His Gln Glu Cys Ser Leu Gln Ser Cys Thr Gln His Gln Pro Tyr Val
            20                  25                  30

Val Asp Asp Pro Cys Pro Ile His Phe Tyr Ser Lys Trp Tyr Ile Arg
        35                  40                  45

Val Gly Ala Arg Lys Ser Ala Pro Leu Ile Glu Leu Cys Val Asp Glu
    50                  55                  60

Ala Gly Ser Lys Ser Pro Ile Gln Tyr Ile Asp Ile Gly Asn Tyr Thr
65                  70                  75                  80

Val Ser Cys Leu Pro Phe Thr Ile Asn Cys Gln Glu Pro Lys Leu Gly
                85                  90                  95

Ser Leu Val Val Arg Cys Ser Phe Tyr Glu Asp Phe Leu Glu Tyr His
            100                 105                 110

Asp Val Arg Val Val Leu Asp Phe Ile
        115                 120


<210> SEQ ID NO 29
<211> LENGTH: 300
<212> TYPE: DNA
<213> ORGANISM: SARS-CoV-2
<220> FEATURE:
<221> NAME/KEY: CDS
<222> LOCATION: (1)..(300)

<400> SEQUENCE: 29

atg gcc tac tgt tgg aga tgc acc agc tgc tgc ttc agc gag cgg ttc       48
Met Ala Tyr Cys Trp Arg Cys Thr Ser Cys Cys Phe Ser Glu Arg Phe
1               5                   10                  15

cag aac cac aat cct cag aaa gag atg gcc acc agc aca ctg cag ggc       96
Gln Asn His Asn Pro Gln Lys Glu Met Ala Thr Ser Thr Leu Gln Gly
            20                  25                  30

tgt tct ctg tgt ctg cag ctg gcc gtg gtg gtc aac tct ctg ctg acc      144
Cys Ser Leu Cys Leu Gln Leu Ala Val Val Val Asn Ser Leu Leu Thr
```

```
        35                  40                  45

cct ttc gcc aga tgc tgc tgg cct gaa ttc ggc gga ggc agc ggc ggt      192
Pro Phe Ala Arg Cys Cys Trp Pro Glu Phe Gly Gly Gly Ser Gly Gly
    50                  55                  60

gga agc ggc gga ggc tct gct tgg agc cac ccg cag ttc gaa aaa ggt      240
Gly Ser Gly Gly Gly Ser Ala Trp Ser His Pro Gln Phe Glu Lys Gly
65                  70                  75                  80

gga ggt tct ggc ggt gga tcg gga ggt tca gcg tgg agc cac ccg cag      288
Gly Gly Ser Gly Gly Gly Ser Gly Gly Ser Ala Trp Ser His Pro Gln
                85                  90                  95

ttc gag aaa tga                                                      300
Phe Glu Lys


<210> SEQ ID NO 30
<211> LENGTH: 99
<212> TYPE: PRT
<213> ORGANISM: SARS-CoV-2

<400> SEQUENCE: 30

Met Ala Tyr Cys Trp Arg Cys Thr Ser Cys Cys Phe Ser Glu Arg Phe
1               5                   10                  15

Gln Asn His Asn Pro Gln Lys Glu Met Ala Thr Ser Thr Leu Gln Gly
            20                  25                  30

Cys Ser Leu Cys Leu Gln Leu Ala Val Val Val Asn Ser Leu Leu Thr
        35                  40                  45

Pro Phe Ala Arg Cys Cys Trp Pro Glu Phe Gly Gly Gly Ser Gly Gly
    50                  55                  60

Gly Ser Gly Gly Gly Ser Ala Trp Ser His Pro Gln Phe Glu Lys Gly
65                  70                  75                  80

Gly Gly Ser Gly Gly Gly Ser Gly Gly Ser Ala Trp Ser His Pro Gln
                85                  90                  95

Phe Glu Lys


<210> SEQ ID NO 31
<211> LENGTH: 378
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(378)

<400> SEQUENCE: 31

cag gtt cag ctg gtt gaa tct ggc gga ggc ctg atg caa gct ggc gga       48
Gln Val Gln Leu Val Glu Ser Gly Gly Gly Leu Met Gln Ala Gly Gly
1               5                   10                  15

tct ctg aga ctg agc tgt gcc gtg tcc ggc aga acc ttt tct aca gcc       96
Ser Leu Arg Leu Ser Cys Ala Val Ser Gly Arg Thr Phe Ser Thr Ala
            20                  25                  30

gcc atg ggc tgg ttc aga cag gcc cct gga aaa gaa cgc gag ttc gtg      144
Ala Met Gly Trp Phe Arg Gln Ala Pro Gly Lys Glu Arg Glu Phe Val
        35                  40                  45

gcc gct atc cgt tgg agc gga ggc tct gcc tac tac gcc gat tct gtg      192
Ala Ala Ile Arg Trp Ser Gly Gly Ser Ala Tyr Tyr Ala Asp Ser Val
    50                  55                  60

aag ggc aga ttc acc atc agc aga gac aag gcc aag aac acc gtg tac      240
Lys Gly Arg Phe Thr Ile Ser Arg Asp Lys Ala Lys Asn Thr Val Tyr
65                  70                  75                  80

ctg cag atg aac agc ctg aag tac gag gac acc gcc gtg tac tac tgc      288
```

```
Leu Gln Met Asn Ser Leu Lys Tyr Glu Asp Thr Ala Val Tyr Tyr Cys
                85                  90                  95

gcc aga aca gag aat gtg cgg agc ctg ctg agc gac tac gcc acc tgg      336
Ala Arg Thr Glu Asn Val Arg Ser Leu Leu Ser Asp Tyr Ala Thr Trp
            100                 105                 110

cct tac gat tat tgg ggc cag ggc acc caa gtg acc gtt tct              378
Pro Tyr Asp Tyr Trp Gly Gln Gly Thr Gln Val Thr Val Ser
        115                 120                 125


<210> SEQ ID NO 32
<211> LENGTH: 126
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Glu Ser Gly Gly Gly Leu Met Gln Ala Gly Gly
1               5                   10                  15

Ser Leu Arg Leu Ser Cys Ala Val Ser Gly Arg Thr Phe Ser Thr Ala
            20                  25                  30

Ala Met Gly Trp Phe Arg Gln Ala Pro Gly Lys Glu Arg Glu Phe Val
        35                  40                  45

Ala Ala Ile Arg Trp Ser Gly Gly Ser Ala Tyr Tyr Ala Asp Ser Val
    50                  55                  60

Lys Gly Arg Phe Thr Ile Ser Arg Asp Lys Ala Lys Asn Thr Val Tyr
65                  70                  75                  80

Leu Gln Met Asn Ser Leu Lys Tyr Glu Asp Thr Ala Val Tyr Tyr Cys
                85                  90                  95

Ala Arg Thr Glu Asn Val Arg Ser Leu Leu Ser Asp Tyr Ala Thr Trp
            100                 105                 110

Pro Tyr Asp Tyr Trp Gly Gln Gly Thr Gln Val Thr Val Ser
        115                 120                 125


<210> SEQ ID NO 33
<211> LENGTH: 696
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(696)

<400> SEQUENCE: 33

gag cct aag agc tgc gac aag acc cac acc tgt cct cca tgt cct gct       48
Glu Pro Lys Ser Cys Asp Lys Thr His Thr Cys Pro Pro Cys Pro Ala
1               5                   10                  15

cca gaa ctg ctc ggc gga cct tcc gtg ttc ctg ttt cct cca aag cct       96
Pro Glu Leu Leu Gly Gly Pro Ser Val Phe Leu Phe Pro Pro Lys Pro
            20                  25                  30

aag gac acc ctg atg atc agc aga acc cct gaa gtg acc tgc gtg gtg      144
Lys Asp Thr Leu Met Ile Ser Arg Thr Pro Glu Val Thr Cys Val Val
        35                  40                  45

gtg gat gtg tcc cac gaa gat ccc gaa gtg aag ttc aat tgg tac gtg      192
Val Asp Val Ser His Glu Asp Pro Glu Val Lys Phe Asn Trp Tyr Val
    50                  55                  60

gac ggc gtg gaa gtg cac aac gcc aag acc aag cct aga gag gaa cag      240
Asp Gly Val Glu Val His Asn Ala Lys Thr Lys Pro Arg Glu Glu Gln
65                  70                  75                  80

tac aac agc acc tac aga gtg gtg tcc gtg ctg acc gtg ctg cac cag      288
```

```
Tyr Asn Ser Thr Tyr Arg Val Val Ser Val Leu Thr Val Leu His Gln
                85                  90                  95

gat tgg ctg aac ggc aaa gag tac aag tgc aag gtg tcc aac aag gcc      336
Asp Trp Leu Asn Gly Lys Glu Tyr Lys Cys Lys Val Ser Asn Lys Ala
            100                 105                 110

ctg cct gct cct atc gag aaa acc atc agc aag gcc aag ggc cag cct      384
Leu Pro Ala Pro Ile Glu Lys Thr Ile Ser Lys Ala Lys Gly Gln Pro
        115                 120                 125

agg gaa ccc cag gtt tac aca ctg cct cca agc cgg gaa gag atg acc      432
Arg Glu Pro Gln Val Tyr Thr Leu Pro Pro Ser Arg Glu Glu Met Thr
    130                 135                 140

aag aac cag gtg tcc ctg acc tgc ctg gtc aag ggc ttc tac cct tcc      480
Lys Asn Gln Val Ser Leu Thr Cys Leu Val Lys Gly Phe Tyr Pro Ser
145                 150                 155                 160

gat atc gcc gtg gaa tgg gag agc aat ggc cag cct gag aac aac tac      528
Asp Ile Ala Val Glu Trp Glu Ser Asn Gly Gln Pro Glu Asn Asn Tyr
                165                 170                 175

aag aca acc cct cct gtg ctg gac agc gac ggc tca ttc ttc ctg tat      576
Lys Thr Thr Pro Pro Val Leu Asp Ser Asp Gly Ser Phe Phe Leu Tyr
            180                 185                 190

agc aag ctg aca gtg gac aag agc aga tgg cag cag ggc aac gtg ttc      624
Ser Lys Leu Thr Val Asp Lys Ser Arg Trp Gln Gln Gly Asn Val Phe
        195                 200                 205

agc tgc agc gtg atg cac gag gcc ctg cac aac cac tac acc cag aag      672
Ser Cys Ser Val Met His Glu Ala Leu His Asn His Tyr Thr Gln Lys
    210                 215                 220

tcc ctg agc ctg tct cct ggc aag                                      696
Ser Leu Ser Leu Ser Pro Gly Lys
225                 230


<210> SEQ ID NO 34
<211> LENGTH: 232
<212> TYPE: PRT
<213> ORGANISM: Artificial Sequence
<220> FEATURE:
<223> OTHER INFORMATION: Synthetic Construct

<400> SEQUENCE: 34

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160
```

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
        180                 185                 190

Ser Lys Leu Thr Val Asp Lys Ser Arg Trp Gln Gln Gly Asn Val Phe
    195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 35
<211> LENGTH: 186
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(186)

<400> SEQUENCE: 35 gag cct aag atc cct cag cct cag cca aag cct caa cca caa ccg cag       48
Glu Pro Lys Ile Pro Gln Pro Gln Pro Lys Pro Gln Pro Gln Pro Gln
1               5                   10                  15 cca cag cct aaa ccg cag cct aag cca gag cct gag cag cgg atg aag       96
Pro Gln Pro Lys Pro Gln Pro Lys Pro Glu Pro Glu Gln Arg Met Lys
                20                  25                  30 cag atc gag gac aag atc gaa gag atc ctg agc aaa atc tac cac atc      144
Gln Ile Glu Asp Lys Ile Glu Glu Ile Leu Ser Lys Ile Tyr His Ile
            35                  40                  45 gag aac gag atc gcc cgg atc aag aag ctc gtc ggc gaa aga              186
Glu Asn Glu Ile Ala Arg Ile Lys Lys Leu Val Gly Glu Arg
        50                  55                  60

<210> SEQ ID NO 36
<211> LENGTH: 62
<212> TYPE: PRT
<213> ORGANISM: Artificial Sequence
<220> FEATURE:
<223> OTHER INFORMATION: Synthetic Construct

<400> SEQUENCE: 36

Glu Pro Lys Ile Pro Gln Pro Gln Pro Lys Pro Gln Pro Gln Pro Gln
1               5                   10                  15

Pro Gln Pro Lys Pro Gln Pro Lys Pro Glu Pro Glu Gln Arg Met Lys
                20                  25                  30

Gln Ile Glu Asp Lys Ile Glu Glu Ile Leu Ser Lys Ile Tyr His Ile
            35                  40                  45

Glu Asn Glu Ile Ala Arg Ile Lys Lys Leu Val Gly Glu Arg
        50                  55                  60

<210> SEQ ID NO 37
<211> LENGTH: 9
<212> TYPE: DNA
<213> ORGANISM: Artificial Sequence
<220> FEATURE:
<223> OTHER INFORMATION: Sythetic
<220> FEATURE:
<221> NAME/KEY: CDS
<222> LOCATION: (1)..(9)

<400> SEQUENCE: 37

```
ggc gcg cct                                                        9
Gly Ala Pro
1


<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Gly Ala Pro
1


<210> SEQ ID NO 39
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(66)

<400> SEQUENCE: 39

ggt ggt acc agc gga ggc gga gga tca ggt ggc gga ggt agt ggt ggt       48
Gly Gly Thr Ser Gly Gly Gly Gly Ser Gly Gly Gly Gly Ser Gly Gly
1               5                   10                  15

ggc ggt agc gcg gcc gcc                                               66
Gly Gly Ser Ala Ala Ala
            20


<210> SEQ ID NO 40
<211> LENGTH: 22
<212> TYPE: PRT
<213> ORGANISM: Artificial Sequence
<220> FEATURE:
<223> OTHER INFORMATION: Synthetic Construct

<400> SEQUENCE: 40

Gly Gly Thr Ser Gly Gly Gly Gly Ser Gly Gly Gly Gly Ser Gly Gly
1               5                   10                  15

Gly Gly Ser Ala Ala Ala
            20


<210> SEQ ID NO 41
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(42)

<400> SEQUENCE: 41

gaa ttc ggc gga ggc agc ggc ggt gga agc ggc gga ggc tct               42
Glu Phe Gly Gly Gly Ser Gly Gly Gly Ser Gly Gly Gly Ser
1               5                   10


<210> SEQ ID NO 42
<211> LENGTH: 14
<212> TYPE: PRT
<213> ORGANISM: Artificial Sequence
<220> FEATURE:
<223> OTHER INFORMATION: Synthetic Construct
```

<400> SEQUENCE: 42

Glu Phe Gly Gly Gly Ser Gly Gly Gly Ser Gly Gly Gly Ser
1 5 10

<210> SEQ ID NO 43
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(45)

<400> SEQUENCE: 43 atc ccg cgg ggt ggt ggt agt ggc gga gga agt ggt ggc gga tct 45
Ile Pro Arg Gly Gly Gly Ser Gly Gly Gly Ser Gly Gly Gly Ser
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

Ile Pro Arg Gly Gly Gly Ser Gly Gly Gly Ser Gly Gly Gly Ser
1 5 10 15

<210> SEQ ID NO 45
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(63)

<400> SEQUENCE: 45 gaa ttc tct ggc ggc gga gga tct ggc gga ggt gga agc gga ggc ggt 48
Glu Phe Ser Gly Gly Gly Gly Ser Gly Gly Gly Gly Ser Gly Gly Gly
1 5 10 15 gga tct gcg gcc gcc 63
Gly Ser Ala Ala Ala
20

<210> SEQ ID NO 46
<211> LENGTH: 21
<212> TYPE: PRT
<213> ORGANISM: Artificial Sequence
<220> FEATURE:
<223> OTHER INFORMATION: Synthetic Construct

<400> SEQUENCE: 46

Glu Phe Ser Gly Gly Gly Gly Ser Gly Gly Gly Gly Ser Gly Gly Gly
1 5 10 15

Gly Ser Ala Ala Ala
20

<210> SEQ ID NO 47
<211> LENGTH: 9
<212> TYPE: DNA
<213> ORGANISM: Artificial Sequence
<220> FEATURE:
<223> OTHER INFORMATION: Synthetic

```
<220> FEATURE:
<221> NAME/KEY: CDS
<222> LOCATION: (1)..(9)

<400> SEQUENCE: 47

agc ggt acc                                                            9
Ser Gly Thr
1


<210> SEQ ID NO 48
<211> LENGTH: 3
<212> TYPE: PRT
<213> ORGANISM: Artificial Sequence
<220> FEATURE:
<223> OTHER INFORMATION: Synthetic

<400> SEQUENCE: 48

Ser Gly Thr
1


<210> SEQ ID NO 49
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(45)

<400> SEQUENCE: 49

ggt gaa ttc ggc gga ggc agc ggc ggt gga agc ggc gga ggc tct           45
Gly Glu Phe Gly Gly Gly Ser Gly Gly Gly Ser Gly Gly Gly Ser
1               5                   10                  15


<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

Gly Glu Phe Gly Gly Gly Ser Gly Gly Gly Ser Gly Gly Gly Ser
1               5                   10                  15


<210> SEQ ID NO 51
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(51)

<400> SEQUENCE: 51

ggt ggc gga gga agc gga ggc gga gga tca ggt ggc ggt gga tct atc       48
Gly Gly Gly Gly Ser Gly Gly Gly Gly Ser Gly Gly Gly Gly Ser Ile
1               5                   10                  15

gat                                                                   51
Asp


<210> SEQ ID NO 52
<211> LENGTH: 17
<212> TYPE: PRT
<213> ORGANISM: Artificial Sequence
<220> FEATURE:
```

<223> OTHER INFORMATION: Synthetic Construct

<400> SEQUENCE: 52

Gly Gly Gly Gly Ser Gly Gly Gly Gly Ser Gly Gly Gly Gly Ser Ile
1 5 10 15

Asp

<210> SEQ ID NO 53
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(60)

<400> SEQUENCE: 53 agc ggt acc ggc gga ggt gga agc gga ggc gga ggc tct ggc ggc ggt 48
Ser Gly Thr Gly Gly Gly Gly Ser Gly Gly Gly Gly Ser Gly Gly Gly
1 5 10 15 gga tct gga tcc 60
Gly Ser Gly Ser
20

<210> SEQ ID NO 54
<211> LENGTH: 20
<212> TYPE: PRT
<213> ORGANISM: Artificial Sequence
<220> FEATURE:
<223> OTHER INFORMATION: Synthetic Construct

<400> SEQUENCE: 54

Ser Gly Thr Gly Gly Gly Gly Ser Gly Gly Gly Gly Ser Gly Gly Gly
1 5 10 15

Gly Ser Gly Ser
20

<210> SEQ ID NO 55
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(48)

<400> SEQUENCE: 55 ccg cgg ggt ggt ggt tcc ggc gga ggt agt ggc ggc gga tct gcg gcc 48
Pro Arg Gly Gly Gly Ser Gly Gly Gly Ser Gly Gly Gly Ser Ala Ala
1 5 10 15

<210> SEQ ID NO 56
<211> LENGTH: 16
<212> TYPE: PRT
<213> ORGANISM: Artificial Sequence
<220> FEATURE:
<223> OTHER INFORMATION: Synthetic Construct

<400> SEQUENCE: 56

Pro Arg Gly Gly Gly Ser Gly Gly Gly Ser Gly Gly Gly Ser Ala Ala
1 5 10 15

<210> SEQ ID NO 57
<211> LENGTH: 30

```
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(30)

<400> SEQUENCE: 57

gcg tgg agc cac ccg cag ttc gag aaa tga                               30
Ala Trp Ser His Pro Gln Phe Glu Lys
1               5


<210> SEQ ID NO 58
<211> LENGTH: 9
<212> TYPE: PRT
<213> ORGANISM: Artificial Sequence
<220> FEATURE:
<223> OTHER INFORMATION: Synthetic Construct

<400> SEQUENCE: 58

Ala Trp Ser His Pro Gln Phe Glu Lys
1               5


<210> SEQ ID NO 59
<211> LENGTH: 90
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(90)

<400> SEQUENCE: 59

gct tgg agc cac ccg cag ttc gaa aaa ggt gga ggt tct ggc ggt gga       48
Ala Trp Ser His Pro Gln Phe Glu Lys Gly Gly Gly Ser Gly Gly Gly
1               5                   10                  15

tcg gga ggt tca gcg tgg agc cac ccg cag ttc gag aaa tga               90
Ser Gly Gly Ser Ala Trp Ser His Pro Gln Phe Glu Lys
            20                  25


<210> SEQ ID NO 60
<211> LENGTH: 29
<212> TYPE: PRT
<213> ORGANISM: Artificial Sequence
<220> FEATURE:
<223> OTHER INFORMATION: Synthetic Construct

<400> SEQUENCE: 60

Ala Trp Ser His Pro Gln Phe Glu Lys Gly Gly Gly Ser Gly Gly Gly
1               5                   10                  15

Ser Gly Gly Ser Ala Trp Ser His Pro Gln Phe Glu Lys
            20                  25


<210> SEQ ID NO 61
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(21)

<400> SEQUENCE: 61

cac cac cac cac cac cac tga                                           21
His His His His His His
```

-continued

```
1               5


<210> SEQ ID NO 62
<211> LENGTH: 6
<212> TYPE: PRT
<213> ORGANISM: Artificial Sequence
<220> FEATURE:
<223> OTHER INFORMATION: Synthetic Construct

<400> SEQUENCE: 62

His His His His His His
1               5


<210> SEQ ID NO 63
<211> LENGTH: 75
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(75)

<400> SEQUENCE: 63

cac cac cac cac cac cac ggt gga ggt tct ggc ggt gga tcg gga ggt       48
His His His His His His Gly Gly Gly Ser Gly Gly Gly Ser Gly Gly
1               5                   10                  15

tca cat cac cat cac cat cac ggt tga                                   75
Ser His His His His His His Gly
            20


<210> SEQ ID NO 64
<211> LENGTH: 24
<212> TYPE: PRT
<213> ORGANISM: Artificial Sequence
<220> FEATURE:
<223> OTHER INFORMATION: Synthetic Construct

<400> SEQUENCE: 64

His His His His His His Gly Gly Gly Ser Gly Gly Gly Ser Gly Gly
1               5                   10                  15

Ser His His His His His His Gly
            20


<210> SEQ ID NO 65
<211> LENGTH: 367
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(366)

<400> SEQUENCE: 65

caa gtt cag ctt caa gaa tct ggc ggc gga agc gtt cag gct ggc gga       48
Gln Val Gln Leu Gln Glu Ser Gly Gly Gly Ser Val Gln Ala Gly Gly
1               5                   10                  15

tct ctg aga ctg agc tgt gtg gcc agc ggc tac acc gat agc aca tac       96
Ser Leu Arg Leu Ser Cys Val Ala Ser Gly Tyr Thr Asp Ser Thr Tyr
            20                  25                  30

tgc gtc ggc tgg ttc aga cag gcc cct ggc aaa gag aga gag ggc gtc      144
Cys Val Gly Trp Phe Arg Gln Ala Pro Gly Lys Glu Arg Glu Gly Val
        35                  40                  45

gcc aga atc aac acc atc agc ggc aga cct tgg tac gcc gac tct gtg      192
Ala Arg Ile Asn Thr Ile Ser Gly Arg Pro Trp Tyr Ala Asp Ser Val
```

```
    50                  55                  60

aag ggc aga ttc aca atc agc cag gac aac agc aag aac acc gtg ttc      240
Lys Gly Arg Phe Thr Ile Ser Gln Asp Asn Ser Lys Asn Thr Val Phe
65                  70                  75                  80

ctg cag atg aac agc ctg aag cct gag gac acc gcc atc tac tac tgc      288
Leu Gln Met Asn Ser Leu Lys Pro Glu Asp Thr Ala Ile Tyr Tyr Cys
                85                  90                  95

acc ctg acc acc gcc aac agc aga ggc ttt tgt tcc ggc ggc tac aac      336
Thr Leu Thr Thr Ala Asn Ser Arg Gly Phe Cys Ser Gly Gly Tyr Asn
            100                 105                 110

tac aaa ggc cag ggc caa gtg acc gtg tct g                            367
Tyr Lys Gly Gln Gly Gln Val Thr Val Ser
        115                 120
```

<210> SEQ ID NO 66
<211> LENGTH: 122
<212> TYPE: PRT
<213> ORGANISM: Artificial Sequence
<220> FEATURE:
<223> OTHER INFORMATION: Synthetic Construct

<400> SEQUENCE: 66

```
Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Asp Ser Thr Tyr
            20                  25                  30

Cys Val Gly Trp Phe Arg Gln Ala Pro Gly Lys Glu Arg Glu Gly Val
        35                  40                  45

Ala Arg Ile Asn Thr Ile Ser Gly Arg Pro Trp Tyr Ala Asp Ser Val
    50                  55                  60

Lys Gly Arg Phe Thr Ile Ser Gln Asp Asn Ser Lys Asn Thr Val Phe
65                  70                  75                  80

Leu Gln Met Asn Ser Leu Lys Pro Glu Asp Thr Ala Ile Tyr Tyr Cys
                85                  90                  95

Thr Leu Thr Thr Ala Asn Ser Arg Gly Phe Cys Ser Gly Gly Tyr Asn
            100                 105                 110

Tyr Lys Gly Gln Gly Gln Val Thr Val Ser
        115                 120
```

<210> SEQ ID NO 67
<211> LENGTH: 29811
<212> TYPE: DNA
<213> ORGANISM: SARS-CoV-2

<400> SEQUENCE: 67

```
cttcccaggt aacaaaccaa ccaactttcg atctcttgta gatctgttct ctaaacgaac      60

tttaaaatct gtgtggctgt cactcggctg catgcttagt gcactcacgc agtataatta     120

ataactaatt actgtcgttg acaggacacg agtaactcgt ctatcttctg caggctgctt     180

acggtttcgt ccgtgttgca gccgatcatc agcacatcta ggtttcgtcc gggtgtgacc     240

gaaaggtaag atggagagcc ttgtccctgg tttcaacgag aaaacacacg tccaactcag     300

tttgcctgtt ttacaggttc gcgacgtgct cgtacgtggc tttggagact ccgtggagga     360

ggtcttatca gaggcacgtc aacatcttaa agatggcact tgtggcttag tagaagttga     420

aaaaggcgtt ttgcctcaac ttgaacagcc ctatgtgttc atcaaacgtt cggatgctcg     480

aactgcacct catggtcatg ttatggttga gctggtagca gaactcgaag gcattcagta     540

cggtcgtagt ggtgagacac ttggtgtcct tgtccctcat gtgggcgaaa taccagtggc     600
```

```
ttaccgcaag gttcttcttc gtaagaacgg taataaagga gctggtggcc atagttacgg    660
cgccgatcta aagtcatttg acttaggcga cgagcttggc actgatcctt atgaagattt    720
tcaagaaaac tggaacacta aacatagcag tggtgttacc cgtgaactca tgcgtgagct    780
taacggaggg gcatacactc gctatgtcga taacaacttc tgtggccctg atggctaccc    840
tcttgagtgc attaaagacc ttctagcacg tgctggtaaa gcttcatgca ctttgtccga    900
acaactggac tttattgaca ctaagagggg tgtatactgc tgccgtgaac atgagcatga    960
aattgcttgg tacacggaac gttctgaaaa gagctatgaa ttgcagacac cttttgaaat   1020
taaattggca aagaaatttg acaccttcaa tggggaatgt ccaaattttg tatttccctt   1080
aaattccata atcaagacta ttcaaccaag ggttgaaaag aaaaagcttg atggctttat   1140
gggtagaatt cgatctgtct atccagttgc gtcaccaaat gaatgcaacc aaatgtgcct   1200
ttcaactctc atgaagtgtg atcattgtgg tgaaacttca tggcagacgg gcgattttgt   1260
taaagccact tgcgaatttt gtggcactga gaatttgact aaagaaggtg ccactacttg   1320
tggttactta ccccaaaatg ctgttgttaa aatttattgt ccagcatgtc acaattcaga   1380
agtaggacct gagcatagtc ttgccgaata ccataatgaa tctggcttga aaaccattct   1440
tcgtaagggt ggtcgcacta ttgcctttgg aggctgtgtg ttctcttatg ttggttgcca   1500
taacaagtgt gcctattggg ttccacgtgc tagcgctaac ataggttgta accatacagg   1560
tgttgttgga gaaggttccg aaggtcttaa tgacaacctt cttgaaatac tccaaaaaga   1620
gaaagtcaac atcaatattg ttggtgactt taaacttaat gaagagatcg ccattatttt   1680
ggcatctttt tctgcttcca caagtgcttt tgtggaaact gtgaaaggtt tggattataa   1740
agcattcaaa caaattgttg aatcctgtgg taattttaaa gttacaaaag gaaaagctaa   1800
aaaaggtgcc tggaatattg gtgaacagaa atcaatactg agtcctcttt atgcatttgc   1860
atcagaggct gctcgtgttg tacgatcaat tttctcccgc actcttgaaa ctgctcaaaa   1920
ttctgtgcgt gttttacaga aggccgctat aacaatacta gatggaattt cacagtattc   1980
actgagactc attgatgcta tgatgttcac atctgatttg gctactaaca atctagttgt   2040
aatggcctac attacaggtg gtgttgttca gttgacttcg cagtggctaa ctaacatctt   2100
tggcactgtt tatgaaaaac tcaaacccgt ccttgattgg cttgaagaga agtttaagga   2160
aggtgtagag tttcttagag acggttggga aattgttaaa tttatctcaa cctgtgcttg   2220
tgaaattgtc ggtggacaaa ttgtcacctg tgcaaaggaa attaaggaga gtgttcagac   2280
attctttaag cttgtaaata aatttttggc tttgtgtgct gactctatca ttattggtgg   2340
agctaaactt aaagccttga atttaggtga aacatttgtc acgcactcaa agggattgta   2400
cagaaagtgt gttaaatcca gagaagaaac tggcctactc atgcctctaa aagccccaaa   2460
agaaattatc ttcttagagg gagaaacact tcccacagaa gtgttaacag aggaagttgt   2520
cttgaaaact ggtgatttac aaccattaga acaacctact agtgaagctg ttgaagctcc   2580
attggttggt acaccagttt gtattaacgg gcttatgttg ctcgaaatca aagacacaga   2640
aaagtactgt gcccttgcac ctaatatgat ggtaacaaac aataccttca cactcaaagg   2700
cggtgcacca acaaaggtta cttttggtga tgacactgtg atagaagtgc aaggttacaa   2760
gagtgtgaat atcacttttg aacttgatga aaggattgat aaagtactta atgagaagtg   2820
ctctgcctat acagttgaac tcggtacaga agtaaatgag ttcgcctgtg ttgtggcaga   2880
tgctgtcata aaaactttgc aaccagtatc tgaattactt acaccactgg gcattgattt   2940
```

-continued

```
agatgagtgg agtatggcta catactactt atttgatgag tctggtgagt ttaaattggc   3000

ttcacatatg tattgttctt tctaccctcc agatgaggat gaagaagaag gtgattgtga   3060

agaagaagag tttgagccat caactcaata tgagtatggt actgaagatg attaccaagg   3120

taaacctttg gaatttggtg ccacttctgc tgctcttcaa cctgaagaag agcaagaaga   3180

agattggtta gatgatgata gtcaacaaac tgttggtcaa caagacggca gtgaggacaa   3240

tcagacaact actattcaaa caattgttga ggttcaacct caattagaga tggaacttac   3300

accagttgtt cagactattg aagtgaatag ttttagtggt tatttaaaac ttactgacaa   3360

tgtatacatt aaaaatgcag acattgtgga agaagctaaa aaggtaaaac caacagtggt   3420

tgttaatgca gccaatgttt accttaaaca tggaggaggt gttgcaggag ccttaaataa   3480

ggctactaac aatgccatgc aagttgaatc tgatgattac atagctacta atggaccact   3540

taaagtgggt ggtagttgtg ttttaagcgg acacaatctt gctaaacact gtcttcatgt   3600

tgtcggccca aatgttaaca aaggtgaaga cattcaactt cttaagagtg cttatgaaaa   3660

ttttaatcag cacgaagttc tacttgcacc attattatca gctggtattt ttggtgctga   3720

ccctatacat tctttaagag tttgtgtaga tactgttcgc acaaatgtct acttagctgt   3780

ctttgataaa aatctctatg acaaacttgt ttcaagcttt ttggaaatga agagtgaaaa   3840

gcaagttgaa caaaagatcg ctgagattcc taaagaggaa gttaagccat ttataactga   3900

aagtaaacct tcagttgaac agagaaaaca agatgataag aaaatcaaag cttgtgttga   3960

agaagttaca acaactctgg aagaaactaa gttcctcaca gaaaacttgt tactttatat   4020

tgacattaat ggcaatcttc atccagattc tgccactctt gttagtgaca ttgacatcac   4080

tttcttaaag aaagatgctc catatatagt gggtgatgtt gttcaagagg gtgttttaac   4140

tgctgtggtt atacctacta aaaaggctgg tggcactact gaaatgctag cgaaagcttt   4200

gagaaaagtg ccaacagaca attatataac cacttacccg ggtcagggtt taaatggtta   4260

cactgtagag gaggcaaaga cagtgcttaa aaagtgtaaa agtgcctttt acattctacc   4320

atctattatc tctaatgaga agcaagaaat tcttggaact gtttcttgga atttgcgaga   4380

aatgcttgca catgcagaag aaacacgcaa attaatgcct gtctgtgtgg aaactaaagc   4440

catagtttca actatacagc gtaaatataa gggtattaaa atacaagagg gtgtggttga   4500

ttatggtgct agattttact tttacaccag taaaacaact gtagcgtcac ttatcaacac   4560

acttaacgat ctaaatgaaa ctcttgttac aatgccactt ggctatgtaa cacatggctt   4620

aaatttggaa gaagctgctc ggtatatgag atctctcaaa gtgccagcta cagtttctgt   4680

ttcttcacct gatgctgtta cagcgtataa tggttatctt acttcttctt ctaaaacacc   4740

tgaagaacat tttattgaaa ccatctcact tgctggttcc tataaagatt ggtcctattc   4800

tggacaatct acacaactag gtatagaatt tcttaagaga ggtgataaaa gtgtatatta   4860

cactagtaat cctaccacat tccacctaga tggtgaagtt atcacctttg acaatcttaa   4920

gacacttctt tctttgagag aagtgaggac tattaaggtg tttacaacag tagacaacat   4980

taacctccac acgcaagttg tggacatgtc aatgacatat ggacaacagt ttggtccaac   5040

ttatttggat ggagctgatg ttactaaaat aaaacctcat aattcacatg aaggtaaaac   5100

attttatgtt ttacctaatg atgacactct acgtgttgag gcttttgagt actaccacac   5160

aactgatcct agttttctgg gtaggtacat gtcagcatta aatcacacta aaaagtggaa   5220

atacccacaa gttaatggtt taacttctat taaatgggca gataacaact gttatcttgc   5280

cactgcattg ttaacactcc aacaaataga gttgaagttt aatccacctg ctctacaaga   5340
```

```
tgcttattac agagcaaggg ctggtgaagc tgctaacttt tgtgcactta tcttagccta   5400
ctgtaataag acagtaggtg agttaggtga tgttagagaa acaatgagtt acttgtttca   5460
acatgccaat ttagattctt gcaaaagagt cttgaacgtg gtgtgtaaaa cttgtggaca   5520
acagcagaca acccttaagg gtgtagaagc tgttatgtac atgggcacac tttcttatga   5580
acaatttaag aaaggtgttc agataccttg tacgtgtggt aaacaagcta caaaatatct   5640
agtacaacag gagtcacctt ttgttatgat gtcagcacca cctgctcagt atgaacttaa   5700
gcatggtaca tttacttgtg ctagtgagta cactggtaat taccagtgtg gtcactataa   5760
acatataact tctaaagaaa ctttgtattg catagacggt gctttactta caaagtcctc   5820
agaatacaaa ggtcctatta cggatgtttt ctacaaagaa aacagttaca caacaaccat   5880
aaaaccagtt acttataaat tggatggtgt tgtttgtaca gaaattgacc ctaagttgga   5940
caattattat aagaaagaca attcttattt cacagagcaa ccaattgatc ttgtaccaaa   6000
ccaaccatat ccaaacgcaa gcttcgataa ttttaagttt gtatgtgata atatcaaatt   6060
tgctgatgat ttaaaccagt taactggtta taagaaacct gcttcaagag agcttaaagt   6120
tacatttttc cctgacttaa atggtgatgt ggtggctatt gattataaac actacacacc   6180
ctcttttaag aaaggagcta aattgttaca taaacctatt gtttggcatg ttaacaatgc   6240
aactaataaa gccacgtata aaccaaatac ctggtgtata cgttgtcttt ggagcacaaa   6300
accagttgaa acatcaaatt cgtttgatgt actgaagtca gaggacgcgc agggaatgga   6360
taatcttgcc tgcgaagatc taaaaccagt ctctgaagaa gtagtggaaa atcctaccat   6420
acagaaagac gttcttgagt gtaatgtgaa aactaccgaa gttgtaggag acattatact   6480
taaaccagca aataatagtt taaaaattac agaagaggtt ggccacacag atctaatggc   6540
tgcttatgta gacaattcta gtcttactat taagaaacct aatgaattat ctagagtatt   6600
aggtttgaaa acccttgcta ctcatggttt agctgctgtt aatagtgtcc cttgggatac   6660
tatagctaat tatgctaagc cttttcttaa caaagttgtt agtacaacta ctaacatagt   6720
tacacggtgt ttaaaccgtg tttgtactaa ttatatgcct tatttcttta ctttattgct   6780
acaattgtgt acttttacta gaagtacaaa ttctagaatt aaagcatcta tgccgactac   6840
tatagcaaag aatactgtta agagtgtcgg taaattttgt ctagaggctt catttaatta   6900
tttgaagtca cctaattttt ctaaactgat aaatattata atttggtttt tactattaag   6960
tgtttgccta ggttctttaa tctactcaac cgctgcttta ggtgttttaa tgtctaattt   7020
aggcatgcct tcttactgta ctggttacag agaaggctat ttgaactcta ctaatgtcac   7080
tattgcaacc tactgtactg gttctatacc ttgtagtgtt tgtcttagtg gtttagattc   7140
tttagacacc tatccttctt tagaaactat acaaattacc atttcatctt ttaaatggga   7200
tttaactgct tttggcttag ttgcagagtg gtttttggca tatattcttt tcactaggtt   7260
tttctatgta cttggattgg ctgcaatcat gcaattgttt ttcagctatt ttgcagtaca   7320
ttttattagt aattcttggc ttatgtggtt aataattaat cttgtacaaa tggccccgat   7380
ttcagctatg gttagaatgt acatcttctt tgcatcattt tattatgtat ggaaaagtta   7440
tgtgcatgtt gtagacggtt gtaattcatc aacttgtatg atgtgttaca aacgtaatag   7500
agcaacaaga gtcgaatgta caactattgt taatggtgtt agaaggtcct tttatgtcta   7560
tgctaatgga ggtaaaggct tttgcaaact acacaattgg aattgtgtta attgtgatac   7620
attctgtgct ggtagtacat ttattagtga tgaagttgcg agagacttgt cactacagtt   7680
```

-continued

```
taaaagacca ataaatccta ctgaccagtc ttcttacatc gttgatagtg ttacagtgaa   7740
gaatggttcc atccatcttt actttgataa agctggtcaa aagacttatg aaagacattc   7800
tctctctcat tttgttaact tagacaacct gagagctaat aacactaaag gttcattgcc   7860
tattaatgtt atagtttttg atggtaaatc aaaatgtgaa gaatcatctg caaaatcagc   7920
gtctgtttac tacagtcagc ttatgtgtca acctatactg ttactagatc aggcattagt   7980
gtctgatgtt ggtgatagtg cggaagttgc agttaaaatg tttgatgctt acgttaatac   8040
gttttcatca actttttaacg taccaatgga aaaactcaaa acactagttg caactgcaga   8100
agctgaactt gcaaagaatg tgtccttaga caatgtctta tctactttta tttcagcagc   8160
tcggcaaggg tttgttgatt cagatgtaga aactaaagat gttgttgaat gtcttaaatt   8220
gtcacatcaa tctgacatag aagttactgg cgatagttgt aataactata tgctcaccta   8280
taacaaagtt gaaaacatga caccccgtga ccttggtgct tgtattgact gtagtgcgcg   8340
tcatattaat gcgcaggtag caaaaagtca caacattgct ttgatatgga acgttaaaga   8400
tttcatgtca ttgtctgaac aactacgaaa acaaatacgt agtgctgcta aaaagaataa   8460
cttacctttt aagttgacat gtgcaactac tagacaagtt gttaatgttg taacaacaaa   8520
gatagcactt aagggtggta aaattgttaa taattggttg aagcagttaa ttaaagttac   8580
acttgtgttc ctttttgttg ctgctatttt ctatttaata acacctgttc atgtcatgtc   8640
taaacatact gacttttcaa gtgaaatcat aggatacaag gctattgatg gtggtgtcac   8700
tcgtgacata gcatctacag atacttgttt tgctaacaaa catgctgatt ttgacacatg   8760
gtttagccag cgtggtggta gttatactaa tgacaaagct tgcccattga ttgctgcagt   8820
cataacaaga gaagtgggtt ttgtcgtgcc tggtttgcct ggcacgatat tacgcacaac   8880
taatggtgac tttttgcatt tcttacctag agtttttagt gcagttggta acatctgtta   8940
cacaccatca aaacttatag agtacactga ctttgcaaca tcagcttgtg ttttggctgc   9000
tgaatgtaca atttttaaag atgcttctgg taagccagta ccatattgtt atgataccaa   9060
tgtactagaa ggttctgttg cttatgaaag tttacgccct gacacacgtt atgtgctcat   9120
ggatggctct attattcaat ttcctaacac ctaccttgaa ggttctgtta gagtggtaac   9180
aacttttgat tctgagtact gtaggcacgg cacttgtgaa agatcagaag ctggtgtttg   9240
tgtatctact agtggtagat gggtacttaa caatgattat tacagatctt taccaggagt   9300
tttctgtggt gtagatgctg taaatttact tactaatatg tttacaccac taattcaacc   9360
tattggtgct ttggacatat cagcatctat agtagctggt ggtattgtag ctatcgtagt   9420
aacatgcctt gcctactatt ttatgaggtt tagaagagct tttggtgaat acagtcatgt   9480
agttgccttt aatactttac tattccttat gtcattcact gtactctgtt taacaccagt   9540
ttactcattc ttacctggtg tttattctgt tatttacttg tacttgacat tttatcttac   9600
taatgatgtt tctttttttag cacatattca gtggatggtt atgttcacac ctttagtacc   9660
tttctggata acaattgctt atatcatttg tatttccaca aagcatttct attggttctt   9720
tagtaattac ctaaagagac gtgtagtctt taatggtgtt tcctttagta cttttgaaga   9780
agctgcgctg tgcacctttt tgttaaataa agaaatgtat ctaaagttgc gtagtgatgt   9840
gctattacct cttacgcaat ataatagata cttagctctt tataataagt acaagtattt   9900
tagtggagca atggatacaa ctagctacag agaagctgct tgttgtcatc tcgcaaaggc   9960
tctcaatgac ttcagtaact caggttctga tgttctttac caaccaccac aaacctctat  10020
cacctcagct gttttgcaga gtggttttag aaaaatggca ttcccatctg gtaaagttga  10080
```

-continued

```
gggttgtatg gtacaagtaa cttgtggtac aactacactt aacggtcttt ggcttgatga  10140
cgtagtttac tgtccaagac atgtgatctg cacctctgaa gacatgctta accctaatta  10200
tgaagattta ctcattcgta agtctaatca taatttcttg gtacaggctg gtaatgttca  10260
actcagggtt attggacatt ctatgcaaaa ttgtgtactt aagcttaagg ttgatacagc  10320
caatcctaag acacctaagt ataagtttgt tcgcattcaa ccaggacaga ctttttcagt  10380
gttagcttgt tacaatggtt caccatctgg tgtttaccaa tgtgctatga ggcccaattt  10440
cactattaag ggttcattcc ttaatggttc atgtggtagt gttggtttta acatagatta  10500
tgactgtgtc tctttttgtt acatgcacca tatggaatta ccaactggag ttcatgctgg  10560
cacagactta gaaggtaact tttatggacc ttttgttgac aggcaaacag cacaagcagc  10620
tggtacggac acaactatta cagttaatgt tttagcttgg ttgtacgctg ctgttataaa  10680
tggagacagg tggtttctca atcgatttac cacaactctt aatgacttta accttgtggc  10740
tatgaagtac aattatgaac ctctaacaca agaccatgtt gacatactag gacctctttc  10800
tgctcaaact ggaattgccg ttttagatat gtgtgcttca ttaaaagaat tactgcaaaa  10860
tggtatgaat ggacgtacca tattgggtag tgctttatta gaagatgaat ttacaccttt  10920
tgatgttgtt agacaatgct caggtgttac tttccaaagt gcagtgaaaa gaacaatcaa  10980
gggtacacac cactggttgt tactcacaat tttgacttca cttttagttt tagtccagag  11040
tactcaatgg tctttgttct ttttttgta tgaaaatgcc tttttacctt ttgctatggg  11100
tattattgct atgtctgctt ttgcaatgat gtttgtcaaa cataagcatg catttctctg  11160
tttgtttttg ttaccttctc ttgccactgt agcttatttt aatatggtct atatgcctgc  11220
tagttgggtg atgcgtatta tgacatggtt ggatatggtt gatactagtt tgtctggttt  11280
taagctaaaa gactgtgtta tgtatgcatc agctgtagtg ttactaatcc ttatgacagc  11340
aagaactgtg tatgatgatg gtgctaggag agtgtggaca cttatgaatg tcttgacact  11400
cgtttataaa gtttattatg gtaatgcttt agatcaagcc atttccatgt gggctcttat  11460
aatctctgtt acttctaact actcaggtgt agttacaact gtcatgtttt tggccagagg  11520
tattgttttt atgtgtgttg agtattgccc tattttcttc ataactggta atacacttca  11580
gtgtataatg ctagtttatt gtttcttagg ctatttttgt acttgttact ttggcctctt  11640
ttgtttactc aaccgctact ttagactgac tcttggtgtt tatgattact tagtttctac  11700
acaggagttt agatatatga attcacaggg actactccca cccaagaata gcatagatgc  11760
cttcaaactc aacattaaat tgttgggtgt tggtggcaaa ccttgtatca aagtagccac  11820
tgtacagtct aaaatgtcag atgtaaagtg cacatcagta gtcttactct cagttttgca  11880
acaactcaga gtagaatcat catctaaatt gtgggctcaa tgtgtccagt tacacaatga  11940
cattctctta gctaaagata ctactgaagc ctttgaaaaa atggtttcac tactttctgt  12000
tttgctttcc atgcagggtg ctgtagacat aaacaagctt tgtgaagaaa tgctggacaa  12060
cagggcaacc ttacaagcta tagcctcaga gtttagttcc cttccatcat atgcagcttt  12120
tgctactgct caagaagctt atgagcaggc tgttgctaat ggtgattctg aagttgttct  12180
taaaaagttg aagaagtctt tgaatgtggc taaatctgaa tttgaccgtg atgcagccat  12240
gcaacgtaag ttggaaaaga tggctgatca agctatgacc caaatgtata aacaggctag  12300
atctgaggac aagagggcaa aagttactag tgctatgcag acaatgcttt tcactatgct  12360
tagaaagttg gataatgatg cactcaacaa cattatcaac aatgcaagag atggttgtgt  12420
```

-continued

```
tcccttgaac ataatacctc ttacaacagc agccaaacta atggttgtca taccagacta  12480
taacacatat aaaaatacgt gtgatggtac aacatttact tatgcatcag cattgtggga  12540
aatccaacag gttgtagatg cagatagtaa aattgttcaa cttagtgaaa ttagtatgga  12600
caattcacct aatttagcat ggcctcttat tgtaacagct ttaagggcca attctgctgt  12660
caaattacag aataatgagc ttagtcctgt tgcactacga cagatgtctt gtgctgccgg  12720
tactacacaa actgcttgca ctgatgacaa tgcgttagct tactacaaca caacaaaggg  12780
aggtaggttt gtacttgcac tgttatccga tttacaggat ttgaaatggg ctagattccc  12840
taagagtgat ggaactggta ctatctatac agaactggaa ccaccttgta ggtttgttac  12900
agacacacct aaaggtccta aagtgaagta tttatacttt attaaaggat taaacaacct  12960
aaatagaggt atggtacttg gtagtttagc tgccacagta cgtctacaag ctggtaatgc  13020
aacagaagtg cctgccaatt caactgtatt atctttctgt gcttttgctg tagatgctgc  13080
taaagcttac aaagattatc tagctagtgg gggacaacca atcactaatt gtgttaagat  13140
gttgtgtaca cacactggta ctggtcaggc aataacagtt acaccggaag ccaatatgga  13200
tcaagaatcc tttggtggtg catcgtgttg tctgtactgc cgttgccaca tagatcatcc  13260
aaatcctaaa ggattttgtg acttaaaagg taagtatgta caaataccta caacttgtgc  13320
taatgaccct gtgggtttta cacttaaaaa cacagtctgt accgtctgcg gtatgtggaa  13380
aggttatggc tgtagttgtg atcaactccg cgaacccatg cttcagtcag ctgatgcaca  13440
atcgttttta aacgggtttg cggtgtaagt gcagcccgtc ttacaccgtg cggcacaggc  13500
actagtactg atgtcgtata cagggctttt gacatctaca atgataaagt agctggtttt  13560
gctaaattcc taaaaactaa ttgttgtcgc ttccaagaaa aggacgaaga tgacaattta  13620
attgattctt actttgtagt taagagacac actttctcta actaccaaca tgaagaaaca  13680
atttataatt tacttaagga ttgtccagct gttgctaaac atgacttctt taagtttaga  13740
atagacggtg acatggtacc acatatatca cgtcaacgtc ttactaaata cacaatggca  13800
gacctcgtct atgctttaag gcattttgat gaaggtaatt gtgacacatt aaaagaaata  13860
cttgtcacat acaattgttg tgatgatgat tatttcaata aaaaggactg gtatgatttt  13920
gtagaaaacc cagatatatt acgcgtatac gccaacttag gtgaacgtgt acgccaagct  13980
ttgttaaaaa cagtacaatt ctgtgatgcc atgcgaaatg ctggtattgt tggtgtactg  14040
acattagata atcaagatct caatggtaac tggtatgatt tcggtgattt catacaaacc  14100
acgccaggta gtggagttcc tgttgtagat tcttattatt cattgttaat gcctatatta  14160
accttgacca gggctttaac tgcagagtca catgttgaca ctgacttaac aaagccttac  14220
attaagtggg atttgttaaa atatgacttc acggaagaga ggttaaaact ctttgaccgt  14280
tattttaaat attgggatca gacataccac ccaaattgtg ttaactgttt ggatgacaga  14340
tgcattctgc attgtgcaaa ctttaatgtt ttattctcta cagtgttccc acctacaagt  14400
tttggaccac tagtgagaaa aatatttgtt gatggtgttc catttgtagt ttcaactgga  14460
taccacttca gagagctagg tgttgtacat aatcaggatg taaacttaca tagctctaga  14520
cttagtttta aggaattact tgtgtatgct gctgaccctg ctatgcacgc tgcttctggt  14580
aatctattac tagataaacg cactacgtgc ttttcagtag ctgcacttac taacaatgtt  14640
gcttttcaaa ctgtcaaacc cggtaatttt aacaaagact tctatgactt tgctgtgtct  14700
aagggtttct ttaaggaagg aagttctgtt gaattaaaac acttcttctt tgctcaggat  14760
ggtaatgctg ctatcagcga ttatgactac tatcgttata atctaccaac aatgtgtgat  14820
```

```
atcagacaac tactatttgt agttgaagtt gttgataagt actttgattg ttacgatggt  14880
ggctgtatta atgctaacca agtcatcgtc aacaacctag acaaatcagc tggttttcca  14940
tttaataaat ggggtaaggc tagactttat tatgattcaa tgagttatga ggatcaagat  15000
gcacttttcg catatacaaa acgtaatgtc atccctacta taactcaaat gaatcttaag  15060
tatgccatta gtgcaaagaa tagagctcgc accgtagctg gtgtctctat ctgtagtact  15120
atgaccaata gacagtttca tcaaaaatta ttgaaatcaa tagccgccac tagaggagct  15180
actgtagtaa ttggaacaag caaattctat ggtggttggc acaacatgtt aaaaactgtt  15240
tatagtgatg tagaaaaccc tcaccttatg ggttgggatt atcctaaatg tgatagagcc  15300
atgcctaaca tgcttagaat tatggcctca cttgttcttg ctcgcaaaca tacaacgtgt  15360
tgtagcttgt cacaccgttt ctatagatta gctaatgagt gtgctcaagt attgagtgaa  15420
atggtcatgt gtggcggttc actatatgtt aaaccaggtg gaacctcatc aggagatgcc  15480
acaactgctt atgctaatag tgtttttaac atttgtcaag ctgtcacggc caatgttaat  15540
gcacttttat ctactgatgg taacaaaatt gccgataagt atgtccgcaa tttacaacac  15600
agactttatg agtgtctcta tagaaataga gatgttgaca cagactttgt gaatgagttt  15660
tacgcatatt tgcgtaaaca tttctcaatg atgatactct ctgacgatgc tgttgtgtgt  15720
ttcaatagca cttatgcatc tcaaggtcta gtggctagca taaagaactt taagtcagtt  15780
ctttattatc aaaacaatgt ttttatgtct gaagcaaaat gttggactga gactgacctt  15840
actaaaggac ctcatgaatt ttgctctcaa catacaatgc tagttaaaca gggtgatgat  15900
tatgtgtacc ttccttaccc agatccatca agaatcctag gggccggctg ttttgtagat  15960
gatatcgtaa aaacagatgg tacacttatg attgaacggt tcgtgtcttt agctatagat  16020
gcttacccac ttactaaaca tcctaatcag gagtatgctg atgtctttca tttgtactta  16080
caatacataa gaaagctaca tgatgagtta acaggacaca tgttagacat gtattctgtt  16140
atgcttacta atgataacac ttcaaggtat tgggaacctg agttttatga ggctatgtac  16200
acaccgcata cagtcttaca ggctgttggg gcttgtgttc tttgcaattc acagacttca  16260
ttaagatgtg gtgcttgcat acgtagacca ttcttatgtt gtaaatgctg ttacgaccat  16320
gtcatatcaa catcacataa attagtcttg tctgttaatc cgtatgtttg caatgctcca  16380
ggttgtgatg tcacagatgt gactcaactt tacttaggag gtatgagcta ttattgtaaa  16440
tcacataaac cacccattag ttttccattg tgtgctaatg gacaagtttt tggtttatat  16500
aaaaatacat gtgttggtag cgataatgtt actgacttta atgcaattgc aacatgtgac  16560
tggacaaatg ctggtgatta cattttagct aacacctgta ctgaaagact caagcttttt  16620
gcagcagaaa cgctcaaagc tactgaggag acatttaaac tgtcttatgg tattgctact  16680
gtacgtgaag tgctgtctga cagagaatta catctttcat gggaagttgg taaacctaga  16740
ccaccactta accgaaatta tgtctttact ggttatcgtg taactaaaaa cagtaaagta  16800
caaataggag agtacacctt tgaaaaaggt gactatggtg atgctgttgt ttaccgaggt  16860
acaacaactt acaaattaaa tgttggtgat tattttgtgc tgacatcaca tacagtaatg  16920
ccattaagtg cacctacact agtgccacaa gagcactatg ttagaattac tggcttatac  16980
ccaacactca atatctcaga tgagttttct agcaatgttg caaattatca aaaggttggt  17040
atgcaaaagt attctacact ccagggacca cctggtactg gtaagagtca ttttgctatt  17100
ggcctagctc tctactaccc ttctgctcgc atagtgtata cagcttgctc tcatgccgct  17160
```

-continued

```
gttgatgcac tatgtgagaa ggcattaaaa tatttgccta tagataaatg tagtagaatt  17220
atacctgcac gtgctcgtgt agagtgtttt gataaattca aagtgaattc aacattagaa  17280
cagtatgtct tttgtactgt aaatgcattg cctgagacga cagcagatat agttgtcttt  17340
gatgaaattt caatggccac aaattatgat ttgagtgttg tcaatgccag attacgtgct  17400
aagcactatg tgtacattgg cgaccctgct caattacctg caccacgcac attgctaact  17460
aagggcacac tagaaccaga atatttcaat tcagtgtgta gacttatgaa aactataggt  17520
ccagacatgt tcctcggaac ttgtcggcgt tgtcctgctg aaattgttga cactgtgagt  17580
gctttggttt atgataataa gcttaaagca cataaagaca aatcagctca atgctttaaa  17640
atgttttata agggtgttat cacgcatgat gtttcatctg caattaacag gccacaaata  17700
ggcgtggtaa gagaattcct tacacgtaac cctgcttgga gaaaagctgt ctttatttca  17760
ccttataatt cacagaatgc tgtagcctca aagattttgg gactaccaac tcaaactgtt  17820
gattcatcac agggctcaga atatgactat gtcatattca ctcaaaccac tgaaacagct  17880
cactcttgta atgtaaacag atttaatgtt gctattacca gagcaaaagt aggcatactt  17940
tgcataatgt ctgatagaga cctttatgac aagttgcaat ttacaagtct tgaaattcca  18000
cgtaggaatg tggcaacttt acaagctgaa aatgtaacag gactctttaa agattgtagt  18060
aaggtaatca ctgggttaca tcctacacag gcacctacac acctcagtgt tgacactaaa  18120
ttcaaaactg aaggtttatg tgttgacata cctggcatac ctaaggacat gacctataga  18180
agactcatct ctatgatggg ttttaaaatg aattatcaag ttaatggtta ccctaacatg  18240
tttatcaccc gcgaagaagc tataagacat gtacgtgcat ggattggctt cgatgtcgag  18300
gggtgtcatg ctactagaga agctgttggt accaatttac ctttacagct aggtttttct  18360
acaggtgtta acctagttgc tgtacctaca ggttatgttg atacacctaa taatacagat  18420
ttttccagag ttagtgctaa accaccgcct ggagatcaat ttaaacacct cataccactt  18480
atgtacaaag gacttccttg gaatgtagtg cgtataaaga ttgtacaaat gttaagtgac  18540
acacttaaaa atctctctga cagagtcgta tttgtcttat gggcacatgg ctttgagttg  18600
acatctatga agtattttgt gaaaatagga cctgagcgca cctgttgtct atgtgataga  18660
cgtgccacat gcttttccac tgcttcagac acttatgcct gttggcatca ttctattgga  18720
tttgattacg tctataatcc gtttatgatt gatgttcaac aatggggttt tacaggtaac  18780
ctacaaagca accatgatct gtattgtcaa gtccatggta atgcacatgt agctagttgt  18840
gatgcaatca tgactaggtg tctagctgtc cacgagtgct ttgttaagcg tgttgactgg  18900
actattgaat atcctataat tggtgatgaa ctgaagatta atgcggcttg tagaaaggtt  18960
caacacatgg ttgttaaagc tgcattatta gcagacaaat tcccagttct tcacgacatt  19020
ggtaacccta aagctattaa gtgtgtacct caagctgatg tagaatggaa gttctatgat  19080
gcacagcctt gtagtgacaa agcttataaa atagaagaat tattctattc ttatgccaca  19140
cattctgaca aattcacaga tggtgtatgc ctattttgga attgcaatgt cgatagatat  19200
cctgctaatt ccattgtttg tagatttgac actagagtgc tatctaacct taacttgcct  19260
ggttgtgatg gtggcagttt gtatgtaaat aaacatgcat tccacacacc agcttttgat  19320
aaaagtgctt ttgttaattt aaaacaatta ccattttttct attactctga cagtccatgt  19380
gagtctcatg gaaaacaagt agtgtcagat atagattatg taccactaaa gtctgctacg  19440
tgtataacac gttgcaattt aggtggtgct gtctgtagac atcatgctaa tgagtacaga  19500
ttgtatctcg atgcttataa catgatgatc tcagctggct ttagcttgtg ggtttacaaa  19560
```

caatttgata cttataacct ctggaacact tttacaagac ttcagagttt agaaaatgtg 19620
gcttttaatg ttgtaaataa gggacacttt gatggacaac agggtgaagt accagtttct 19680
atcattaata acactgttta cacaaaagtt gatggtgttg atgtagaatt gtttgaaaat 19740
aaaacaacat tacctgttaa tgtagcattt gagctttggg ctaagcgcaa cattaaacca 19800
gtaccagagg tgaaaatact caataatttg ggtgtggaca ttgctgctaa tactgtgatc 19860
tgggactaca aaagagatgc tccagcacat atatctacta ttggtgtttg ttctatgact 19920
gacatagcca agaaaccaac tgaaacgatt tgtgcaccac tcactgtctt ttttgatggt 19980
agagttgatg gtcaagtaga cttatttaga aatgcccgta atggtgttct tattacagaa 20040
ggtagtgtta aaggtttaca accatctgta ggtcccaaac aagctagtct taatggagtc 20100
acattaattg gagaagccgt aaaaacacag ttcaattatt ataagaaagt tgatggtgtt 20160
gtccaacaat tacctgaaac ttactttact cagagtagaa atttacaaga atttaaaccc 20220
aggagtcaaa tggaaattga tttcttagaa ttagctatgg atgaattcat tgaacggtat 20280
aaattagaag gctatgcctt cgaacatatc gtttatggag attttagtca tagtcagtta 20340
ggtggtttac atctactgat tggactagct aaacgtttta aggaatcacc ttttgaatta 20400
gaagatttta ttcctatgga cagtacagtt aaaaactatt tcataacaga tgcgcaaaca 20460
ggttcatcta agtgtgtgtg ttctgttatt gatttattac ttgatgattt tgttgaaata 20520
ataaaatccc aagatttatc tgtagtttct aaggttgtca aagtgactat tgactataca 20580
gaaatttcat ttatgctttg gtgtaaagat ggccatgtag aaacatttta cccaaaatta 20640
caatctagtc aagcgtggca accgggtgtt gctatgccta atctttacaa aatgcaaaga 20700
atgctattag aaaagtgtga ccttcaaaat tatggtgata gtgcaacatt acctaaaggc 20760
ataatgatga atgtcgcaaa atatactcaa ctgtgtcaat atttaaacac attaacatta 20820
gctgtaccct ataatatgag agttatacat tttggtgctg gttctgataa aggagttgca 20880
ccaggtacag ctgttttaag acagtggttg cctacgggta cgctgcttgt cgattcagat 20940
cttaatgact ttgtctctga tgcagattca actttgattg gtgattgtgc aactgtacat 21000
acagctaata aatgggatct cattattagt gatatgtacg accctaagac taaaaatgtt 21060
acaaaagaaa atgactctaa agagggtttt ttcacttaca tttgtgggtt tatacaacaa 21120
aagctagctc ttggaggttc cgtggctata aagataacag aacattcttg gaatgctgat 21180
ctttataagc tcatgggaca cttcgcatgg tggacagcct ttgttactaa tgtgaatgcg 21240
tcatcatctg aagcattttt aattggatgt aattatcttg gcaaaccacg cgaacaaata 21300
gatggttatg tcatgcatgc aaattacata ttttggagga atacaaatcc aattcagttg 21360
tcttcctatt ctttatttga catgagtaaa tttcccctta aattaagggg tactgctgtt 21420
atgtctttaa aagaaggtca aatcaatgat atgattttat ctcttcttag taaaggtaga 21480
cttataatta gagaaaacaa cagagttgtt atttctagtg atgttcttgt taacaactaa 21540
acgaacaatg tttgtttttc ttgttttatt gccactagtc tctagtcagt gtgttaatct 21600
tacaaccaga actcaattac cccctgcata cactaattct ttcacacgtg gtgtttatta 21660
ccctgacaaa gttttcagat cctcagtttt acattcaact caggacttgt tcttaccttt 21720
cttttccaat gttacttggt tccatgctat acatgtctct gggaccaatg gtactaagag 21780
gtttgataac cctgtcctac catttaatga tggtgtttat tttgcttcca ctgagaagtc 21840
taacataata agaggctgga tttttggtac tactttagat tcgaagaccc agtccctact 21900

-continued

```
tattgttaat aacgctacta atgttgttat taaagtctgt gaatttcaat tttgtaatga  21960
tccatttttg ggtgtttatt accacaaaaa caacaaaagt tggatggaaa gtgagttcag  22020
agtttattct agtgcgaata attgcacttt tgaatatgtc tctcagcctt ttcttatgga  22080
ccttgaagga aaacagggta atttcaaaaa tcttagggaa tttgtgttta agaatattga  22140
tggttatttt aaaatatatt ctaagcacac gcctattaat ttagtgcgtg atctccctca  22200
gggtttttcg gctttagaac cattggtaga tttgccaata ggtattaaca tcactaggtt  22260
tcaaacttta cttgctttac atagaagtta tttgactcct ggtgattctt cttcaggttg  22320
gacagctggt gctgcagctt attatgtggg ttatcttcaa cctaggactt ttctattaaa  22380
atataatgaa aatggaacca ttacagatgc tgtagactgt gcacttgacc ctctctcaga  22440
aacaaagtgt acgttgaaat ccttcactgt agaaaaagga atctatcaaa cttctaactt  22500
tagagtccaa ccaacagaat ctattgttag atttcctaat attacaaact tgtgcccttt  22560
tggtgaagtt tttaacgcca ccagatttgc atctgtttat gcttggaaca ggaagagaat  22620
cagcaactgt gttgctgatt attctgtcct atataattcc gcatcatttt ccacttttaa  22680
gtgttatgga gtgtctccta ctaaattaaa tgatctctgc tttactaatg tctatgcaga  22740
ttcatttgta attagaggtg atgaagtcag acaaatcgct ccagggcaaa ctggaaagat  22800
tgctgattat aattataaat taccagatga ttttacaggc tgcgttatag cttggaattc  22860
taacaatctt gattctaagg ttggtggtaa ttataattac ctgtatagat tgtttaggaa  22920
gtctaatctc aaacctttg agagagatat ttcaactgaa atctatcagg ccggtagcac  22980
accttgtaat ggtgttgaag gttttaattg ttactttcct ttacaatcat atggtttcca  23040
acccactaat ggtgttggtt accaaccata cagagtagta gtactttctt ttgaacttct  23100
acatgcacca gcaactgttt gtggacctaa aaagtctact aatttggtta aaaacaaatg  23160
tgtcaatttc aacttcaatg gtttaacagg cacaggtgtt cttactgagt ctaacaaaaa  23220
gtttctgcct ttccaacaat ttggcagaga cattgctgac actactgatg ctgtccgtga  23280
tccacagaca cttgagattc ttgacattac accatgttct tttggtggtg tcagtgttat  23340
aacaccagga acaaatactt ctaaccaggt tgctgttctt tatcaggatg ttaactgcac  23400
agaagtccct gttgctattc atgcagatca acttactcct acttggcgtg tttattctac  23460
aggttctaat gtttttcaaa cacgtgcagg ctgtttaata ggggctgaac atgtcaacaa  23520
ctcatatgag tgtgacatac ccattggtgc aggtatatgc gctagttatc agactcagac  23580
taattctcct cggcgggcac gtagtgtagc tagtcaatcc atcattgcct acactatgtc  23640
acttggtgca gaaaattcag ttgcttactc taataactct attgccatac ccacaaattt  23700
tactattagt gttaccacag aaattctacc agtgtctatg accaagacat cagtagattg  23760
tacaatgtac atttgtggtg attcaactga atgcagcaat cttttgttgc aatatggcag  23820
tttttgtaca caattaaacc gtgctttaac tggaatagct gttgaacaag acaaaaacac  23880
ccaagaagtt tttgcacaag tcaaacaaat ttacaaaaca ccaccaatta aagattttgg  23940
tggttttaat ttttcacaaa tattaccaga tccatcaaaa ccaagcaaga ggtcatttat  24000
tgaagatcta cttttcaata aagtgacact tgcagatgct ggcttcatca aacaatatgg  24060
tgattgcctt ggtgatattg ctgctagaga cctcatttgt gcacaaaagt ttaacggcct  24120
tactgttttg ccacctttgc tcacagatga aatgattgct caatacactt ctgcactgtt  24180
agcgggtaca atcacttctg gttggacctt tggtgcaggt gctgcattac aaataccatt  24240
tgctatgcaa atggcttata ggtttaatgg tattggagtt acacagaatg ttctctatga  24300
```

```
gaaccaaaaa ttgattgcca accaatttaa tagtgctatt ggcaaaattc aagactcact  24360
ttcttccaca gcaagtgcac ttggaaaact tcaagatgtg gtcaaccaaa atgcacaagc  24420
tttaaacacg cttgttaaac aacttagctc caattttggt gcaatttcaa gtgttttaaa  24480
tgatatcctt tcacgtcttg acaaagttga ggctgaagtg caaattgata ggttgatcac  24540
aggcagactt caaagtttgc agacatatgt gactcaacaa ttaattagag ctgcagaaat  24600
cagagcttct gctaatcttg ctgctactaa aatgtcagag tgtgtacttg gacaatcaaa  24660
aagagttgat ttttgtggaa agggctatca tcttatgtcc ttccctcagt cagcacctca  24720
tggtgtagtc ttcttgcatg tgacttatgt ccctgcacaa gaaaagaact tcacaactgc  24780
tcctgccatt tgtcatgatg gaaaagcaca ctttcctcgt gaaggtgtct ttgtttcaaa  24840
tggcacacac tggtttgtaa cacaaaggaa tttttatgaa ccacaaatca ttactacaga  24900
caacacattt gtgtctggta actgtgatgt tgtaatagga attgtcaaca acacagttta  24960
tgatcctttg caacctgaat tagactcatt caaggaggag ttagataaat attttaagaa  25020
tcatacatca ccagatgttg atttaggtga catctctggc attaatgctt cagttgtaaa  25080
cattcaaaaa gaaattgacc gcctcaatga ggttgccaag aatttaaatg aatctctcat  25140
cgatctccaa gaacttggaa agtatgagca gtatataaaa tggccatggt acatttggct  25200
aggttttata gctggcttga ttgccatagt aatggtgaca attatgcttt gctgtatgac  25260
cagttgctgt agttgtctca agggctgttg ttcttgtgga tcctgctgca aatttgatga  25320
agacgactct gagccagtgc tcaaaggagt caaattacat tacacataaa cgaacttatg  25380
gatttgttta tgagaatctt cacaattgga actgtaactt tgaagcaagg tgaaatcaag  25440
gatgctactc cttcagattt tgttcgcgct actgcaacga taccgataca agcctcactc  25500
cctttcggat ggcttattgt tggcgttgca cttcttgctg tttttcagag cgcttccaaa  25560
atcataaccc tcaaaaagag atggcaacta gcactctcca agggtgttca ctttgtttgc  25620
aacttgctgt tgttgtttgt aacagtttac tcacaccttt tgctcgttgc tgctggcctt  25680
gaagcccctt ttctctatct ttatgcttta gtctacttct tgcagagtat aaactttgta  25740
agaataataa tgaggctttg gctttgctgg aaatgccgtt ccaaaaaccc attactttat  25800
gatgccaact attttctttg ctggcatact aattgttacg actattgtat accttacaat  25860
agtgtaactt cttcaattgt cattacttca ggtgatggca caacaagtcc tatttctgaa  25920
catgactacc agattggtgg ttatactgaa aaatgggaat ctggagtaaa agactgtgtt  25980
gtattacaca gttacttcac ttcagactat taccagctgt actcaactca attgagtaca  26040
gacactggtg ttgaacatgt taccttcttc atctacaata aaattgttga tgagcctgaa  26100
gaacatgtcc aaattcacac aatcgacggt tcatccggag ttgttaatcc agtaatggaa  26160
ccaatttatg atgaaccgac gacgactact agcgtgcctt tgtaagcaca agctgatgag  26220
tacgaactta tgtactcatt cgtttcggaa gagacaggta cgttaatagt taatagcgta  26280
cttctttttc ttgctttcgt ggtattcttg ctagttacac tagccatcct tactgcgctt  26340
cgattgtgtg cgtactgctg caatattgtt aacgtgagtc ttgtaaaacc ttctttttac  26400
gtttactctc gtgttaaaaa tctgaattct tctagagttc ctgatcttct ggtctaaacg  26460
aactaaatat tatattagtt tttctgtttg gaactttaat tttagccatg gcagattcca  26520
acggtactat taccgttgaa gagcttaaaa agctccttga acaatggaac ctagtaatag  26580
gtttcctatt ccttacatgg atttgtcttc tacaatttgc ctatgccaac aggaataggt  26640
```

-continued

```
ttttgtatat aattaagtta attttcctct ggctgttatg gccagtaact ttagcttgtt  26700
ttgtgcttgc tgctgtttac agaataaatt ggatcaccgg tggaattgct atcgcaatgg  26760
cttgtcttgt aggcttgatg tggctcagct acttcattgc ttctttcaga ctgtttgcgc  26820
gtacgcgttc catgtggtca ttcaatccag aaactaacat tcttctcaac gtgccactcc  26880
atggcactat tctgaccaga ccgcttctag aaagtgaact cgtaatcgga gctgtgatcc  26940
ttcgtggaca tcttcgtatt gctggacacc atctaggacg ctgtgacatc aaggacctgc  27000
ctaaagaaat cactgttgct acatcacgaa cgctttctta ttacaaattg ggagcttcgc  27060
agcgtgtagc aggtgactca ggttttgctg catacagtcg ctacaggatt ggcaactata  27120
aattaaacac agaccattcc agtagcagtg acaatattgc tttgcttgta cagtaagtga  27180
caacagatgt ttcatctcgt tgactttcag gttactatag cagagatatt actaattatt  27240
atgaggactt ttaaagtttc catttggaat cttgattaca tcataaacct cataattaaa  27300
aatttatcta agtcactaac tgagaataaa tattctcaat tagatgaaga gcaaccaatg  27360
gagattgatt aaacgaacat gaaaattatt cttttcttgg cactgataac actcgctact  27420
tgtgagcttt atcactacca agagtgtgtt agaggtacaa cagtactttt aaaagaacct  27480
tgctcttctg gaacatacga gggcaattca ccatttcatc ctctagctga taacaaattt  27540
gcactgactt gctttagcac tcaatttgct tttgcttgtc ctgacggcgt aaaacacgtc  27600
tatcagttac gtgccagatc agtttcacct aaactgttca tcagacaaga ggaagttcaa  27660
gaactttact ctccaatttt tcttattgtt gcggcaatag tgtttataac actttgcttc  27720
acactcaaaa gaaagacaga atgattgaac tttcattaat tgacttctat ttgtgctttt  27780
tagcctttct gctattcctt gttttaatta tgcttattat cttttggttc tcacttgaac  27840
tgcaagatca taatgaaact tgtcacgcct aaacgaacat gaaatttctt gttttcttag  27900
gaatcatcac aactgtagct gcatttcacc aagaatgtag tttacagtca tgtactcaac  27960
atcaaccata tgtagttgat gacccgtgtc ctattcactt ctattctaaa tggtatatta  28020
gagtaggagc tagaaaatca gcacctttaa ttgaattgtg cgtggatgag gctggttcta  28080
aatcacccat tcagtacatc gatatcggta attatacagt ttcctgttta cctttacaa  28140
ttaattgcca ggaacctaaa ttgggtagtc ttgtagtgcg ttgttcgttc tatgaagact  28200
ttttagagta tcatgacgtt cgtgttgttt tagatttcat ctaaacgaac aaactaaaat  28260
gtctgataat ggaccccaaa atcagcgaaa tgcaccccgc attacgtttg gtggaccctc  28320
agattcaact ggcagtaacc agaatggaga acgcagtggg gcgcgatcaa aacaacgtcg  28380
gccccaaggt ttacccaata atactgcgtc ttggttcacc gctctcactc aacatggcaa  28440
ggaagacctt aaattccctc gaggacaagg cgttccaatt aacaccaata gcagtccaga  28500
tgaccaaatt ggctactacc gaagagctac cagacgaatt cgtggtggtg acggtaaaat  28560
gaaagatctc agtccaagat ggtatttcta ctacctagga actgggccag aagctggact  28620
tccctatggt gctaacaaag acggcatcat atgggttgca actgagggag ccttgaatac  28680
accaaaagat cacattggca cccgcaatcc tgctaacaat gctgcaatcg tgctacaact  28740
tcctcaagga acaacattgc caaaaggctt ctacgcagaa gggagcagag gcggcagtca  28800
agcctcttct cgttcctcat cacgtagtcg caacagttca agaaattcaa ctccaggcag  28860
cagtagggga acttctcctg ctagaatggc tggcaatggc ggtgatgctg ctcttgcttt  28920
gctgctgctt gacagattga accagcttga gagcaaaatg tctggtaaag gccaacaaca  28980
acaaggccaa actgtcacta agaaatctgc tgctgaggct tctaagaagc ctcggcaaaa  29040
```

-continued

```
acgtactgcc actaaagcat acaatgtaac acaagctttc ggcagacgtg gtccagaaca  29100
aacccaagga aattttgggg accaggaact aatcagacaa ggaactgatt acaaacattg  29160
gccgcaaatt gcacaatttg cccccagcgc ttcagcgttc ttcggaatgt cgcgcattgg  29220
catggaagtc acaccttcgg gaacgtggtt gacctacaca ggtgccatca aattggatga  29280
caaagatcca aatttcaaag atcaagtcat tttgctgaat aagcatattg acgcatacaa  29340
aacattccca ccaacagagc ctaaaaagga caaaaagaag aaggctgatg aaactcaagc  29400
cttaccgcag agacagaaga aacagcaaac tgtgactctt cttcctgctg cagatttgga  29460
tgatttctcc aaacaattgc aacaatccat gagcagtgct gactcaactc aggcctaaac  29520
tcatgcagac cacacaaggc agatgggcta tataaacgtt ttcgcttttc cgtttacgat  29580
atatagtcta ctcttgtgca gaatgaattc tcgtaactac atagcacaag tagatgtagt  29640
taactttaat ctcacatagc aatctttaat cagtgtgtaa cattagggag gacttgaaag  29700
agccaccaca ttttcaccga ggccacgcgg agtacgatcg agtgtacagt gaacaatgct  29760
agggagagct gcctatatgg aagagcccta atgtgtaaaa ttaattttag t           29811
```

RAPID ASSAY FOR DETECTION OF SARS-COV-2 ANTIBODIES

CROSS REFERENCE TO RELATED APPLICATIONS

This application is a divisional of U.S. patent application Ser. No. 17/140,321, filed on Jan. 4, 2021, which is incorporated by reference herein in its entirety.

REFERENCE TO SEQUENCE LISTING

This application is filed with a Computer Readable Form of a Sequence Listing in accordance with 37 C.F.R. § 1.821(c). The text file submitted by EFS, "026389-9305-US02_sequence_listing_10-SEP-2021_ST25.K" was created on Sep. 10, 2021, contains 67 sequences, has a file size of 199 Kbytes, and is hereby incorporated by reference in its entirety.

TECHNICAL FIELD

Described herein are diagnostic and control fusion protein reagents and methods for use thereof in simple rapid and inexpensive hemagglutinin assays for the detection of subject antibodies directed to the SARS-CoV-2 virus.

BACKGROUND

The COVID19 pandemic caused by SARS-CoV-2 approaches its first anniversary with close to one million deaths worldwide. At this point, countermeasures are largely restricted to symptomatic therapeutic interventions and prophylactic social distancing. Without a clear timeline for the availability of better therapeutic options and just starting vaccination efforts, it is clear that proper pandemic management hinges on the availability of diagnostic tests, including those revealing the presence of the virus itself to identify infectious carriers as well as those detecting antibody responses to assess the kinetics of the pandemic and the susceptibility of individual patients and the population at large. The latter aspect will also be relevant for evaluation and guidance of large-scale vaccination efforts.

Proper management of the pandemic caused by SARS-CoV-2 (COVID19) depends on laboratory tests that reliably detect (i) active virus, to identify virus carriers and (ii) SARS-CoV-2-specific antibodies, to identify individuals who were previously exposed to SARS-CoV-2, are at risk for infection or have successfully been vaccinated.

As investigated in detail in a comparative meta-analysis study, a significant (and growing) number of antibody tests are currently available, including various ELISAs (enzyme-linked immunosorbent assay) and related technologies, such as ECLIA (electrochemiluminescence immunoassay), FMIA (fluorescent microsphere Immunoassay), CMIA (chemiluminescent microparticle immunoassay) and ELFA (enzyme-linked fluorescence assay) [1]. Most of these tests exhibit appropriate specificity and sensitivity and are suitable for high throughput format in diagnostic laboratories [1]. Disadvantages include their restriction to special equipment and professional laboratories, relatively high costs and long turn-around times from sample acquisition to results. An alternative technology is the lateral flow immuno-assay (LVIA), which in principle can be conducted with minimal laboratory equipment. However, as also analyzed directly in referenced study, LFIAs typically exhibit appropriate specificity but restricted sensitivity, usually below 80%, and are relatively expensive (~$18 per test) [1].

While small, short-term studies indicated that antibody responses in asymptomatic patients may wean after weeks, at least two large scale studies have now demonstrated that antibody levels in symptomatic patients against the Spike protein and the Nucleocapsid (N) protein (NP) remain sustained at relatively high levels for at least 4-6 months [2]. These studies suggest that assessment of SARS-CoV-2-specific antibodies represents a proper tool for epidemiological studies and, likely, at least intermediate-term protection of convalescent patients. While studies so far are based on tests using the Spike or Nucleocapsid proteins as antigens, a recent study using luciferase-immunoprecipitation highlighted additional immunogenic proteins of SARS-CoV-2, in particular a small protein encoded by the open reading frame (ORF) 8 (ORF8), a known pathogenicity factor [3].

What is needed are simple, rapid, and inexpensive field tests for the detection of SARS-CoV-2-specific antibodies.

SUMMARY

One embodiment described herein is a nucleotide sequence encoding a polypeptide, wherein the polypeptide comprises a human red blood cell binding antibody domain (RBD) and a SARS CoV-2 virus protein domain (CVD). In one aspect, the RBD comprises a glycophorin A-binding nanobody comprising 90-99% identity to SEQ ID NO: 22. In another aspect, the CVD comprises one or more of a spike protein, a nucleocapsid protein, ORF8 protein, ORF3b protein, or envelope protein comprising 90-99% identity to all or a portion of SEQ ID NO: 24, 26, 28, or 30. In another aspect, the polypeptide has the structure: SS-GAP-RBD-GL2-CVD-GL3-AFT or SS-GL1-RBD-GL2-CVD-GL3-CVD-GL4-AFT; wherein: SS is a secretion signal domain; RBD is a glycophorin A-binding nanobody domain; GAP, GL1, GL2, GL3, and GL4 are linker domains; CVD is a SARS CoV-2 virus polypeptide domain comprising a spike protein, nucleocapsid protein, ORF8 protein, ORF3b protein, or envelope protein domains; and AFT is an affinity purification tag sequence. In another aspect, the SS comprises 90-99% identity to SEQ ID NO: 20. In another aspect, the GAP, GL1, GL2, GL3, or GL4 comprises 90-99% identity to one or more of SEQ ID NO: 38, 40, 42, 44, or 46. In another aspect, the AFT comprises 90-99% identity to one or more of SEQ ID NO: 58, 60, 62, or 64. In another aspect, the nucleotide sequence has 90% to 99% identity to SEQ ID NO: 1, 3, 5, 7, 9, or 11. In another aspect, the nucleotide sequence is one of SEQ ID NO: 1, 3, 5, 7, 9, or 11.

Another embodiment described herein is a polynucleotide vector comprising a nucleotide sequence described herein.

Another embodiment described herein is a cell comprising a polynucleotide vector comprising a nucleotide sequence described herein.

Another embodiment described herein is a polypeptide encoded by a nucleotide sequence described herein.

Another embodiment described herein is a polypeptide encoded by a nucleotide sequence described herein, wherein the polypeptide has 90% to 99% identity to SEQ ID NO: 2, 4, 6, 8, 10, or 12.

Another embodiment described herein is a polypeptide encoded by a nucleotide sequence described herein, wherein the polypeptide is SEQ ID NO: 2, 4, 6, 8, 10, or 12.

Another embodiment described herein is a diagnostic reagent or research tool comprising a polypeptide encoded by the nucleotide sequence described herein.

Another embodiment described herein is a method or means for manufacturing a nucleotide sequence as described herein or a polypeptide encoded by the nucleotide sequence, the process comprising: transforming or transfecting a cell with a nucleic acid comprising the nucleotide sequence; growing the cells; optionally, harvesting the cells and isolating quantities of the nucleotide sequence; inducing expression of a polypeptide encoded by the nucleotide sequence; harvesting the cells; and isolating and purifying the polypeptide.

Another embodiment described herein is a nucleotide sequence or a polypeptide encoded by the nucleotide sequence, each produced by a method or means described herein.

Another embodiment described herein is a nucleotide sequence encoding a diagnostic control polypeptide, wherein the polypeptide comprises: (a) a glycophorin A-binding nanobody domain comprising 90-99% identity to SEQ ID NO: 22; (b) one or more anti-SARS Co-V-2 nanobody domains comprising 90-99% identity to SEQ ID NO: 32 and one or more multimerization domains comprising 90-99% identity to SEQ ID NO: 34 or 36. In one aspect, the polypeptides have the structure: SS-GAP-RBD-GL5-AFT; SS-GAP-anti-CVD-GL6-anti-CVD-GL7-IgGFC-GL8-AFT; or SS-GAP-anti-CVD-GL6-anti-CVD-SGT-HIZD-GL8-AFT; wherein: SS is a secretion signal domain; RBD is a glycophorin A-binding nanobody domain; GAP, GL5, GL6, GL7, GL8, and SGT are linker domains; Anti-CVD is an anti-SARS CoV-2 surface glycoprotein receptor binding domain nanobody domain; IgGFC is a human immunoglobulin FC dimerization domain; HIZD is a Hinge-isoleucine zipper trimerization domain; and AFT is an affinity purification tag sequence. In another aspect, the SS comprises 90-99% identity to SEQ ID NO: 20. In another aspect, the GAP, SGT, GL5, GL6, GL7, or GL8 comprises 90-99% identity to one or more of SEQ ID NO: 38, 48, 50, 52, 54, or 56. In another aspect, the AFT comprises 90-99% identity to one or more of SEQ ID NO: 58, 60, 62, or 64. In another aspect, the nucleotide sequence has 90% to 99% identity to SEQ ID NO: 13, 15, or 17. In another aspect, the nucleotide sequence is one of SEQ ID NO: 13, 15, or 17.

Another embodiment described herein is a polynucleotide vector comprising a nucleotide sequence encoding a diagnostic control polypeptide as described herein.

Another embodiment described herein is a cell comprising a polynucleotide vector comprising a nucleotide sequence encoding a diagnostic control polypeptide as described herein.

Another embodiment described herein is a diagnostic control polypeptide as described herein.

Another embodiment described herein is a diagnostic control polypeptide having 90% to 99% identity to SEQ ID NO: 14, 16, or 18.

Another embodiment described herein is a diagnostic control polypeptide having the polypeptide sequence of SEQ ID NO: 14, 16, or 18.

Another embodiment described herein is a diagnostic reagent or research tool comprising a polypeptide encoded by a nucleotide sequence described herein.

Another embodiment described herein is a diagnostic or control polypeptide comprising the amino acid sequence of SEQ ID NO: 2, 4, 6, 8, 10, 12, 14, 16, or 18.

Another embodiment described herein is a method for evaluating whether a subject is infected or has been infected with SARS-CoV-2, the method comprising: (a) providing a sample of a biological fluid from a subject in need of diagnosis; (b) combining the biological fluid with a diagnostic polypeptide comprising 90 to 99% identity to the amino acid sequence of SEQ ID NO: 2, 4, 6, 8, 10, 12 to form a subject sample; (c) optionally, combining a negative control reagent or a positive control polypeptide comprising 90 to 95% identity to the amino acid sequence of SEQ ID NO: 14 (negative control) or SEQ ID NO: 16 or 18 (positive controls), with the biological fluid and a diagnostic polypeptide comprising 90 to 99% identity to the amino acid sequence of SEQ ID NO: 2, 10, or 12 to form one or more control samples; (d) permitting the subject sample and control samples to incubate for a period of time; (e) evaluating the results by visualization, imaging, optical density, impedance, or microscopy; and (f) optionally, comparing the subject sample and control samples to validate the subject sample results; wherein the presence of hemagglutination in the subject sample is a positive diagnostic indication of SARS-CoV-2 infection, and the absence of hemagglutination in the subject sample is a negative diagnostic indication of SARS-CoV-2 infection. In one aspect, the biological fluid is whole blood, plasma, or serum. In another aspect, when the biological fluid is plasma or serum, washed human red blood cells of blood group 0 are combined with the subject sample and the diagnostic or control polypeptides in steps (b) or (c). In another aspect, wherein the diagnostic or control polypeptides have a concentration of about 10 μg/mL to about 100 μg/mL. In another aspect, the subject sample and/or control samples in steps (b) and/or (c) are dispensed on a test card, glass slide, microtiter plate, or other substrate prior to step (d). In another aspect, when the subject sample has a positive diagnostic indication of SARS-CoV-2 infection, the method further comprises: (g) administering one or more therapeutics or treatments to the subject.

Another embodiment described herein is a kit comprising: (a) one or more diagnostic or control polypeptides comprising the amino acid sequence of SEQ ID NO: 2, 4, 6, 8, 10, 12, 14, 16, or 18; (b) a test substrate; and (c) optionally, a label or instructions for use. In one aspect, the kit further comprises one or more of alcohol saturated towelettes; finger prick lances, capillaries, or gloves.

Another embodiment described herein is the use of a polypeptide comprising 90 to 99% identity to the amino acid sequence of SEQ ID NO: 2, 4, 6, 8, 10, 12, 14, 16, or 18 for the diagnosis of SARS-CoV-2 in a subject in need of diagnosis thereof.

DETAILED DESCRIPTION

Figure 1:
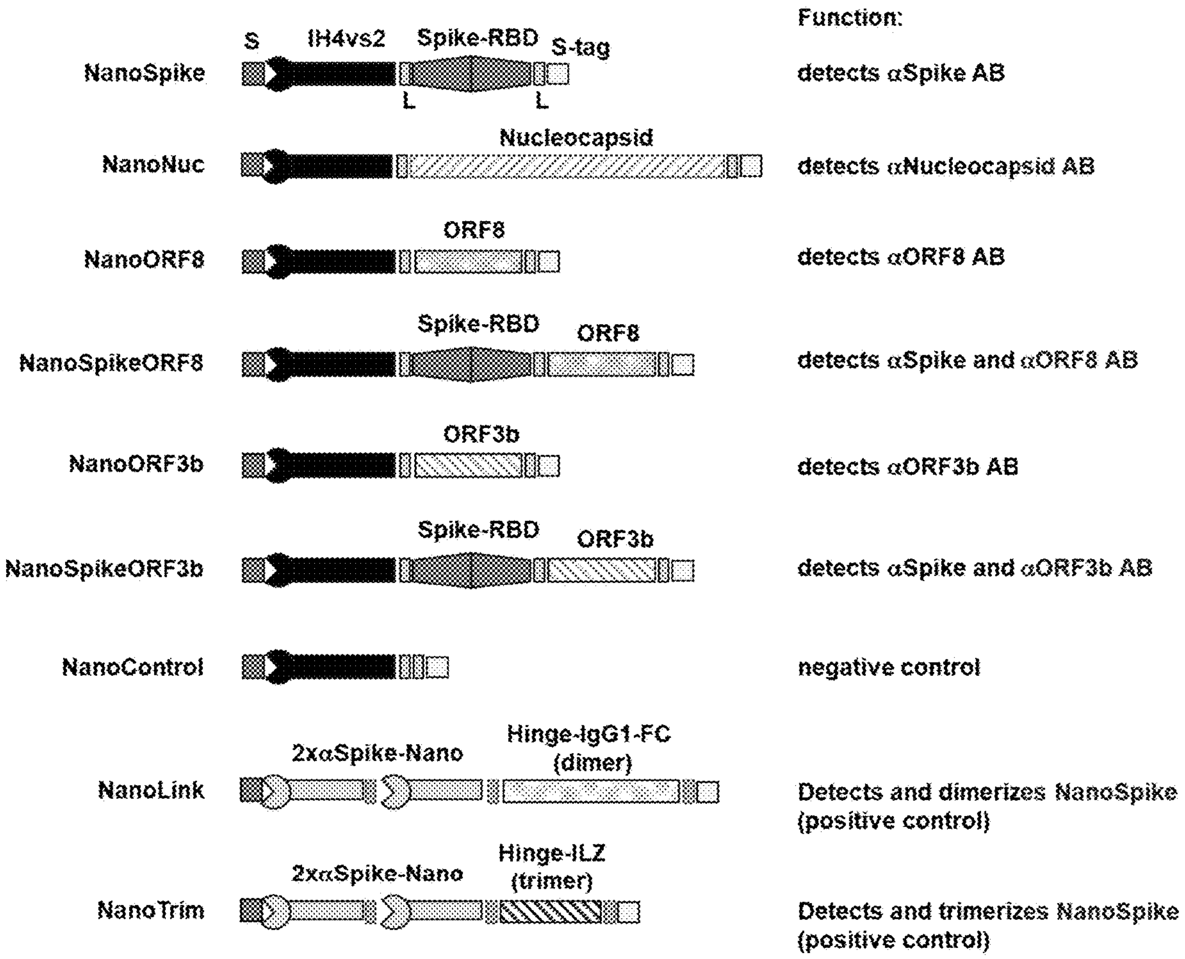
FIG. 1 shows schematic representations of the diagnostic and control fusion protein constructs. Key: S, secretion signal (IFNβ); IH4vs2, GPA-specific nanobody IH4vs2, which is efficiently secreted from mammalian cells (as opposed to the original IH4 nanobody); L, flexible linker; Spike, Spike-RBD of SARS-CoV-2; S-tag, Tandem-Strep-tag mediating binding to StrepTactin® matrix (IBA) for affinity purification; Nucleocapsid, Nucleocapsid protein of SARS-CoV-2, ORF8, ORF8 of SARS-CoV-2, ORF3b, ORF3b of SARS-CoV-2; 2×αSpike-Nano, tandem-fusion construct of two Spike-RBD-binding H11-D4 nanobodies, separated by flexible linker; Hinge-IgG1-FC, dimerizing Hinge-FC moiety of IgG1; Hinge-ILZ, trimerizing hinge-isoleucin-zipper domain. Polypeptide sequences are shown in Table 1.
Figure 2:
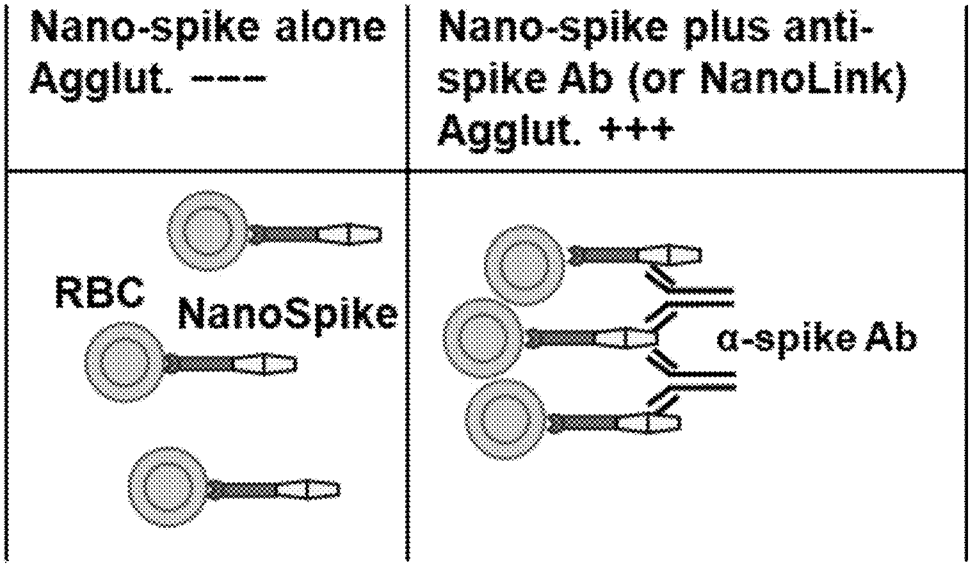
FIG. 2 shows the principle of Nano-spike-mediated hemagglutination in the presence of virus-specific (e.g., Spike-specific) antibodies (or the positive control nanobody, such as NanoLink).

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Preferred methods and materials are described below, although methods and materials similar or equivalent to those described herein can be used in practice or testing of the present invention.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a human. In another embodiment, the subject is a human suspected of being infected with SARS-CoV-2 or that is infected with SARS-CoV-2.

As used herein, a subject is "in need of treatment" if such subject would benefit biologically, medically, or in quality of life from such treatment. A subject in need of treatment does not necessarily present symptoms, particular in the case of preventative or prophylaxis treatments. In one aspect, the subject may need diagnosis of a condition prior to treatment. Embodiments described herein can be used to make or confirm such a diagnosis.

As used herein a subject is “in need of diagnosis” if such subject would benefit biologically, medically, or in quality of life from such diagnosis. In one embodiment a subject needs diagnosis of SARS-CoV-2. In one aspect the subject may be presenting symptoms of SARS-CoV-2, may have been exposed to another individual presenting symptoms of SARS-CoV-2, may be a “carrier” of SARS-CoV-2 (without clinical presentation or symptoms), or may have previously been infected with SARS-CoV-2 and is in need of confirmation of such infection.

As used herein, the terms “inhibit,” “inhibition,” or “inhibiting” refer to the reduction or suppression of a given biological process, condition, symptom, disorder, or disease, or a significant decrease in the baseline activity of a biological activity or process.

As used herein, “treatment” or “treating” refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term “treatment” also refers to reducing the severity of a disease or symptoms associated with such disease prior to affliction with the disease. “Repressing” or “ameliorating” a disease, disorder, or the symptoms thereof involves administering a cell, composition, or compound described herein to a subject after clinical appearance of such disease, disorder, or its symptoms. “Prophylaxis of” or “preventing” a disease, disorder, or the symptoms thereof involves administering a cell, composition, or compound described herein to a subject prior to onset of the disease, disorder, or the symptoms thereof. “Suppressing” a disease or disorder involves administering a cell, composition, or compound described herein to a subject after induction of the disease or disorder thereof but before its clinical appearance or symptoms thereof have manifest. In one embodiment, after diagnosis of a subject being infected with SARS-CoV-2, a variety of treatments may be administered to target the virus, ameliorate symptoms, or provide palliative care.

Coronaviruses (CoVs), are enveloped positive-sense RNA viruses, which are surrounded by crown-shaped, club-like spikes projection on the outer surface. Coronaviruses' spike proteins are glycoproteins that are embedded over the viral envelope. This spike protein attaches to specific cellular receptors and initiates structural changes of spike protein, and causes penetration of cell membranes, which results in the release of the viral nucleocapsid into the cell. These spike proteins determine host trophism. Coronaviruses have a large RNA genome, ranging in size from 26 to 32 kilobases and capable of obtaining distinct ways of replication. Like other RNA viruses, coronaviruses under-go replication of the genome and transcription of mRNAs upon infection. Coronavirus infection in a subject can result in significant and long-term damage of the lungs, leading to possibly sever respiratory issues.

As used herein “SARS-CoV-2” is a beta-coronavirus (Beta-CoV or β-CoV). In particular, SARS-CoV-2 is a Beta-CoV of lineage B. SARS-CoV-2 may also be known as “2019-nCoV” or 2019 novel coronavirus. The disease associated with SARS-CoV-2 is known as COVID-19. Beta-coronaviruses are one of four genera of coronaviruses and are enveloped, positive-sense, single-stranded RNA viruses of zoonotic origin. Beta-coronaviruses mainly infect bats, but they also infect other species like humans, camels, and rabbits. SARS-CoV-2 may be transferable between animals, such as between humans. As used herein “viral transmission” is the process by which viruses spread between host subjects. Transmission occurs from person to person by direct or indirect contact or exposure. Examples of direct contact include, but are not limited to, the exchange of body fluids between a subject infected with the virus and someone else. Indirect contact includes, but is not limited to, exposure to bodily fluid droplets produced by a subject infected by the virus during coughing and/or sneezing. Beta-CoVs may induce fever and respiratory symptoms in humans. The SARS-CoV-2 receptor binding domain (RBD) of the spike protein binds to the human angiotensin-converting enzyme 2 (ACE2) receptor as a means for entering cells.

Diagnosis of SARS-CoV-2 may comprise a positive test for SARS-CoV-2 virus, viral RNA, subject antibodies against SARS-CoV-2 antigens, and/or onset of SARS-CoV-2 symptoms, or combinations thereof. The reagents and method described herein permit the diagnosis of infection of SARS-CoV-2 by reacting with antibodies produced by the subject in response to the SARS-CoV-2 infection. Symptoms of SARS-CoV-2 infection (COVID-19) include, but are not limited to, one or more of the following symptoms: nasal congestion, sore throat, fever, body aches, exhaustion, dry cough, difficulty breathing, or a combination thereof. Subjects at higher risk of developing complications may be immunocompromised (e.g., undergoing cancer treatment, bone marrow or organ transplantation, immune deficiencies, poorly controlled HIV or AIDS, prolonged use of corticosteroids or immune weakening medications), have an underlying medical condition (e.g., diabetes, renal failure, liver disease), are pregnant, are at least 65 years of age, have a chronic lung disease, have a heart disease, or combinations thereof.

Given the urgent need for evaluation of SARS-CoV-2-specific antibodies in a population for individual patients and the currently available tests with noted limitations, there is a significant need for rapid, simple, and affordable antibody tests with appropriate specificity and sensitivity. Such tests will allow decentralized testing of patients for SARS-CoV-2-specific antibodies, thus facilitating epidemiological management and vaccination efforts required to manage this pandemic effectively. Described herein is an assay based on (a) recombinant protein(s) that trigger(s) visible hemagglutination instantly in the presence of SARS-CoV-2 antibodies. The data provided herein establish proof of principle for this method.

The methods described herein are based on one or more recombinant fusion proteins containing at least three domains, i.e., a small camelid-derived antibody (nanobody) that binds to Glycophorin A (GYPA) on the surface of red blood cells (RBC) with high affinity, a SARS-CoV-2-specific immunogenic protein, such as the surface glycoprotein receptor “Spike” protein that serves as antigen for Corona-virus-directed antibodies, and an epitope-tag that is used for protein purification. The polypeptides also have an INF-β secretion sequence at the N-terminus to permit secretion from the expression cells. One embodiment described herein is the “NanoSpike,” (SEQ ID NO: 2) which refers to the respective nanobody and SARS-CoV-2 surface glycoprotein receptor “Spike” domains of the fusion protein (FIG. 1; Table 1). As described herein NanoSpike can efficiently be expressed in various mammalian cell lines and binds to the glycophorin protein on the surface of human red blood cells. Importantly, when added to whole blood containing SARS-CoV-2-specific antibodies of subjects infected with or convalescing from SARS-CoV-2, NanoSpike triggers instant hemagglutination that is easily detected by visual observation or other means such as optical density, impedance, microscopy, imaging, or applications developed for this purpose. Other embodiments useful in the assay include “NanoNuc” (SEQ ID NO: 4), “NanoORF8” (SEQ ID NO: 6), “NanoSpikeORF8” (SEQ ID NO: 8), “NanoORF3b” (SEQ ID NO: 10), and “NanoSpikeORF3b” (SEQ ID NO: 12), which refer to the nanobody and SARS-CoV-2 nucleocapsid, ORF 8, surface glycoprotein receptor binding domain and ORF 8, ORF 3b, and ORF 3b and surface glycoprotein receptor binding domains, respectively. Each of these fusion proteins permits the detection of subject antibodies against these various SARS-CoV-2 antigens. Polypeptide sequences of these constructs are shown in Table 1. The complete SARS-CoV-2 genome is disclosed in SEQ ID NO: 65 (GenBank: MT072688.1). Other SARS-CoV-2 viral polypeptides are potentially useful for alternative embodiments of the diagnostic or control polypeptides described herein.

Also described herein are fusion proteins that can serve as negative or positive controls for the method or assay described herein. In one embodiment, the fusion protein "NanoControl" (SEQ ID NO: 14) can be used as a negative control. NanoControl comprises the Glycophorin A nanobody domain, but no COVID domain. This polypeptide will not react with SARS-CoV-2-specific antibodies of subjects infected with or convalescing from SARS-CoV-2 when added to a sample of the subject's blood. This construct serves as a negative control.

Alternatively, the "NanoLink" (SEQ ID NO: 16) and "NanoTrim" (SEQ ID NO: 18) fusion proteins can be used as positive controls for the method or assay described herein. NanoLink and NanoTrim fusion proteins both contain two repeated SARS-CoV-2-specific nanobody (H11-D4) domains that recognize the receptor binding domain of SARS-CoV-2 spike protein [4]. NanoLink also contains a hinge region of an IgG FC domain (from the Etanercept sequence) which permits dimerization. Similarly, the NanoTrim fusion protein contains a hinge-isoleucine zipper domain which permits trimerization [5]. These control polypeptides also have an INF-β secretion sequence at the N-terminus to permit secretion from the expression cells.

The nanobody region of the NanoLink (SEQ ID NO: 16) and NanoTrim (SEQ ID NO: 18) constructs binds to the SARS-CoV-2 surface glycoprotein receptor biding domain (RBD) of the NanoSpike construct (or the NanoSpikeORF8 or NanoSpikeORF3b constructs, each of which contains the SARS-CoV-2 spike proteins RBD domain) and can cause hemagglutination (in the absence of a subject's anti-SARS-CoV-2 antibodies) and permits a side-by-side comparison of the assay results with assays conducted with NanoNuc (SEQ ID NO: 4), NanoORF8 (SEQ ID NO: 6), NanoSpikeORF8 (SEQ ID NO: 8), NanoORF3b (SEQ ID NO: 10), NanoSpikeORF3b and NanoControl (as a negative control). Collectively, these constructs permit a cross-validated assay that can be used to assess the presence of anti-SARS-CoV-2 antibodies in a subject's blood.

Polypeptide sequences of the NanoSpike, NanoNuc NanoORF8, NanoSpikeORF8, NanoORF3b, NanoSpikeORF3b, NanoControl, NanoLink, and NanoTrim constructs are shown in Table 1. Nucleic acid sequences are provided in the sequence listing (odd SEQ ID NOs of the even number polypeptide SEQ ID NOs).

TABLE 1

Nucleic acid sequences are provided in the sequence listing
(odd SEQ ID NOs of the even number polypeptide SEQ ID NOs).
Table 1. Polypeptide Constructs NanoSpike (SEQ ID NO: 1-2)
*MTNKCLLQIALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAARFPNITNLCPFGEVFNATRFASVYAWNRKRISNCVADYSVLYNSASFSTFKCYGVSPT
KLNDLCFTNVYADSFVIRGDEVRQIAPGQTGKIADYNYKLPDDFTGCVIAWNSNNLDSKVGGNYNYLYRLFRKSNL
KPFERDISTEIYQAGSTPCNGVEGFNCYFPLQSYGFQPTNGVGYQPYRVVVLSFELLHAPATVCGPKKSTNLEFGG
GSGGGSGGGSAWSHPQFEKGGGSGGGSGGSAWSHPQFEK
INF-β Secretion Sequence: Residues 1-22
Linkers: Residues 23-25; 149-170; 377-390
RBC Binding Domain: 26-148
COVID Spike Domain: 171-376
Dual Strep Tag: 391-419

NanoNuc (SEQ ID NO: 3-4)
*MTNKCLLQIALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAAMSDNGPQNQRNAPRITFGGPSDSTGSNQNGERSGARSKQRRPQGLPNNTASWFTALTQ
HGKEDLKFPRGQGVPINTNSSPDDQIGYYRRATRRIRGGDGKMKDLSPRWYFYYLGTGPEAGLPYGANKDGIIWVA
TEGALNTPKDHIGTRNPANNAAIVLQLPQGTTLPKGFYAEGSRGGSQASSRSSSRSRNSSRNSTPGSSRGTSPARM
AGNGGDAALALLLLDRLNQLESKMSGKGQQQQGQTVTKKSAAEASKKPRQKRTATKAYNVTQAFGRRGPEQTQGNF
GDQELIRQGTDYKHWPQIAQFAPSASAFFGMSRIGMEVTPSGTWLTYTGAIKLDDKDPNFKDQVILLNKHIDAYKT
FPPTEPKKDKKKKADETQALPQRQKKQQTVTLLPAADLDDFSKQLQQSMSSADSTQAEFGGGSGGGSGGGSAWSHP
QFEKGGGSGGGSGGSAWPQFEK
INF-β Secretion Sequence: Residues 1-22
Linkers: Residues 23-25; 149-170; 590-603
RBC Binding Domain: 26-148
COVID Nucleocapsid Domain: 171-589
Dual Strep Tag: 604-632

NanoORF8 (SEQ ID NO: 5-6)
*MTNKCLLQIALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAAQECSLQSCTQHQPYVVDDPCPIHFYSKWYIRVGARKSAPLIELCVDEAGSKSPIQYID
IGNYTVSCLPFTINCQEPKLGSLVVRCSFYEDFLEYHDVRVVLDFIPRGGGSGGGSGGGSAWSHPQFEKGGGSGGG
SGGSAWSHPQFEK
INF-β Secretion Sequence: Residues 1-22
Linkers: Residues 23-25; 149-170; 274-288
RBC Binding Domain: 26-148
COVID ORF 8 Domain: 171-273
Dual Strep Tag: 289-317

TABLE 1-continued

Nucleic acid sequences are provided in the sequence listing
(odd SEQ ID NOs of the even number polypeptide SEQ ID NOs).
Table 1. Polypeptide Constructs NanoSpikeORF8 (SEQ ID NO: 7-8)
*MTNKCLLQIALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAARFPNITNLCPFGEVFNATRFASVYAWNRKRISNCVADYSVLYNSASFSTFKCYGVSPT
KLNDLCFTNVYADSFVIRGDEVRQIAPGQTGKIADYNYKLPDDFTGCVIAWNSNNLDSKVGGNYNYLYRLFRKSNL
KPFERDISTEIYQAGSTPCNGVEGFNCYFPLQSYGFQPTNGVGYQPYRVVVLSFELLHAPATVCGPKKSTNLEFSG
GGGSGGGGSGGGGSAAAQECSLQSCTQHQPYVVDDPCPIRFYSKWYIRVGARKSAPLIEYCVDEAGSKSPTQYIDI
GNYTVSCLPFTINCQEPKLGSLVVPCSFYEDFLEYHDVRVVLLFIPRGGGSGGGSGGGSAWSHPQFEKGGGSGGGS
GGSAWSHPQFEK
INF-β Secretion Sequence: Residues 1-22
Linkers: Residues 23-25; 149-170; 377-397; 501-515
RBC Binding Domain: 26-148
COVID Spike Domain: 171-376
COVID ORF 8 Domain: 398-500
Dual Strep Tag: 516-544

NanoORF3b (SEQ ID NO: 9-10)
*MTNKCLLQIALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAAMAYCWRCTSCCFSERFQNHNPQKEMATSTLQGCSLCLQLAVVVNSLLTPFARCCWPEF
GGGSGGGSGGGSAWSHPQFEKGGGSGGGSGGSAWSHPQFEK
INF-β Secretion Sequence: Residues 1-22
Linkers: Residues 23-25; 149-170; 227-240
RBC Binding Domain: 26-148
COVID ORF 3b Domain: 171-226
Dual Strep Tag: 241-269

NanoSpikeORF3b (SEQ ID NO: 11-12)
*MTNKCLLQIALLLCFSTTALSM*GAPQVQLQESGGGSVQAGGSLRLSCVASGYTDSTYCVGWFRQAPGKEREGVARI
NTISGRPWYADSVKGRFTISQDNSKNTVYLQMNSLKPEDTAIYYCTLTTANSRGFCSGGYNYKGQGTQVTVSGGTS
GGGGSGGGGSGGGGSAAARFPNITNLCPFGEVFNATRFASVYAWNRKRISNCVADYSVLYNSASFSTFKCYGVSPT
KLNDLCFTNVYADSFVIRGDEVRQIAPGQTGKIADYNYKLPDDFTGCVIAWNSNNLDSKVGGNYNYLYRLFRKSNL
KPFERDISTEIYQAGSTPCNGVEGFNCYFPLQSYGFQPTNGVGYQPYRVVVLSFELLHAPATVCGPKKSTNLEFSG
GGGSGGGGSGGGGSAAAMAYCWRCTSCCFSEPFQNHNPQKEMATSTLQGCSLCLQLAVVVNSLLTPFARCCWPEFG
GGSGGGSGGGSAWSHPQFEKGGGSGGGSGGSAWSHPQFEK
INF-β Secretion Sequence: Residues 1-22
Linkers: Residues 23-25; 149-170; 377-397; 454-467
RBC Binding Domain: 26-148
COVID Spike Domain: 171-376
COVID ORF 3b Domain: 398-453
Dual Strep Tag: 467-496

NanoControl (SEQ ID NO: 13-14)
*MTNKCLLQIALLLCFSTTALSM*GAPQVQLQESGGGSVQAGGSLRLSCVASGYTDSTYCVGWFRQAPGKEREGVARI
NTTSGRPWYADSVKGRFTISQDNSKNTVYLQMNSLKPEDTAIYYCTLTTANSRGFCSGGYNYKGQGTQVTVSGEFG
GGSGGGSGGGSAWSHPQFEKGGGSGGGSGGSAWSHPQFEK
INF-β Secretion Sequence: Residues 1-22
Linkers: Residues 23-25; 149-163
RBC Binding Domain: 26-148
Dual Strep Tag: 164-192

NanoLink (SEQ ID NO:16)
*MTNKCLLQIALLLCFSTTALSM*GAPQVQLVESGGGLMQAGGSLRLSCAVSGRTFSTAAMGWFRQAPGKEREFVAAI
RWSGGSAYYADSVKGRFTISRDKAKNTVYLQMNSLKYEDTAVYYCARTENVRSLLSDYATWPYDYWGQGTQVTVSG
GGGSGGGGSGGGGSIDQVQLVESGGGLMQAGGSLRLSCAVSGRTFSTAAMGWFRQAPGKEREFVAAIRWSGGSAYY
ADSVKGRFTISRDKAKNTVYLQMNSLKYEDTAVYYCARTENVRSLLSDYATWPYDYWGQGTQVTVSSGTGGGGSGG
GGSGGGGSGSEPKSCDKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGNVFSCSVMHEALH
NHYTQKSLSLSPGKPRGGGSGGGSGGGSAAAWSHPQFEKGGGSGGGSGGGSWSHPQFEK
INF-β Secretion Sequence: Residues 1-22
Linkers: Residues 23-25; 152-168; 295-314; 547-562
SARS-CoV-2 Spike RBD specific nanobody (H11-D4): 26-151; 169-294
IgG-FC Dimerization domain: 315-546
Dual Strep Tag: 563-591

NanoTrim (SEQ ID NO: 17-18)
*MTNKCLLQIALLLCFSTTALSM*GAPQVQLVESGGGLMQAGGSLRLSCAVSGRTFSTAAMGWFRQAPGKEREFVAAI
RWSGGSAYYADSVKGRFTISRDKAKNTVYLQMNSLKYEDTAVYYCARTENVRSLLSDYATWPYDYWGQGTQVTVSG
GGGSGGGGSGGGGSIDQVQLVESGGGLMQAGGSLRLSCAVSGRTFSTAAMGWFRQAPGKEREFVAAIRWSGGSAYY
ADSVKGRFTISRDKAKNTVYLQMNSLKYEDTAVYYCARTENVRSLLSDYATWPYDYWGQGTQVTVSSGTEPKLPQP
QPKPQPQPQPQPKPQPKPEPEQRMKQIEDKIEEILSKIYHIENEIARIKKLVGERPRGGGSGGGSGGGSAAAWSHP
QFEKGGGSGGGSGGGSWPQFEK TABLE 1-continued

| Nucleic acid sequences are provided in the sequence listing (odd SEQ ID NOs of the even number polypeptide SEQ ID NOs). Table 1. Polypeptide Constructs |
|---|
| INF-β Secretion Sequence: Residues 1-22<br>Linkers: Residues 23-25; 152-168; 295-297; 360-375<br>SARS-CoV-2 Spike RBD specific nanobody (H11-D4): 26-151; 169-294<br>Hinge-isoleucine zipper domain (trimerization domain): 298-359<br>Dual Strep Tag: 376-404 |

Odd number SEQ ID NO are nucleotide sequences; event numbers are polypeptide sequences The fusion proteins listed in Table 1 can be expressed in mammalian cells and particularly in human cell lines. In one embodiment the proteins are expressed in human embryonic kidney 293 cells (HEK 293). In another aspect, the proteins are expressed in Expi293F™ Cells (Thermo Fisher Scientific). The proteins are secreted into the media and are purified using affinity chromatography. In one aspect, the proteins are purified using Strep-Tactin®X (IBA) resin or beads on a column or batch format. The purified proteins were desalted and concentrated. Further polishing steps can be performed using ion exchange, gel filtration, or other chromatographic methods known in the art.

The diagnostic assays described herein require a minimal amount of whole blood (e.g., from a finger prick). Alternatively, subject plasma or serum can be used when combined with human red blood cells (e.g., from the subject or washed human red blood cells of blood group O). A small amount of blood (e.g., 10-20 µL is typically combined with the test or control solutions (concentration of NanoSpike or other constructs: 20-60 µg/mL) at a ratio of ~1:1 in an appropriate vessel (microfuge tub) or directly on a test card; gently mixed; and the reaction mixture is spread over the test card field (~1 $cm^2$ diameter). The test card is rotated manually or with a mechanical rotor at 80-100 rpm for up to about 2-5 minutes and immediately read under direct light. The presence of hemagglutination (aggregation of red blood cells) is a positive result that indicates the presence of subject antibodies against SARS-CoV-2 antigens (e.g., surface glycoprotein, nucleocapsid, ORF8, OR3b, or a combination thereof).

The assay method described herein was validated using 40 COVID19-positive subjects (and 42 control subjects), with 98% sensitivity and 98% specificity. This assay enables simple, rapid, sensitive, specific, and inexpensive diagnosis and identification of subjects with SARS-CoV-2-specific antibodies, either as result of previous infection or successful vaccination. Information provided by this test is be valuable for epidemiological surveillance and decisions related to forthcoming vaccination efforts.

One embodiment described herein is a nucleotide sequence encoding a polypeptide, wherein the polypeptide comprises a human red blood cell binding antibody domain (RBD) and a SARS CoV-2 virus protein domain (CVD). In one aspect, the RBD comprises a glycophorin A-binding nanobody comprising 90-99% identity to SEQ ID NO: 22. In another aspect, the CVD comprises one or more of a spike protein, a nucleocapsid protein, ORF8 protein, ORF3b protein, or envelope protein comprising 90-99% identity to all or a portion of SEQ ID NO: 24, 26, 28, or 30.

In one aspect, the polypeptide has the structure:

SS-GAP-RBD-GL2-CVD-GL3-AFT or

SS-GL1-RBD-GL2-CVD-GL3-CVD-GL4-AFT;

wherein:

SS is a secretion signal domain;

RBD is a glycophorin A-binding nanobody domain;

GAP, GL1, GL2, GL3, and GL4 are linker domains;

CVD is a SARS CoV-2 virus polypeptide domain comprising a spike protein, nucleocapsid protein, ORF8 protein, ORF3b protein, or envelope protein domains; and AFT is an affinity purification tag sequence.

In another aspect, the SS comprises 90-99% identity to SEQ ID NO: 20. In another aspect, the GAP, GL1, GL2, GL3, or GL4 comprises 90-99% identity to one or more of SEQ ID NO: 38, 40, 42, 44, or 46. In another aspect, the AFT comprises 90-99% identity to one or more of SEQ ID NO: 58, 60, 62, or 64. In another aspect, the nucleotide sequence has 90% to 99% identity to SEQ ID NO: 1, 3, 5, 7, 9, or 11. In another aspect, the nucleotide sequence is one of SEQ ID NO: 1, 3, 5, 7, 9, or 11.

Another embodiment described herein is a polynucleotide vector comprising a nucleotide sequence described herein.

Another embodiment described herein is a cell comprising a polynucleotide vector comprising a nucleotide sequence described herein.

Another embodiment described herein is a polypeptide encoded by a nucleotide sequence described herein.

Another embodiment described herein is a polypeptide encoded by a nucleotide sequence described herein, wherein the polypeptide has 90% to 99% identity to SEQ ID NO: 2, 4, 6, 8, 10, or 12.

Another embodiment described herein is a polypeptide encoded by a nucleotide sequence described herein, wherein the polypeptide is SEQ ID NO: 2, 4, 6, 8, 10, or 12.

Another embodiment described herein is a diagnostic reagent or research tool comprising a polypeptide encoded by the nucleotide sequence described herein.

Another embodiment described herein is a method or means for manufacturing a nucleotide sequence as described herein or a polypeptide encoded by the nucleotide sequence, the process comprising: transforming or transfecting a cell with a nucleic acid comprising the nucleotide sequence; growing the cells; optionally, harvesting the cells and isolating quantities of the nucleotide sequence; inducing expression of a polypeptide encoded by the nucleotide sequence; harvesting the cells; and isolating and purifying the polypeptide.

Another embodiment described herein is a nucleotide sequence or a polypeptide encoded by the nucleotide sequence, each produced by a method or means described herein.

Another embodiment described herein is a nucleotide sequence encoding a diagnostic control polypeptide, wherein the polypeptide comprises: (a) a glycophorin A-binding nanobody domain comprising 90-99% identity to SEQ ID NO: 22; (b) one or more anti-SARS Co-V-2 nanobody domains comprising 90-99% identity to SEQ ID NO: 32 and one or more multimerization domains comprising 90-99% identity to SEQ ID NO: 34 or 36.

In one aspect, the polypeptides have the structure:

SS-GAP-RBD-GL5-AFT;

SS-GAP-anti-CVD-GL6-anti-CVD-GL7-IgGFC-GL8-AFT; or

SS-GAP-anti-CVD-GL6-anti-CVD-SGT-HIZD-GL8-AFT;

wherein:

SS is a secretion signal domain;

RBD is a glycophorin A-binding nanobody domain;

GAP, GL5, GL6, GL7, GL8, and SGT are linker domains;

Anti-CVD is an anti-SARS CoV-2 surface glycoprotein receptor binding domain nanobody domain;

IgGFC is a human immunoglobulin FC dimerization domain;

HIZD is a Hinge-isoleucine zipper trimerization domain; and

AFT is an affinity purification tag sequence.

In another aspect, the SS comprises 90-99% identity to SEQ ID NO: 20. In another aspect, the GAP, SGT, GL5, GL6, GL7, or GL8 comprises 90-99% identity to one or more of SEQ ID NO: 38, 48, 50, 52, 54, or 56. In another aspect, the AFT comprises 90-99% identity to one or more of SEQ ID NO: 58, 60, 62, or 64. In another aspect, the nucleotide sequence has 90% to 99% identity to SEQ ID NO: 13, 15, or 17. In another aspect, the nucleotide sequence is one of SEQ ID NO: 13, 15, or 17.

Another embodiment described herein is a polynucleotide vector comprising a nucleotide sequence encoding a diagnostic control polypeptide as described herein.

Another embodiment described herein is a cell comprising a polynucleotide vector comprising a nucleotide sequence encoding a diagnostic control polypeptide as described herein.

Another embodiment described herein is a diagnostic control polypeptide as described herein.

Another embodiment described herein is a diagnostic control polypeptide having 90% to 99% identity to SEQ ID NO: 14, 16, or 18.

Another embodiment described herein is a diagnostic control polypeptide having the polypeptide sequence of SEQ ID NO: 14, 16, or 18.

Another embodiment described herein is a diagnostic reagent or research tool comprising a polypeptide encoded by a nucleotide sequence described herein.

Another embodiment described herein is a diagnostic or control polypeptide comprising the amino acid sequence of SEQ ID NO: 2, 4, 6, 8, 10, 12, 14, 16, or 18.

Another embodiment described herein is a method for evaluating whether a subject is infected or has been infected with SARS-CoV-2, the method comprising: (a) providing a sample of a biological fluid from a subject in need of diagnosis; (b) combining the biological fluid with a diagnostic polypeptide comprising 90 to 99% identity to the amino acid sequence of SEQ ID NO: 2, 4, 6, 8, 10, 12 to form a subject sample; (c) optionally, combining a negative control reagent or a positive control polypeptide comprising 90 to 95% identity to the amino acid sequence of SEQ ID NO: 14 (negative control) or SEQ ID NO: 16 or 18 (positive controls), with the biological fluid and a diagnostic polypeptide comprising 90 to 99% identity to the amino acid sequence of SEQ ID NO: 2, 10, or 12 to form one or more control samples; (d) permitting the subject sample and control samples to incubate for a period of time; (e) evaluating the results by visualization, imaging, optical density, impedance, or microscopy; and (f) optionally, comparing the subject sample and control samples to validate the subject sample results; wherein the presence of hemagglutination in the subject sample is a positive diagnostic indication of SARS-CoV-2 infection, and the absence of hemagglutination in the subject sample is a negative diagnostic indication of SARS-CoV-2 infection. In one aspect, the biological fluid is whole blood, plasma, or serum. In another aspect, when the biological fluid is plasma or serum, washed human red blood cells of blood group 0 are combined with the subject sample and the diagnostic or control polypeptides in steps (b) or (c). In another aspect, wherein the diagnostic or control polypeptides have a concentration of about 10 μg/mL to about 100 μg/mL. In another aspect, the subject sample and/or control samples in steps (b) and/or (c) are dispensed on a test card, glass slide, microtiter plate, or other substrate prior to step (d). In another aspect, when the subject sample has a positive diagnostic indication of SARS-CoV-2 infection, the method further comprises: (g) administering one or more therapeutics or treatments to the subject.

Another embodiment described herein is a kit comprising: (a) one or more diagnostic or control polypeptides comprising the amino acid sequence of SEQ ID NO: 2, 4, 6, 8, 10, 12, 14, 16, or 18; (b) a test substrate; and (c) optionally, a label or instructions for use. In one aspect, the kit further comprises one or more of alcohol saturated towelettes; finger prick lances, capillaries, or gloves.

Another embodiment described herein is the use of a polypeptide comprising 90 to 99% identity to the amino acid sequence of SEQ ID NO: 2, 4, 6, 8, 10, 12, 14, 16, or 18 for the diagnosis of SARS-CoV-2 in a subject in need of diagnosis thereof.

Another embodiment described herein is a polynucleotide vector comprising one or more nucleotide sequences described herein. In one aspect, the nucleotide sequence comprises 85% to 100% identity to SEQ ID NO: 1, 3, 5, 7, 9, 11, 13, 15, or 17 and encodes a polypeptide having 85% to 100% identity to SEQ ID NO: 2, 4, 6, 8, 10, 12, 14, 16, or 18.

Another embodiment described herein is a cell comprising one or more nucleotide sequences described herein or a polynucleotide vector described herein encoding one or more polypeptides. In one aspect, the nucleotide sequence has 85% to 100% identity to SEQ ID NO: 1, 3, 5, 7, 9, 11, 13, 15, or 17 and the encoded polypeptide has 85% to 100% identity to SEQ ID NO: 2, 4, 6, 8, 10, 12, 14, 16, or 18.

Another embodiment is a diagnostic or control polypeptide encoded by a nucleotide sequence described herein. In one aspect, the nucleotide sequence has 85% to 100% identity to SEQ ID NO: 1, 3, 5, 7, 9, 11, 13, 15, or 17 and the encoded polypeptide has 85% to 100% identity to SEQ ID NO: 2, 4, 6, 8, 10, 12, 14, 16, or 18. In another aspect, the diagnostic polypeptide is selected from SEQ ID NO: 2, 4, 6, 8, 10, or 12. In another aspect the control polypeptide is selected from SEQ ID NO: 14, 16, or 18

Another embodiment described herein is a process for manufacturing one or more of the nucleotide sequence described herein or a polypeptide encoded by the nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence of described herein; isolating the polypeptide encoded by a nucleotide described herein.

Another embodiment described herein is a means for manufacturing one or more of the nucleotide sequences described herein or a polypeptide encoded by a nucleotide sequence described herein, the process comprising: transforming or transfecting a cell with a nucleic acid comprising a nucleotide sequence described herein; growing the cells; optionally isolating additional quantities of a nucleotide sequence described herein; inducing expression of a polypeptide encoded by a nucleotide sequence of described herein; isolating the polypeptide encoded by a nucleotide described herein.

Another embodiment described herein is a nucleotide sequence or a polypeptide encoded by the nucleotide sequence produced by the method or the means described herein Another embodiment described herein is the use of an effective amount of a polypeptide encoded by one or more of the nucleotide sequences described herein having 85% to 100% identity to SEQ ID NO: 1, 3, 5, 7, 9, 11, 13, 15, 17.

Another embodiment described herein is a research tool comprising a polypeptide encoded by a nucleotide sequence described herein.

Another embodiment described herein is an analytical reagent comprising a polypeptide encoded by a nucleotide sequence described herein.

The polynucleotides described herein include variants that have substitutions, deletions, and/or additions that can involve one or more nucleotides. The variants can be altered in coding regions, non-coding regions, or both. Alterations in the coding regions can produce conservative or non-conservative amino acid substitutions, deletions, or additions. Especially preferred among these are silent substitutions, additions, and deletions, which do not alter the properties and activities of the binding.

Further embodiments described herein include nucleic acid molecules comprising polynucleotides having nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90-99% or 100% identical to (a) nucleotide sequences, or degenerate, homologous, or codon-optimized variants thereof, encoding polypeptides having the amino acid sequences in SEQ ID NO: 2, 4, 6, 8, 10, 12, 14, 16, or 18 (b) nucleotide sequences, or degenerate, homologous, or codon-optimized variants thereof, encoding polypeptides having the amino acid sequences in SEQ ID NO: 2, 4, 6, 8, 10, 12, 14, 16, or 18; and (c) nucleotide sequences capable of hybridizing to the complement of any of the nucleotide sequences in (a) or (b) above and capable of expressing functional polypeptides of amino acid sequences in SEQ ID NO: 2, 4, 6, 8, 10, 12, 14, 16, or 18.

By a polynucleotide having a nucleotide sequence at least, for example, 90-99% "identical" to a reference nucleotide sequence encoding a polypeptide of SEQ ID NO: 2, 4, 6, 8, 10, 12, 14, 16, or 18 is intended that the nucleotide sequence encoding the polynucleotide be identical to the reference sequence except that the polynucleotide sequence can include up to about 10 to 1 point mutations, additions, or deletions per each 100 nucleotides of the reference nucleotide sequence encoding a polypeptide of SEQ ID NO: 2, 4, 6, 8, 10, 12, 14, 16, or 18.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence. The same is applicable to polypeptide sequences about at least 90-99% identical to a reference polypeptide sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2: 4 82-489 (1981). This algorithm can be extended to use with peptide sequences using the scoring matrix developed by Dayhoff, *Atlas of Protein Sequences and Structure*, M. O. Dayhoff ed., 5 suppl. 3: 353-358, National Biomedical Research Foundation, Washington, D.C., USA, and normalized by Gribskov, *Nucl. Acids Res.* 14(6): 6745-6763 (1986).

For example, due to the degeneracy of the genetic code, one having ordinary skill in the art will recognize that a large number of the nucleic acid molecules having a sequence at least 50%, 55%, 60%, 65%, 70%, 75%, 80%, 85%, 90%, 91%, 92%, 93%, 94%, 95%, 96%, 97%, 98%, 99%, or 100% identical to the nucleic acid sequence shown in SEQ ID NO: 1, 3, 5, 7, 9, 11, 13, 15, or 17, or degenerate, homologous, or codon-optimized variants thereof, will encode a polypeptide having a sequence at least 50%, 55%, 60%, 65%, 70%, 75%, 80%, 85%, 90%, 91%, 92%, 93%, 94%, 95%, 96%, 97%, 98%, 99%, or 100% identical to the polypeptide sequence shown in SEQ ID NO: 2, 4, 6, 8, 10, 12, 14, 16, or 18.

The polynucleotides described herein include those encoding mutations, variations, substitutions, additions, deletions, and particular examples of the polypeptides described herein. For example, guidance concerning how to make phenotypically silent amino acid substitutions is provided in Bowie, J. U. et al., "Deciphering the Message in Protein Sequences: Tolerance to Amino Acid Substitutions," *Science* 247: 1306-1310 (1990), wherein the authors indicate that proteins are surprisingly tolerant of amino acid substitutions.

Thus, fragments, derivatives, or analogs of the polypeptides of SEQ ID NO: 2, 4, 6, 8, 10, 12, 14, 16, or 18 can be (i) ones in which one or more of the amino acid residues (e.g., 1, 2, 3, 4, 5, 7, 8, 9, 10, 11, 12, 13, 14, 15, 16, 17, 18, 19, 20, 25, 30, 35, 40, 45, or 50 residues, or even more) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 1, 2, 3, 4, 5, 7, 8, 9, 10, 15, 20, 25, 30, 35, 40, 45, or 50 residues or even more), or (iii) ones in which the mature polypeptide is fused with another polypeptide or compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

In addition, fragments, derivatives, or analogs of the polypeptides of SEQ ID NO: 2, 4, 6, 8, 10, 12, 14, 16, or 18 can be substituted with one or more conserved or non-conserved amino acid residue (preferably a conserved amino acid residue). In some cases these polypeptides, fragments, derivatives, or analogs thereof will have a polypeptide sequence at least 50%, 55%, 60%, 65%, 70%, 75%, 80%, 85%, 90%, 91%, 92%, 93%, 94%, 95%, 96%, 97%, 98%, 99% or 100% identical to the polypeptide sequence shown in SEQ ID NO: 2, 4, 6, 8, 10, 12, 14, 16, or 18 and will comprise functional or non-functional proteins or enzymes. Similarly, additions or deletions to the polypeptides can be made either at the N- or C-termini or within non-conserved regions of the polypeptide (which are assumed to be non-critical because they have not been photogenically conserved).

As described herein, in many cases the amino acid substitutions, mutations, additions, or deletions are preferably of a minor nature, such as conservative amino acid substitutions that do not significantly affect the folding or activity of the protein or additions or deletions to the N- or C-termini. Of course, the number of amino acid substitutions, additions, or deletions a skilled artisan would make depends on many factors, including those described herein. Generally, the number of substitutions, additions, or deletions for any given polypeptide will not be more than about 100, 90, 80, 70, 60, 50, 40, 30, 25, 20, 19, 18, 17, 16, 15, 14, 13, 12, 11, 10, 9, 8, 7, 5, 6, 4, 3, 2, or 1.

It will be apparent to one of ordinary skill in the relevant art that suitable modifications and adaptations to the compositions, formulations, methods, processes, apparata, assemblies, and applications described herein can be made without departing from the scope of any embodiments or aspects thereof. The compositions, apparata, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparata, assemblies, and processes described herein include all actual or potential combinations of embodiments, aspects, options, examples, and preferences described herein. The compositions, formulations, apparata, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

REFERENCES

1. Kontou et al., "Antibody Tests in Detecting SARS-CoV-2 Infection: A Meta-Analysis," *Diagnostics* (Basel) 10(5): 319 (2020).
2. Gudbjartsson et al., "Humoral Immune Response to SARS-CoV-2 in Iceland," *N. Engl. J. Med.* 383(18):1724-1734 (2020).
3. Hachim et al., "ORF8 and ORF3b antibodies are accurate serological markers of early and late SARS-CoV-2 infection," *Nat. Immunol.* 21(10):1293-1301 (2020).
4. Huo et al., "Neutralizing nanobodies bind SARS-CoV-2 spike RBD and block interaction with ACE2," *Nat. Struct. Mol. Biol.* 27(9): 846-854 (2020).
5. Tillib et al., "Formatted single-domain antibodies can protect mice against infection with influenza virus (H5N2)," *Antiviral Res.* 97(3):245-254 (2013).
6. Redecke et al., "Hematopoietic progenitor cell lines with myeloid and lymphoid potential," *Nat. Methods* 10(8): 795-803 (2013).
7. Lee et al., "Production of specific antibodies against SARS-coronavirus nucleocapsid protein without cross reactivity with human coronaviruses 229E and OC43," *J. Vet. Sci.* 11(2): 165-167 (2010).
8. Lee et al., "Detection of antibodies against SARS-Coronavirus using recombinant truncated nucleocapsid proteins by ELISA," *J. Microbiol. Biotechnol.* 18(10): 1717-1721 (2008).
9. Dutta et al., "Search for potential target site of nucleocapsid gene for the design of an epitope-based SARS DNA vaccine," *Immunol. Let.* 118(1): 65-71 (2008).
10. Gupta and Chaudhary, "Whole-blood agglutination assay for on-site detection of human immunodeficiency virus infection," *J. Clin. Microbiol.* 41(7): 2814-2821 (2003).
11. Kemp et al., "Autologous red cell agglutination assay for HIV-1 antibodies: simplified test with whole blood," *Science* 241(4871):1352-1354 (1988).
12. Gupta and Chaudhary, "Expression, purification, and characterization of an anti-RBCFab-p24 fusion protein for hemagglutination-based rapid detection of antibodies to HIV in whole blood," *Protein Expr. Purif.* 26(1): 162-170 (2002).
13. Habib et al., "V(H)H (nanobody) directed against human glycophorin A: a tool for autologous red cell agglutination assays," *Anal. Biochem.* 438(1): 82-89 (2013).
14. Tai et al., "Characterization of the receptor-binding domain (RBD) of 2019 novel coronavirus: implication for development of RBD protein as a viral attachment inhibitor and vaccine," *Cell. Mol. Immunol.* 17(6): 613-620 (2020).
15. Ravichandran et al., "Antibody signature induced by SARS-CoV-2 spike protein immunogens in rabbits," *Sci. Transl. Med.* 12(550): eabc3539 (2020).
16. Grzelak et al., "A comparison of four serological assays for detecting anti-SARS-CoV-2 antibodies in human serum samples from different populations," *Sci. Transl. Med.* 12(559): eabc3103 (2020).

EXAMPLES

Example 1

Plasmids

DNA encoding expressed proteins was synthesized by commercial suppliers (Thermo Fisher Scientific/Invitrogen, Synbio, Biomatic) and cloned by standard molecular biology methods into the mammalian expression vector pcDNA3.1(+) (Invitrogen). All coding sequences were confirmed by Sanger sequencing.

Protein Expression

All proteins were expressed in Expi293F™ cells (Thermo Fisher Scientific) using the ExpiFectamine™ 293 Transfection Kit following the manufacturer's instructions (Thermo Fisher Scientific). In brief, cells were cultured at 37° C. and 8% $CO_2$ in 25 mL of Expi293 expression medium (Thermo Fisher Scientific) in 125 mL bottles on a 25 mm orbital shaker (120 rpm) until reaching a density of 4.5-5.5×$10^6$/mL. Cells were seeded at 3×$10^6$/mL in 25 mL per 125 mL flasks for transfection. 25 μg of DNA and 80 μL of Epifectamine was added to 1.5 mL and 1.4 mL Opti-Plex complexation buffer (Thermo Fisher Scientific), respectively. After a 3-5 min incubation at room temperature (RT), the two solutions were combined, gently mixed, incubated for 15 min at RT and added dropwise to cells. After overnight culture, Epifectamine transfection enhancer 1 (150 μL) and Epifectamine transfection enhancer 2 (1.5 mL) was added, and cell suspensions were harvested two days later.

Protein Purification

Cell suspensions were centrifuged at 450 g for 5 min and protein-containing supernatant was cleared using 0.2 μm filter bottles. To remove biotin (interfering with affinity purification), 3 mL of 10× buffer W (1M Tris-HCl pH 8.0, 1.5 M NaCl, 10 mM EDTA) was added to the supernatant along with 600 μL of BioLock solution (IBA), followed by ultracentrifugation at 20,000×g for 20 min at 4° C. The resulting supernatant was loaded on columns containing 700 μL of washed Strep-Tactin® XT matrix (IBA). The columns were rinsed five times with 1 mL ice-cold PBS, proteins were eluted with 3×500 μL of buffer BXT (IBA), concentrated on Amicon Ultra3k concentration columns (3 kD cutoff) at 14,000×g at 4° C. and desalted by centrifugation at 1500×g for 2 min using TBS-equilibrated Zeba Spin desalting columns (0.5 mL, 7 k MWCO, Thermo Fisher Scientific). 3-10 μg of each purified proteins was analyzed by SDS PAGE and Sypro Ruby staining (Thermo Fisher Scientific).

Example 2

Design, Expression and Purification of Recombinant Proteins

Figure 3:
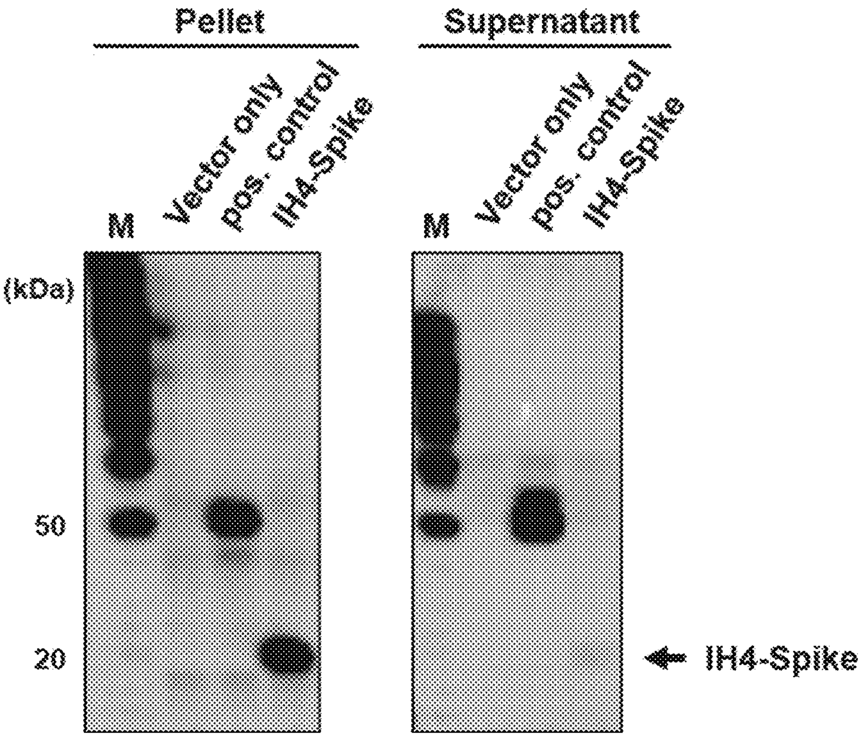
FIG. 3 shows a fusion protein of the IH4 nanobody and the Spike RBD is not efficiently secreted. A fusion construct of the IH4 nanobody (SEQ ID NO: 65-66) and the Spike-RBD (IH4-Spike) was transfected into HEK293T cells along with a negative (vector) control and a positive control construct, and protein expression was analyzed in the cell pellet and the supernatant. Note the almost complete lack or IH4-Spike in the supernatant. Vector only-transfected cells (vector only) and cells transfected with a secreted control protein (positive control) show expected results.
Figure 4:
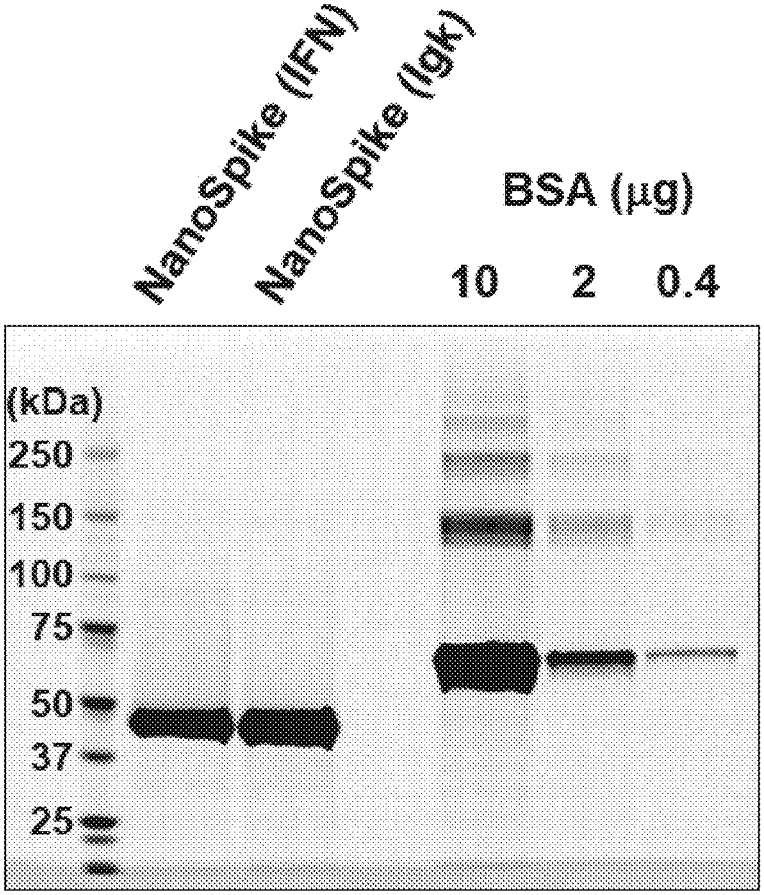
FIG. 4 shows two mutations in the IH4 nanobody permit efficient secretion of Spike-RBD fusion proteins. Fusion constructs with modified forms of IH4 (IH4vs2) (SEQ ID NO:21-22), i.e., IH4vs2-Spike (i.e., "NanoSpike"; SEQ ID NO:1-2) and a similar construct containing an Igk-leader sequence (instead of the Ifnb leader sequence of NanoSpike) were purified from the supernatant of transfected Expi293F™ (Thermo Fisher Scientific) cells, followed by SDS PAGE and protein (Sypro Ruby) stain. Protein yield from 25 mL of Expi293F™ cell cultures were 2.3 mg (NanoSpike) and 2.9 mg (NanoSpike-Igk). BSA at 10 μg, 2 μg, and 0.4 μg is shown for comparison.
Figure 5:
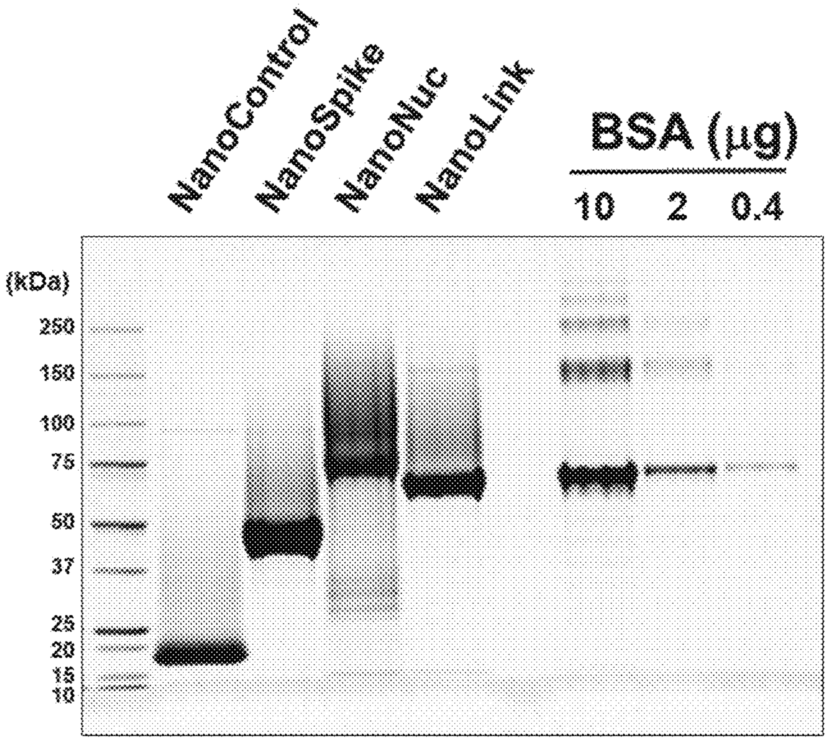
FIG. 5 shows an example of recombinant protein production. Indicated proteins were expressed in Expi293F™ (Thermo Fisher Scientific) cells and purified by affinity purification followed by SDS PAGE and protein (Sypro Ruby) stain. Protein yield from 25 mL of Expi293F™ cell cultures were 2 mg (NanoControl; SEQ ID NO: 14), 3.75 mg (NanoSpike; SEQ ID NO: 2), 0.55 mg (NanoNuc; SEQ ID NO: 4) and 1.25 mg (NanoLink; SEQ ID NO: 16). BSA at 10 μg, 2 μg, and 0.4 μg is shown for comparison.

Due to the known robustness of nanobodies and the availability of required sequence information. Methodologically, a modified form of the IH4 nanobody (IH4vs2) was fused to the receptor-binding domain of the Spike protein of SARS-CoV-2, which has been shown in various analyses to represent a highly immunogenic region [6-8]. Mammalian cells were used for protein expression. The SARS Co-V-2 surface "spike" glycoprotein is physiologically targeted to the secretory pathway, which is likely required for proper protein folding and accompanied by glycosylation, which in turn may be relevant for the antibody response and thus test specificity [9]. To allow for proper targeting to the secretory pathway, a secretion signal derived from interferon-β was fused to the N-terminus of the fusion protein (FIG. 1). A tandem Strep-tag was fused to the C-terminus to allow for efficient one-step protein purification. Flexible glycine-serine-containing linkers were placed between the functional units of the fusion protein to avoid interference of the different domains. A similar protein lacking the Spike RBD was cloned as negative control (FIG. 1). The proteins were expressed first in small scale, then in larger scale experiments in either ExpiCho-S™ or Expi293F™ cells (Thermo Fisher Scientific), both of which are optimized for high density growth in suspension and used extensively in the pharmaceutical industry. As shown for experiments based on Expi293F™ cells, protein expression and Strep-tag-based one-step purification was very efficient, resulting in virtually homogenous protein preparations for both the NanoSpike and the NanoControl protein (FIG. 3-5). Around 2 mg of protein were obtained from 30 mL of cell culture, reflecting a highly efficient process.

Example 3

Functional Activity of Recombinant Proteins in Hemagglutination Assays

Figure 6:
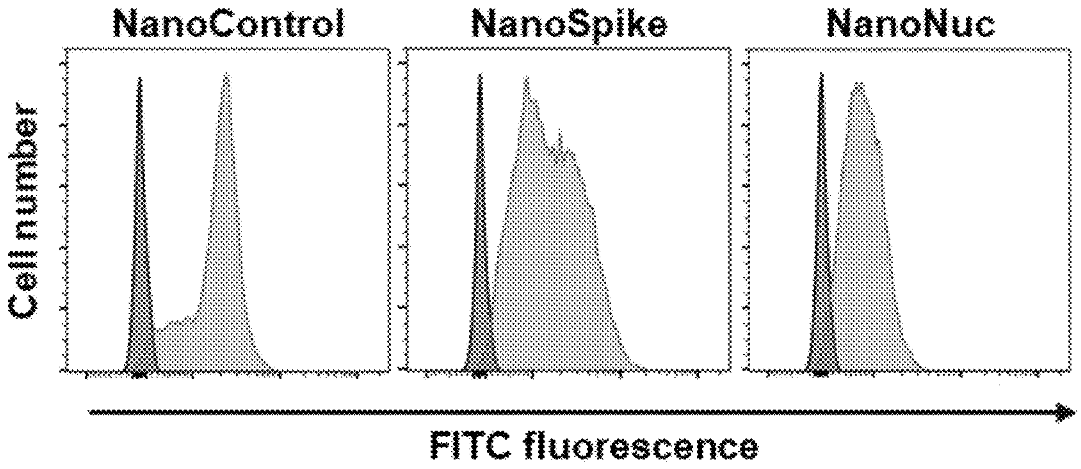
FIG. 6 shows that recombinant proteins containing the Glycophorin A-binding nanobody IH4vs2 bind human red blood cells. Flow cytometry analysis of human RBC that were treated with 30 μg/mL recombinant proteins (as indicated), followed by incubation without (dark) or with FITC-labeled antibody against the Strep-tag (light).
Figure 7:
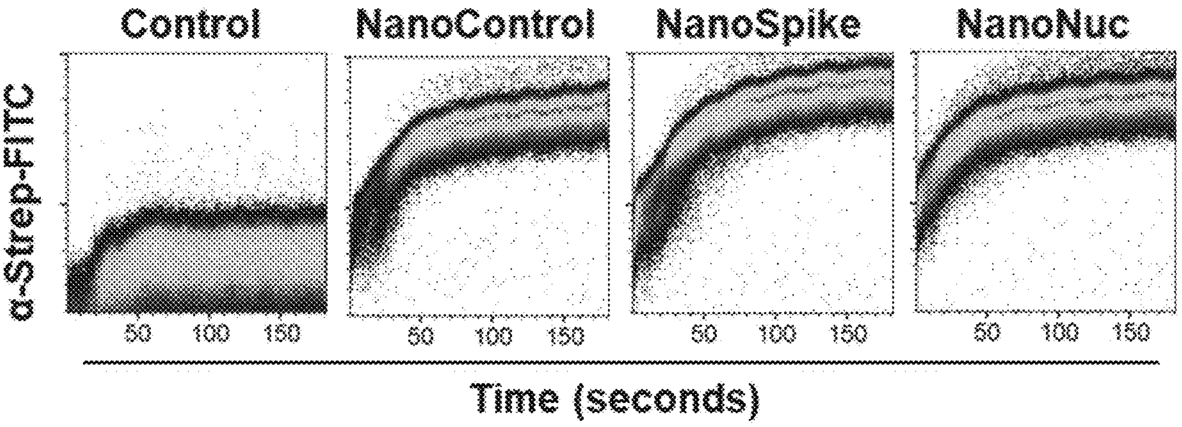
FIG. 7 shows that nanobody-fusion proteins bind RBCs rapidly and quantitatively. Kinetics of RBC-binding of nanobody-fusion proteins analyzed by flow cytometry. Anti-Strep-FITC antibody alone (control) or together with indicated recombinant proteins was added to human RBC (time point 0) and binding was analyzed by flow cytometry during time.

To determine whether the NanoSpike protein binds to red blood cells, different concentrations of the NanoSpike protein were incubated with human whole blood, followed by visualization using FITC-conjugated anti-Strep-tag antibodies and flow cytometry (FIG. 6-7). As expected, NanoSpike bound efficiently and in a concentration-dependent manner to RBC.

In order to determine if NanoSpike cross-linking induces visible hemagglutination of RBC, the NanoSpike protein was added to a small drop (10 μL) of human whole blood, either in the absence of antibodies, anti-Strep antibodies (crosslinking) or anti-CD4 antibodies (negative control). Indeed, in the presence of NanoSpike, anti-Strep antibodies induced instant hemagglutination in a concentration-dependent way. anti-Strep antibodies alone or anti-Strep antibodies in the presence of αCD4 antibodies showed no effect, demonstrating specificity. Given that the anti-Strep antibodies is a monoclonal IgG1 antibodies, these data also suggest that the valency of IgG is sufficient to trigger agglutination (as opposed to the higher valency of IgM).

To obtain proof of principle for NanoSpike activity in the presence of physiological αSpike antibodies, whole blood of a confirmed COVID19 patient was combined with NanoSpike or NanoControl protein. Indeed, similar to the anti-Strep antibody-treated samples, NanoSpike mediated instant hemagglutination. NanoSpike expressed from ExpiCho-S and Expi293F cells showed the same activity. As the protein amount obtained from Expi293F cells was slightly higher, these cells were used for further expression. Of note, NanoControl protein did not exhibit any agglutination, even during extended periods of time, suggesting that agglutination is solely governed by the Spike RBD moiety, respectively antibodies directed against Spike. This experiment was confirmed with two patients two weeks after being tested PCR-positive (not shown).

Example 4

To further substantiate the initial testing described above, five plasma samples from COVID19 patients with ELISA-positive αSARS-CoV-2 antibody titers was tested, along with five confirmed antibody-negative control samples. Plasma was used for these assays because it was immediately available from frozen stocks maintained at a reference laboratory (ARUP). For these assays, washed RBC from a healthy donor were used and combined NanoSpike (or NanoControl) protein along with plasma from test samples. All COVID19-positive samples showed immediate hemagglutination in the presence of NanoSpike, but not the NanoControl protein, while all COVID19-negative samples remained without detectable hemagglutination. Even though blood plasma is not the intended major type of material typically used for the assay (i.e., the preferred sample is finger stick capillary blood), it has the advantage that it can be titrated independent of RBC and was useful to assess the sensitivity of the assay at different antibodies concentrations. This facilitated the testing and optimization of other viral proteins fused to the Nanobody (e.g., NanoNuc, NanoORF8, NanoORF3b, NanoSpikeORF8, NanoSpikeORF3b).

Example 5

Figure 8:
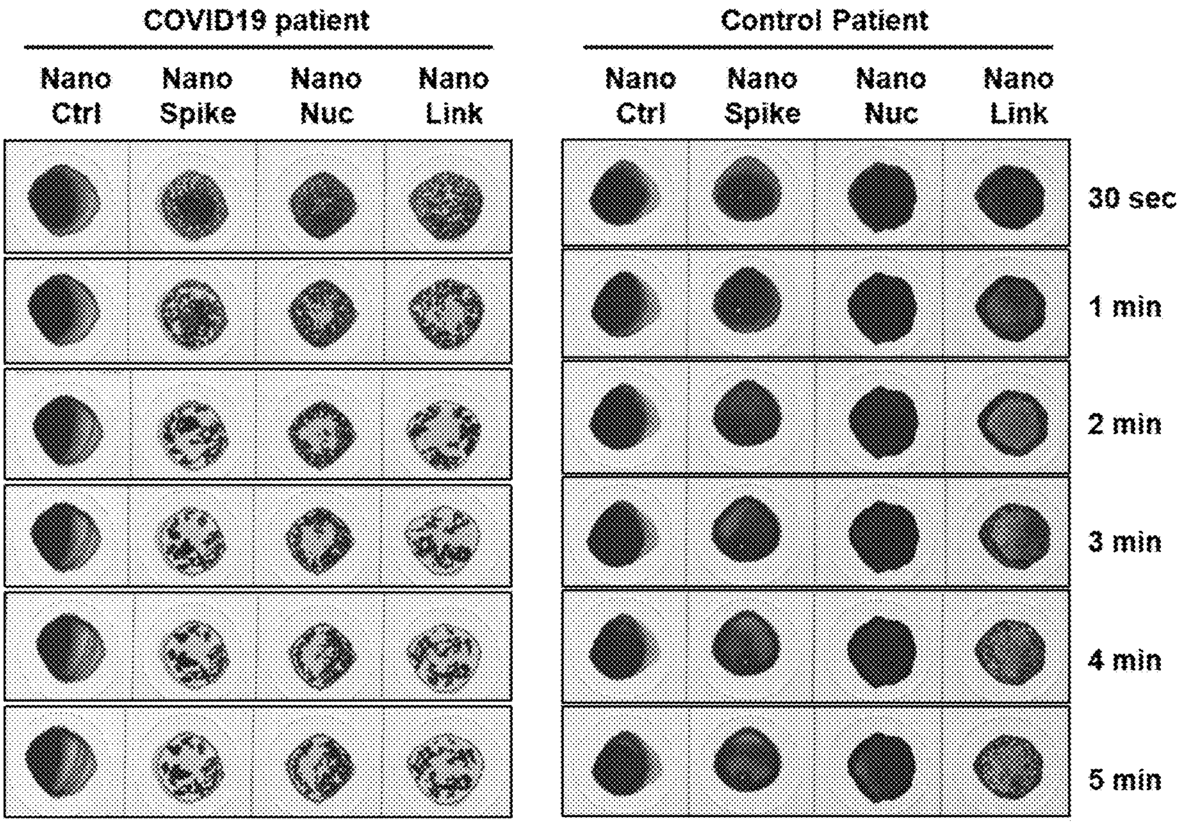
FIG. 8 shows that serum from a COVID19 convalescent patient triggers Nanospike- and NanoNuc-mediated hemagglutination. Indicated recombinant proteins (30 μg/mL) were added to washed RBC along with serum from a COVID19 convalescent patient (left) or a healthy control patient (right). The mixture was spread with a pipette tip and analyzed after a short incubation.

The assay was further validated using serum from patients which had been tested with an FDA-approved Spike-ELISA (Euroimmun). Forty ELISA-positive and forty-two ELISA-negative cases were enrolled. NanoControl, NanoSpike and NanoLink recombinant proteins (30 μg/mL) were added to washed RBC along with the subject serum and the presence or absence of hemagglutination was observed and documented (FIG. 8.). The number of cases that were correctly identified by the NanoSpike test (in a blinded analysis) are shown in Table 2.

Based on these assays, specificity, and sensitivity were calculated according to standard formulas: Sensitivity= number of true test-positive divided by (number of true test-positive plus number of false negatives). Specificity= number of true test-negatives divided by (number of true test-negatives plus number of false positives).

TABLE 2

NanoSpike identifies sero-positive COVID19 patients with high specificity and sensitivity.

| | Euroimmune (Spike) | ELISA (82 patients) |
|---|---|---|
| ELISA (Number of cases) | 40 (test-positive) | 42 (test-negative) |
| NanoSpike Agglutination (number of correct identifications) | 39 | 41 |
| NanoSpike Agglutination (number of incorrect identifications) | 1 | 1 |
| Specificity (%) | 98 | |
| Sensitivity (%) | 98 | |

Example 6

NanoSpike Assay Methodology

Assay Reagents/Components:

Subject sample: blood, serum, plasma, or other bilogical fluid sample (described below)

NanoSpike, NanoNuc, NanoORF8, NanoORF3b, NanoSpikeORF8, NanoSpikeORF3b, or other Nanobody (IH4vs2)-conjugated proteins (20-60 μg/mL): glycophorin targeting nanobody conjugated to SARS-CoV-2 proteins NanoControl (20-60 μg/mL): Negative control, glycophorin targeting nanobody alone NanoLink (20-60 μg/mL): Positive control, test substance (20-60 μg/mL); SARS-CoV-2 Spike-targeting nanobody construct (based on the H11-D4 nanobody) fused to the Hinge-FC part of IgG1 protein. This compound mimics dimerizing anti-Spike antibodies.

NanoTrim (20-60 μg/mL): Positive control, test substance (20-60 μg/mL), SARS-CoV-2 Spike-targeting nanobody construct (based on the H11-D4 nanobody) fused to trimerizing Hinge-isoleucine zipper domain. This compound mimics multimerizing anti-Spike antibodies.

Miscellaneous Items: Test cards; gloves; alcohol (70% isopropanol) towelettes; finger prick lances; bandages; pipets, pipet tips, microfuge tubes, magnifying means, bright light; biohazard disposal receptacle; etc.

Specimen Collection

Total Blood

Blood was collected in vacutainers or collection tubes containing EDTA by venipuncture or finger-stick.

Plasma

Blood was collected in vacutainers containing EDTA by venipuncture and plasma was separated by centrifugation.

Serum

Blood was collected in vacutainers containing no anticoagulants by venipuncture and plasma was separated by centrifugation after the blood had clotted.

Test Procedures (at room temperature, ~25° C.):

Total Blood

A small amount of blood, e.g., 10-20 μL, was combined with test or control solutions at a ratio of ~1:1, gently mixed, and the reaction mixture was spread over the test card field (~1 $cm^2$ diameter).

The test card was rotated manually or with a mechanical rotor at 80-100 rpm for 2-5 minutes and immediately read under direct light.

The presence of hemagglutination was a positive result. The absence of hemagglutination was a negative result. Results were compared to positive and/or negative control samples using the same subject sample.

Plasma and Serum

A small amount of plasma or serum, e.g. 5-10 μL, was combined with a small amount, e.g., 5-10 μL, of washed human red blood cells (RBC) of blood group 0. RBCs can be used pure or diluted with PBS up to 1:10.

The test or control solutions are added to the plasma/serum/RBC mixture at a ratio of 1:1, gently mixed and the reaction mixture was spread over the test field (~1 $cm^2$ diameter).

The test card was rotated manually or with a mechanical rotor at 80-100 rpm for 2-5 minutes and immediately read under direct light.

The presence of hemagglutination was a positive result. The absence of hemagglutination was a negative result. Results were compared to positive and/or negative control samples using the same subject sample.

Hemagglutination can be visually read on cardboard test cards or on glass slides. Alternative assay systems include the use of microtiter plates, gel immunodiffusion, ouchterlony, or automated systems that can detect agglutination, e.g., by still or video imaging, optical density, impedance, microscopy, or using specific applications developed for this purpose.

Exemplary Cost Analysis

One advantage of the assays described herein is their simplicity and low costs. Based on regular prices (not wholesale), estimated material costs for protein expression and purification amount to ~$0.019/assay, and additional equipment (also regular retail prices), including lancets, capillaries, and ethanol wipes amount to ~$0.30/assay. While overhead costs for personnel and logistics need to be accounted, it is expected that up-scaled protein production and wholesale prizes for equipment will further reduce production costs.

What is claimed:

1. A polypeptide comprising a human red blood cell binding antibody domain (RBD) comprising a glycophorin A-binding nanobody comprising a polypeptide sequence comprising the polypeptide sequence of SEQ ID NO: 22 and one or more SARS CoV-2 virus protein domains (CVD) selected from one or more of a spike protein, a nucleocapsid protein, an ORF8 protein, an ORF3b protein, or an envelope protein.

2. The polypeptide of claim 1, wherein the CVD comprises a polypeptide having at least 90-99% identity to all or a portion of SEQ ID NO: 24, 26, 28, or 30.

3. The polypeptide of claim 1, wherein the polypeptide has the structure:

SS-GAP-RBD-GL2-CVD-GL3-AFT or

SS-GL1-RBD-GL2-CVD-GL3-CVD-GL4-AFT;

wherein:

SS is a secretion signal domain;

RBD is the glycophorin A-binding nanobody domain;

GAP, GL1, GL2, GL3, and GL4 are linker domains;

CVD is the SARS CoV-2 virus polypeptide domain comprising a spike protein, nucleocapsid protein, an ORF8 protein, an ORF3b protein, or an envelope protein domains; and AFT is an affinity purification tag sequence.

4. The polypeptide of claim 3, wherein the SS comprises a polypeptide sequence having at least 90-99% identity to SEQ ID NO: 20.

5. The polypeptide of claim 3, wherein the GAP, GL1, GL2, GL3, or GL4 comprises a polypeptide sequence having at least 90-99% identity to one or more of SEQ ID NO: 38, 40, 42, 44, or 46.

6. The polypeptide of claim 3, wherein the affinity purification tag (AFT) comprises a polypeptide sequence having at least 90-99% identity to one or more of SEQ ID NO: 58, 60, 62, or 64.

7. The polypeptide of claim 1, wherein the polypeptide is encoded by a nucleotide sequence having at least 90% to 99% identity to SEQ ID NO: 1, 3, 5, 7, 9, or 11.

8. The polypeptide of claim 1, wherein the polypeptide is encoded by a nucleotide sequence of SEQ ID NO: 1, 3, 5, 7, 9, or 11.

9. A polynucleotide vector comprising a nucleotide sequence of claim 7.

10. A cell comprising a polynucleotide vector of claim 9.

11. The polypeptide of claim 1, wherein the polypeptide has a polypeptide sequence having at least 90% to 99% identity to SEQ ID NO: 2, 4, 6, 8, 10, or 12.

12. The polypeptide of claim 1, wherein the polypeptide has a polypeptide sequence selected from SEQ ID NO: 2, 4, 6, 8, 10, or 12.

13. A control polypeptide comprising:

(a) a glycophorin A-binding nanobody domain comprising the polypeptide sequence of SEQ ID NO: 14;

or (b) one or more anti-SARS Co-V-2 nanobody domains comprising a polypeptide sequence having at least 90-99% identity to SEQ ID NO: 32 and one or more multimerization domains comprising a polypeptide sequence having at least 90-99% identity to SEQ ID NO: 34 or 36.

14. The polypeptide of claim 13, wherein the polypeptide is encoded by a nucleotide sequence having at least 90% to 99% identity to SEQ ID NO: 13, 15, or 17.

15. The polypeptide of claim 13, wherein the polypeptide is encoded by a nucleotide sequence selected from SEQ ID NO: 13, 15, or 17.

16. A polynucleotide vector comprising a nucleotide sequence of claim 14.

17. A cell comprising the polynucleotide vector of claim 16.

18. The polypeptide of claim 13, wherein the polypeptide has a polypeptide sequence of at least 90% to 99% identity to SEQ ID NO: 16, or 18.

19. The polypeptide of claim 13, wherein the polypeptide has a polypeptide sequence selected from SEQ ID NO: 16, or 18.

20. A kit comprising:

(a) one or more diagnostic or control polypeptides having a polypeptide sequence of at least 90% to 99% identity to SEQ ID NO: 2, 4, 6, 8, 10, 12, 14, 16, or 18;

(b) a test substrate; and (c) optionally, a label or instructions for use.

* * * * *